US011161872B2

(12) United States Patent
Liu et al.

(10) Patent No.: US 11,161,872 B2
(45) Date of Patent: Nov. 2, 2021

(54) METHODS FOR PREPARING BILE ACIDS

(71) Applicant: MEDYTOX INC., Cheongju-si (KR)

(72) Inventors: Dejun Liu, Hubei (CN); Yingzhe Qian, Hubei (CN); Junho Lee, Suwon-si (KR); Yoonseok Song, Gunpo-si (KR)

(73) Assignee: MEDYTOX INC., Cheongju-si (KR)

( * ) Notice: Subject to any disclaimer, the term of this patent is extended or adjusted under 35 U.S.C. 154(b) by 0 days.

(21) Appl. No.: 16/636,260

(22) PCT Filed: Aug. 3, 2018

(86) PCT No.: PCT/CN2018/098535

§ 371 (c)(1),
(2) Date: Feb. 3, 2020

(87) PCT Pub. No.: WO2019/024920

PCT Pub. Date: Feb. 7, 2019

(65) Prior Publication Data

US 2020/0369712 A1 Nov. 26, 2020

(30) Foreign Application Priority Data

Aug. 3, 2017 (WO) ................ PCT/CN2017/095784

(51) Int. Cl.

| | |
|---|---|
| ***C07J 9/00*** | (2006.01) |
| ***C07J 5/00*** | (2006.01) |
| ***C07J 1/00*** | (2006.01) |

(52) U.S. Cl.

CPC ............. *C07J 9/005* (2013.01); *C07J 1/0003* (2013.01); *C07J 1/0011* (2013.01); *C07J 1/0018* (2013.01); *C07J 5/0015* (2013.01)

(58) Field of Classification Search

CPC ....... C07J 1/0011; C07J 1/0003; C07J 1/0018
See application file for complete search history.

(56) References Cited

U.S. PATENT DOCUMENTS

| | | | | |
|---|---|---|---|---|
| 7,622,130 | B2 * | 11/2009 | Kolodney | ............ A61K 9/0019 424/401 |
| 7,994,352 | B2 | 8/2011 | Ferrari et al. | |
| 9,238,673 | B2 | 1/2016 | Steiner et al. | |
| 2005/0267080 | A1 | 12/2005 | Kolodney et al. | |
| 2006/0127468 | A1 | 6/2006 | Kolodney et al. | |

FOREIGN PATENT DOCUMENTS

| | | | |
|---|---|---|---|
| CN | 1308085 | A | 8/2001 |
| CN | 101711254 | A | 5/2010 |
| EP | 2407475 | B1 | 8/2015 |
| WO | 2006086038 | A1 | 8/2006 |
| WO | 2008157635 | A2 | 12/2008 |
| WO | 2011075701 | A2 | 6/2011 |
| WO | 2012047495 | A2 | 4/2012 |
| WO | 2015198150 | A2 | 12/2015 |

OTHER PUBLICATIONS

"RN 102399-65-5" STN REG, 1986.
"RN 1258252-84-4," STN REG, 2010.
"RN 26425-68-3," STN REG, 1984.
"RN 413597-22-5," STN REG, 2002.
"RN 80322-20-9," STN REG, 1984.
"RN 88378-76-1", STN REG, 1984.
Deng, L-H, et al., "Synthesis of 5,6-Dihydro-OSW-1 and Its Anti-tumor Activities," Chinese Journal of Chemistry, 2004, vol. 22, pp. 994-998, Chinese Chemical Society.
International Search Report and Written Opinion dated Nov. 1, 2018, in International Application No. PCT/CN2018/098535.
Mukhopadhyay, S., et al., "Chemistry and biology of bile acids," Current Science, 2004, vol. 87:12, pp. 1666-1683, Current Science Association, Bangalore, India.
Extended European Search Report dated May 18, 2021, issued in European Application No. 18841928.7.
Zzo et al., "Efficient Stereocontrolled Access to 15- and 16-Hydroxy Steroids," Eur. J. Org. Chem., 1999, pp. 3505-3510, Wiley-VCH Verlag GmbH, Weinheim, Germany.
Tochtrop et al., "A Simple Efficient Synthesis of [23,24]-13-C2-Labeled Bile Salts as NMR Probes of Protein-Ligand nteractions," Bioorganic & Medicinal Chemistry Letters, 2002, vol. 12, pp. 433-435, Pergamon, Elsevier, Amsterdam, Netherlands.

* cited by examiner

*Primary Examiner* — Susanna Moore
(74) *Attorney, Agent, or Firm* — Potomac Law Group, PLLC

(57) ABSTRACT

The present disclosure provides methods of preparing cholic acid, deoxycholic acid, or chenodeoxycholic acid, an ester thereof, or a pharmaceutically or cosmetically acceptable salt thereof, and novel and useful synthetic intermediates, for example, as described for methods 1, 1A, 1B, 2, 3, 3A, and 4. The method can start with a plant derived steroid as a starting material, such as dehydroepiandrosterone (DHEA) or Acetyl-dehydroepiandrosterone (Ac-DHEA). Also provided are pharmaceutical or cosmetic compositions and uses thereof, which comprise one or more of cholic acid, deoxycholic acid, or chenodeoxycholic acid, an ester thereof, or a pharmaceutically or cosmetically acceptable salt thereof, which is of high purity, for example, free of animal derived impurities.

15 Claims, 2 Drawing Sheets

Signal: RID1 A, Refractive Index Signal

Figure 1:
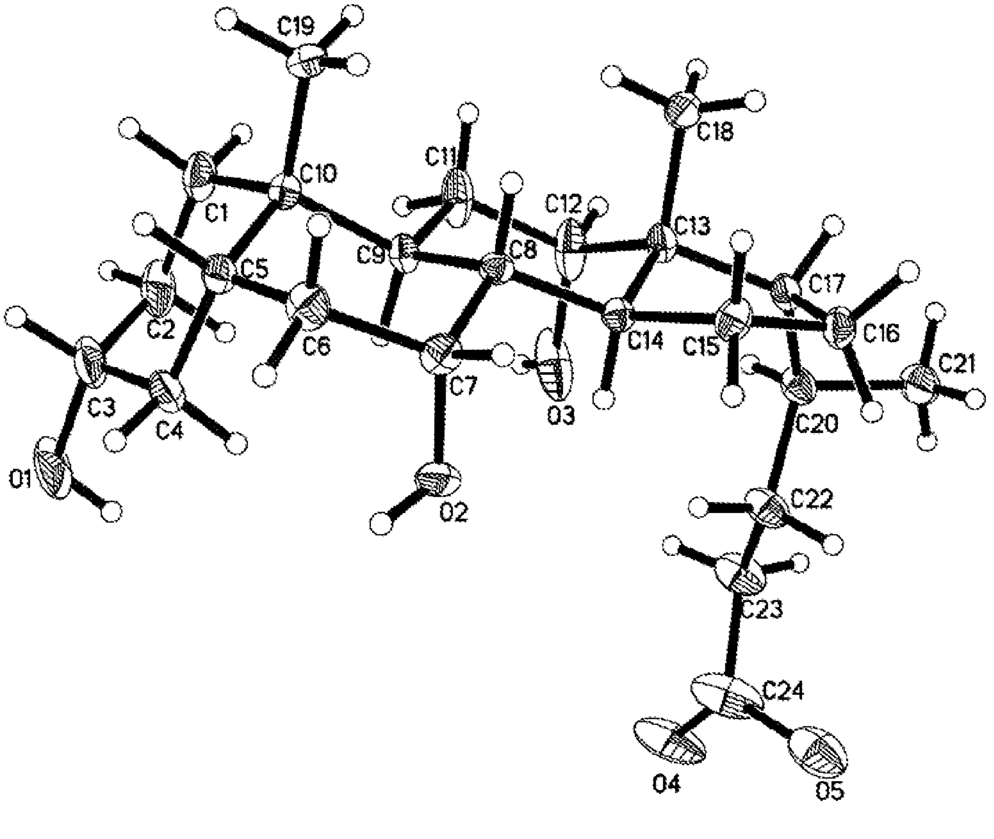

| Retention Time | Compound Name | Width [min] | Height | Area | Area % | Resolution | Peak Theoretical Plates USP | Tail Factor |
|---|---|---|---|---|---|---|---|---|
| 5.024 | Impurity 1 | 0.11 | 156.01 | 1055.50 | 0.13 | | 11868 | 0.89 |
| 8.301 | CA | 0.19 | 62971.97 | 781660.13 | 95.58 | 12.72 | 10066 | 1.45 |
| 9.166 | Impurity 2 | 0.21 | 1178.81 | 16599.68 | 2.03 | 2.56 | 11373 | 1.00 |
| 12.099 | Impurity 3 | 0.22 | 192.07 | 2779.05 | 0.34 | 7.96 | 15172 | 1.23 |
| 15.732 | Impurity 4 | 0.31 | 748.50 | 15707.78 | 1.92 | 7.99 | 14861 | 0.71 |

METHODS FOR PREPARING BILE ACIDS

CROSS-REFERENCE TO RELATED APPLICATION

This application claims priority to international application No. PCT/CN2017/095784, filed on Aug. 3, 2017, the content of which is herein incorporated by reference in its entirety.

BACKGROUND OF THE INVENTION

Field of the Invention

The present disclosure is generally related to the field of steroid synthesis, e.g., methods of preparing a bile acid (e.g., cholic acid, deoxycholic acid, or chenodeoxycholic acid) from a plant derived steroid, and novel synthetic intermediates. The present disclosure is also related to pharmaceutical or cosmetic compositions comprising a bile acid (e.g., cholic acid, deoxycholic acid, or chenodeoxycholic acid) or its ester(s) or salt(s), and pharmaceutical or cosmetic uses thereof.

Background Art

Bile acids such as deoxycholic acid, cholic acid and the like are pharmaceutical and cosmetically useful compounds. See, e.g., Mukhopadhyay, S. and U. Maitra, Current Science 87:1666-1683 (2004) ("Chemistry and Biology of Bile Acids"). Recently, the use of one or more of cholate and chenodeoxycholate has been suggested for non-surgical removal of a localized fat deposit in a subject. See, e.g., WO 2015/198150. Bile acids were typically obtained from bovine and ovine sources. Pathogens such as prions can contaminate such sources. Thus, stringent conditions for mammalian sourced bile acids are required by regulatory authorities. See, e.g., WO 2008/157635 and WO 2011/075701. For example, deoxycholic acid from animals in New Zealand are a source of bile acids for human use under US regulatory regimes, as long as the animals continue to remain isolated and otherwise free of observable pathogens. Such stringent conditions impose a limitation on the amount of suitable mammalian sourced bile acids and do not preclude the possibility that the bile acids will be free of such pathogens.

In light of the stringent conditions for mammalian sourced bile acids noted above, synthetic bile acids such as cholic acid, deoxycholic acid, chenodeoxycholic acid, suitable for use as medicaments or cosmetics in humans are in need. These synthetic bile acids would be synthesized starting from non-animal sources, such as from plant sources or synthetic starting materials. Therefore, the synthetic bile acids can be advantageous at least in that they are known from the outset to be free from animal derived impurities, such as pathogens that are capable of producing a deleterious effect on a human, and other harmful agents such as animal or microbial metabolites, toxins, including bacterial toxins, such as pyrogens.

BRIEF SUMMARY OF THE INVENTION

In various embodiments, the present disclosure is directed to a method of preparing cholic acid, deoxycholic acid, or chenodeoxycholic acid, an ester thereof, or a pharmaceutically or cosmetically acceptable salt thereof. In some embodiments, the method can comprise, consisting essentially of, or consisting of any of the embodiments described below for any of methods 1, 1A, 1B, 2, 3, 3A, and 4. In some embodiments, the method can also comprise, consisting essentially of, or consisting of any of the embodiments according to any of Schemes 1-8. In some embodiments, the method uses a non-animal derived steroid (e.g., plant derived, or synthetic) as a starting material. In some embodiments, the method starts with a plant derived steroid as a starting material, such as dehydroepiandrosterone (DHEA) or Acetyl-dehydroepiandrosterone (Ac-DHEA). In some embodiments, the method starts with a steroid starting material that is free of any animal derived impurities. In some embodiments, the method produces the cholic acid, deoxycholic acid, or chenodeoxycholic acid, ester thereof, or pharmaceutically or cosmetically acceptable salt thereof that is free of any animal derived impurities. Thus, certain embodiments of the present disclosure are also directed to cholic acid, deoxycholic acid, or chenodeoxycholic acid, an ester thereof, or a pharmaceutically or cosmetically acceptable salt thereof, produced by any of the methods described herein.

In some embodiments, the present disclosure also provides novel synthetic intermediates useful for the preparation of cholic acid, deoxycholic acid, or chenodeoxycholic acid, an ester thereof, or a pharmaceutically or cosmetically acceptable salt thereof.

In some embodiments, the present disclosure also provides a high purity cholic acid composition. In some embodiments, the high purity cholic acid composition comprises, consists essentially of, or consists of, cholic acid or a salt thereof, and one or more compounds selected from Compounds 32-35, or a salt thereof. In some embodiments, the total amount of Compounds 32-35 and salts thereof, as applicable, is less than 5% (e.g., less than 5%, less than 4%, less than 3%, less than 2%, less than 1%, less than 0.5%, less than 0.2%, less than 0.1%) by weight and/or by HPLC area of the cholic acid and salt thereof. In some embodiments, the amount of each of Compounds 32-35 and its respective salt, as applicable, is less than 5% (e.g., less than 5%, less than 4%, less than 3%, less than 2%, less than 1%, less than 0.5%, less than 0.2%, less than 0.1%) by weight and/or by HPLC area of the cholic acid and salt thereof. In some embodiments, the cholic acid or salt thereof has a purity of at least 95% (e.g., at least 96%, at least 97%, at least 98%, or at least 99%) by weight and/or by HPLC area. In some embodiments, the high purity cholic acid composition is substantially free or free from an animal derived impurity.

In some embodiments, the present disclosure also provides a pharmaceutical or cosmetic composition comprising one or more of high purity cholic acid, deoxycholic acid, or chenodeoxycholic acid, an ester thereof, or a pharmaceutically or cosmetically acceptable salt thereof. In some embodiments, the pharmaceutical or cosmetic composition comprises an effective amount of high purity (e.g., a purity of at least 98%, at least 99%, at least 99.5%, or at least 99.9% by weight) cholic acid or a pharmaceutically or cosmetically acceptable salt thereof, or a high purity cholic acid composition described herein, and a pharmaceutically or cosmetically acceptable excipient. In some embodiments, the pharmaceutical or cosmetic composition further comprises an effective amount of high purity (e.g., a purity of at least 98%, at least 99%, at least 99.5%, or at least 99.9% by weight) deoxycholic acid or chenodeoxycholic acid, or a pharmaceutically or cosmetically acceptable salt thereof. In any of the embodiments described herein, the high purity cholic acid, deoxycholic acid or chenodeoxycholic acid, or an ester or a pharmaceutically or cosmetically acceptable salt thereof can also be characterized by being free of any animal derived impurities.

Some embodiments of the present disclosure are directed to a method of administering the pharmaceutical or cosmetic composition described herein. In some embodiments, the method is for non-surgical removal of a localized fat deposit in a subject. In some embodiments, the method comprises administering to the subject a pharmaceutical or cosmetic composition comprising a fat-lysing effective amount of high purity (e.g., a purity of at least 98%, at least 99%, at least 99.5%, or at least 99.9% by weight) cholic acid, chenodeoxycholic acid, a pharmaceutically or cosmetically acceptable salt thereof, or a combination thereof, and a pharmaceutically or cosmetically acceptable excipient.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DESCRIPTION OF THE DRAWINGS/FIGURES

FIG. 1 shows a drawing of X-ray structure for Compound 35.

Figure 2:
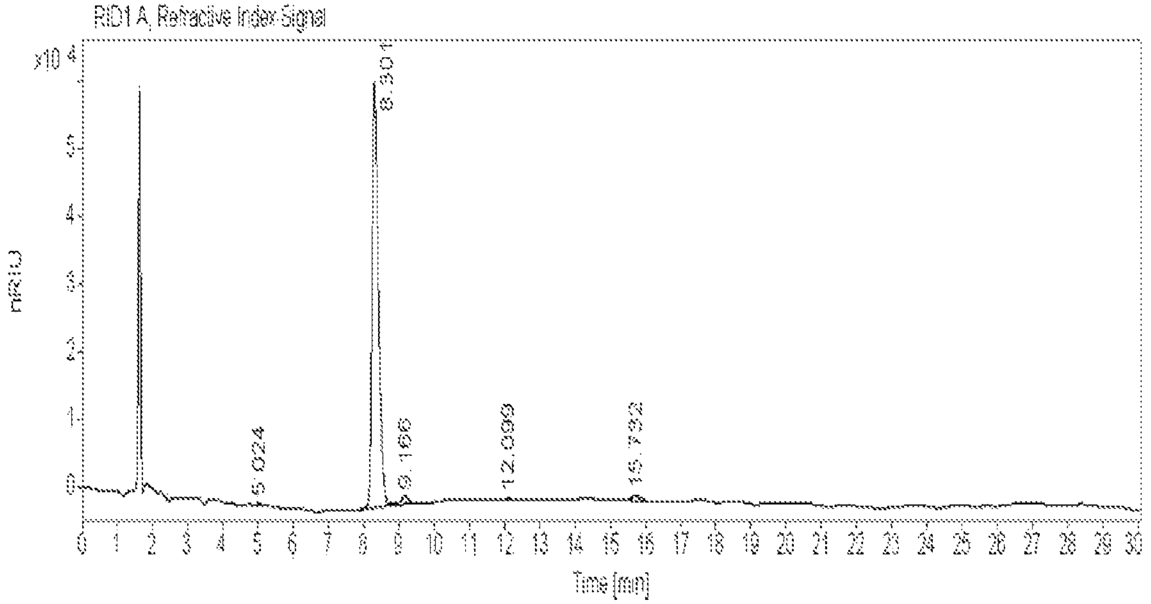

FIG. 2 presents one exemplary HPLC trace showing an impurity profile of cholic acid synthesized by the methods herein (e.g., as shown in Examples 1 and 2). In the HPLC trace, Compound 32 is designated as impurity 1, which has a retention time of 5.02 minutes, Compound 33 is designated as impurity 2, which has a retention time of 9.17 minutes, Compound 34 is designated as impurity 3, which has a retention time of 12.10 minutes, and Compound 35 is designated as impurity 4, which has a retention time of 15.73 minutes.

DETAILED DESCRIPTION OF THE INVENTION

Definitions

It is meant to be understood that proper valences are maintained for all moieties and combinations thereof.

It is also meant to be understood that a specific embodiment of a variable moiety herein may be the same or different as another specific embodiment having the same identifier. For example, $R^1$ in various formulae is independently selected and can be the same or different. Other variables such as $R^{30}$ in various formulae are also independently selected and can be the same or different.

As used herein, the term "animal derived impurities" refers to impurities having an "animal origin," which refers to originating from a kingdom (Animalia) of living things including multi-celled organisms and single celled organisms. In some embodiments, the term "animal derived impurities" can be pathogens, animal or microbial metabolites, and toxins, including bacterial toxins, such as pyrogens.

As used herein, the term "cholic acid (CA)" refers to the compound 3α,7α,12α-trihydroxy-5β-cholan-24-oic acid, which has the following structure:

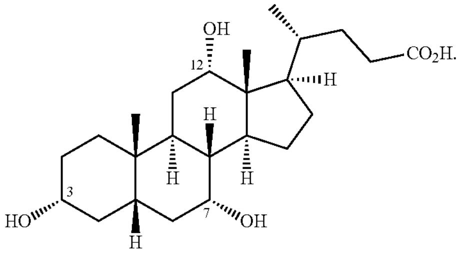

As used herein, a "steroid starting material" refers to a compound having a steroid ring skeleton as follows:

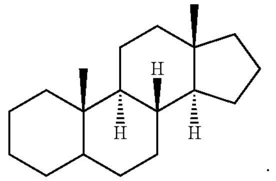

Throughout the present disclosure, the atom and ring numbering in steroid skeletons of the compounds herein follows the convention below:

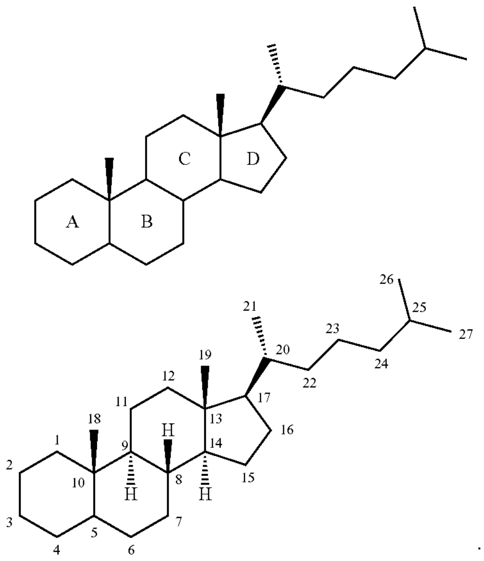

As used herein, the term "chenodeoxycholic acid (CDCA)" refers to the compound 3α,7α-dihydroxy-5β-cholan-24-oic acid, which has the following structure:

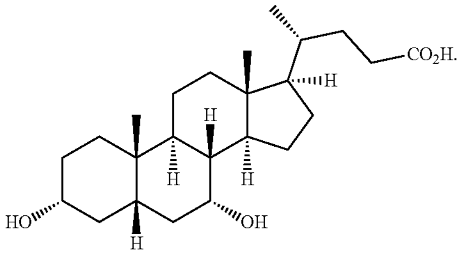

As used herein, the term "deoxycholic acid (DCA)" refers to the compound 3α,12α-dihydroxy-5β-cholan-24-oic acid, which has the following structure:

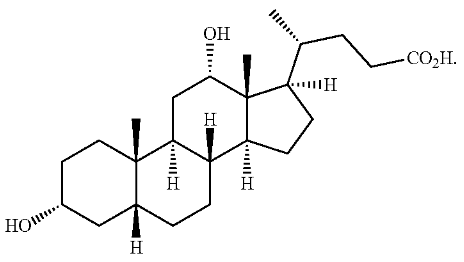

As used herein, the term "pharmaceutically acceptable salt" refers to a salt which is, suitable for pharmaceutical use and is commensurate with a reasonable benefit/risk ratio. Pharmaceutically acceptable salts are known in the art. For example, the bile acids (e.g., CA, DCA, or CDCA) described herein can be in the form of a sodium, potassium, lithium, calcium, magnesium, ammonium, or tetraalkylammonium salt. Suitable salts include those described in P. Heinrich Stahl, Camille G. Wermuth (Eds.), Handbook of Pharmaceutical Salts Properties, Selection, and Use; 2002. These pharmaceutically acceptable salts can be prepared by reacting the bile acids (e.g., CA, DCA, or CDCA) with a suitable base. For illustrative purposes, examples of such bases include sodium hydroxide, potassium hydroxide, or lithium hydroxide. Alternatively, the salts can be prepared by hydrolysis of esters of the bile acids (e.g., CA, DCA, or CDCA) with a base and omitting an acidic workup that would lead to the acid form of the bile acids.

As used herein, the term "cosmetically acceptable salt" refers to a salt which is suitable for cosmetic use and is commensurate with a reasonable benefit/risk ratio. Cosmetically acceptable salts are known in the art and include, for example, base addition salts with a cation selected from the group consisting of sodium ($Na^+$), potassium ($K^+$), lithium ($Li^+$), magnesium ($Mg^{2+}$), calcium ($Ca^{2+}$), barium ($Ba^{2+}$), strontium ($Sr^{2+}$), and ammonium ($NH_4^+$).

The term "subject" as used herein refers to any animal, or cells thereof whether in vitro or in vivo, amenable to the methods described herein. In preferred embodiments, the subject is a human.

As used herein, the term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like.

As used herein, the term "optionally substituted alkyl" refers to an alkyl group that is unsubstituted or substituted (a "substituted alkyl") with one or more substituents (e.g., as described herein, e.g., halogen, such as F).

As used herein, the term "hydroxyl protecting agent" refers to a reagent which under suitable reaction conditions reacts with a hydroxyl group to form a hydroxyl protecting group.

As used herein, the term "hydroxyl protecting group" refers to any group which forms a derivative of the hydroxyl group that is stable to the projected reaction(s), wherein said hydroxyl protecting group subsequently optionally can be selectively removed. The hydroxyl derivative can be obtained by selective reaction of a hydroxyl protecting agent with a hydroxyl group. A person of ordinary skill in the art can select proper hydroxyl protecting group(s) based on the nature of the protecting group(s) and the projected reaction(s). For example, methods for introducing and removing various hydroxyl protecting groups can be found in "Protective Groups in Organic Synthesis", $4^{th}$ ed. P. G. M. Wuts; T. W. Greene, John Wiley, 2007, and in P. J. Kocienski, "Protecting Groups", $3^{rd}$ ed. G. Thieme, 2003, the contents of which are hereby incorporated by reference in their entirety.

Non-limiting examples of hydroxyl protecting groups suitable for the present disclosure include those forming an ether of the hydroxyl group, such as methyl ether, allyl ether, prenyl ether, p-methoxybenzyl ether, triphenylmethyl ether, 2-trimethylsilylethyl ether, tert-butyl ether, cinnamyl ether, propargyl ether, p-methoxyphenyl ether, benzyl ether, 3,4-dimethoxybenzyl ether, 2,6-dimethoxybenzyl ether, o-nitrobenzyl ether, p-nitrobenzyl ether, 4-(trimethylsilylmethyl)-benzyl ether, 2-naphthylmethyl ether, diphenylmethyl ether, (4-methoxyphenyl)-phenylmethyl ether, (4-phenylphenyl)-phenylmethyl ether, p,p'-dinitrobenzhydryl ether, 5-dibenzosuberyl ether, tris(4-tert-butylphenyl)methyl ether, (α-naphthyl)-diphenylmethyl ether, p-methoxyphenyldiphenylmethyl ether, di(p-methoxyphenyl)phenylmethyl ether, tri(p-methoxyphenyl)methyl ether and 9-(9-phenyl)xanthenyl ether.

Non-limiting examples of hydroxyl protecting groups suitable for the present disclosure also include those forming an alkoxyalkylether (e.g., acetals and ketals) of the hydroxyl group, such as 1-ethoxyethyl ether, 1-methyl-1-methoxyethyl ether, [(3,4-dimethoxybenzyl)oxy]methyl ether, guaiacolmethyl ether, 2-methoxyethoxymethyl ether, 2-(trimethylsilyl)ethoxymethyl ether, tetrahydropyranyl ether, tetrahydrofuranyl ether, methoxymethyl ether benzyloxymethyl ether, p-methoxybenzyloxymethyl ether, p-nitrobenzyloxymethyl ether, o-nitrobenzyloxymethyl ether, (4-methoxyphenoxy)methyl ether, tert-butoxymethyl ether, 4-pentenyloxymethyl ether, siloxymethyl ether, 1-methoxycyclohexyl ether, 4-methoxytetrahydropyranyl ether, 1-[(2- chloro-4-methyl)phenyl]-4-methoxypiperidin-4-yl ether, 1-(2-fluorophenyl)-4-methoxypiperidin-4-yl ether, 1-(4-chlorophenyl)-4-methoxypiperidin-4-yl ether or 1-methyl-1-benzyloxyethyl ether.

Non-limiting examples of hydroxyl protecting groups suitable for the present disclosure also include those forming a thioacetal or thioketal of the hydroxyl group, such as tetrahydrothiopyranyl ether, 4-methoxytetrahydrothiopyranyl ether, tetrahydrothiofuranyl ether or 1,3-benzodithiolan-2-yl ether.

Non-limiting examples of hydroxyl protecting groups suitable for the present disclosure also include those forming a silyl ether of the hydroxyl group, such as trimethylsilyl ether, triethylsilyl ether, triisopropylsilyl ether, tert-butyldimethylsilyl ether, dimethylisopropylsilyl ether, diethylisopropylsilyl ether, diphenylmethylsilyl ether, triphenylsilyl ether, dimethylthexylsilyl ether, 2-norbornyldimethylsilyl ether, tert-butyldiphenylsilyl ether, (2-hydroxystyryl)dimethylsilyl ether, (2-hydroxystyryl)diisopropylsilyl ether, tert-butylmethoxyphenylsilyl ether or tert-butoxydiphenylsilyl ether.

Non-limiting examples of hydroxyl protecting groups suitable for the present disclosure also include those forming an ester of the hydroxyl group, such as acetate ester, chloroacetate ester, trifluoroacetate ester, phenoxyacetate ester, formate ester, benzoylformate ester, dichloroacetate ester, trichloroacetate ester, methoxyacetate ester, p-chlorophenoxyacetate ester, phenylacetate ester, 3-phenylpropionate ester, 4-pentenoate ester, 4-oxopentanoate ester, pivaloate ester, crotonate ester, 4-methoxycrotonate ester, angelate ester, benzoate ester or p-phenylbenzoate ester.

Non-limiting examples of hydroxyl protecting groups suitable for the present disclosure also include those forming a carbonate of the hydroxyl group, such as methoxymethyl carbonate, 9-fluorenylmethyl carbonate, methyl carbonate, ethyl carbonate, 2,2,2-trichloroethyl carbonate, 2-(trimethylsilyl)ethyl carbonate, vinyl carbonate, allyl carbonate or p-nitrophenyl carbonate.

Non-limiting examples of hydroxyl protecting groups suitable for the present disclosure also include those forming a sulfenate of the hydroxyl group, such as 2,4-dinitrophenylsulfenate.

As used herein, the term "olefin forming reagent" refers to a regent that can react with a ketone or aldehyde to form an olefin bond under suitable conditions. In some embodiments, the olefin forming reagent can be a Wittig reagent. In some embodiments, the olefin forming reagent can be a phosphorous ylide, or a precursor thereof, e.g., a phosphonium salt that can form the phosphorus ylide under certain conditions (e.g., using a base). In some embodiments, the olefin forming reagent comprises an organometallic reagent (e.g., an organozinc reagent, such as a Reformatsky reagent), wherein the ketone or aldehyde can be converted into an olefin by first forming an alcoholic intermediate with the organometallic reagent, which is followed by dehydration.

As used herein, the term "ylide" refers to a neutral dipolar molecule containing a formally negatively charged atom (usually a carbanion) directly attached to a heteroatom with a formal positive charge (usually nitrogen, phosphorus or sulfur). Thus, when the heteroatom is phosphine, the ylide is a "phosphorous ylide." For example, methylenetriphenylphosphorane ($Ph_3P{=}CH_2$) is a phosphorous ylide.

As used herein, the term "Lewis acid" refers to an electron pair acceptor. Lewis acids include boron reagent such as $BF_3$ (e.g., $BF_3Et_2O$) and oraganometallic reagents such as alkyl aluminum halides (e.g. $Et_2AlCl$ and $MeAlCl_2$).

Synthesis of Cholic Acid, Deoxycholic Acid, and Chenodeoxycholic Acid

Cholic acid includes three hydroxyl groups at positions 3, 7, and 12 of the steroid skeleton. Methods for synthesizing cholic acid can start from a 3,7,12-trioxygenated, a 3,7-dioxygenated or 3,12-dioxygenated, or a 3-oxygenated steroid as a starting material. In some embodiments, cholic acid can be synthesized from a 3,12-dioxygenated steroid starting material. In some embodiments, cholic acid can be synthesized from a 3,7,12-trioxygenated steroid starting material. In some embodiments, cholic acid can be synthesized from a 3,7-dioxygenated steroid starting material. In any of the embodiments described herein, cholic acid can be synthesized from DHEA or Ac-DHEA, which contains a 3-hydroxy or 3-OAc group. Further, methods for preparing cholic acid from DHEA or Ac-DHEA can involve, for example, two broad strategies: (1) introducing the 12-hydroxy group or protected version thereof, and followed by introduction of the 7-hydroxy group or protected version thereof; or (2) introducing the 7-hydroxy group or protected version thereof, and followed by introduction of the 12-hydroxy group or protected version thereof.

Deoxycholic acid has two hydroxyl groups at the 3 and 12 positions and can be synthesized from a 3,12-dioxygenated, or a 3-oxygenated steroid as a starting material. In some embodiments, strategy (1) for cholic acid synthesis from DHEA or Ac-DHEA can also be adapted for the synthesis of deoxycholic acid.

Chenodeoxycholic acid, on the other hand, has two hydroxyl groups at the 3 and 7 positions and can be synthesized from a 3,7-dioxygenated, or a 3-oxygenated steroid as a starting material. Thus, strategy (2) for cholic acid synthesis from DHEA or Ac-DHEA can be adapted for the synthesis of chenodeoxycholic acid.

In some embodiments, the present disclosure also provides cholic acid, deoxycholic acid, or chenodeoxycholic acid, an ester thereof, or a pharmaceutically or cosmetically acceptable salt thereof, produced by any of the methods described herein.

Method 1: Synthesis of Cholic Acid from 3,12-Dioxygenated Steroids

Some embodiments of the present disclosure are directed to a method of preparing cholic acid, an ester thereof, or a pharmaceutically or cosmetically acceptable salt thereof from a 3,12-dioxygenated steroid starting material. A 3,12-dioxygenated steroid starting material refers to a compound having a steroid skeleton with each of the 3 and 12 positions a hydroxyl group or protected version thereof, or a ketone group or protected ketone. For example, in some embodiments, the 3,12-dioxygenated steroid can be a 3,12-diketone compound, a 3,12-dihydroxy compound, or a hydroxyketone compound, having the following ring structure (side chains and other functional groups omitted):
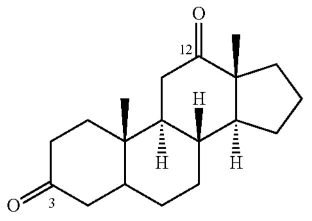
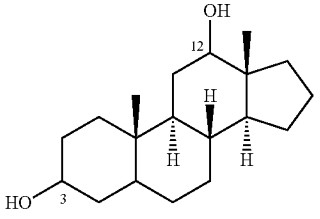
-continued
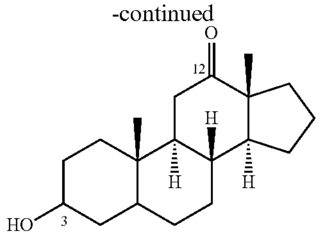
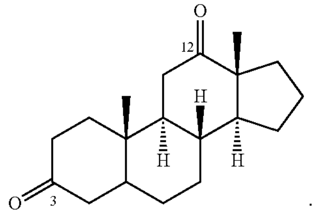
In some embodiments, the 3,12-dioxygenated steroid is a 3,12-diketone compound. For example, the method can comprise a reaction sequence shown in Scheme 1:
Scheme 1
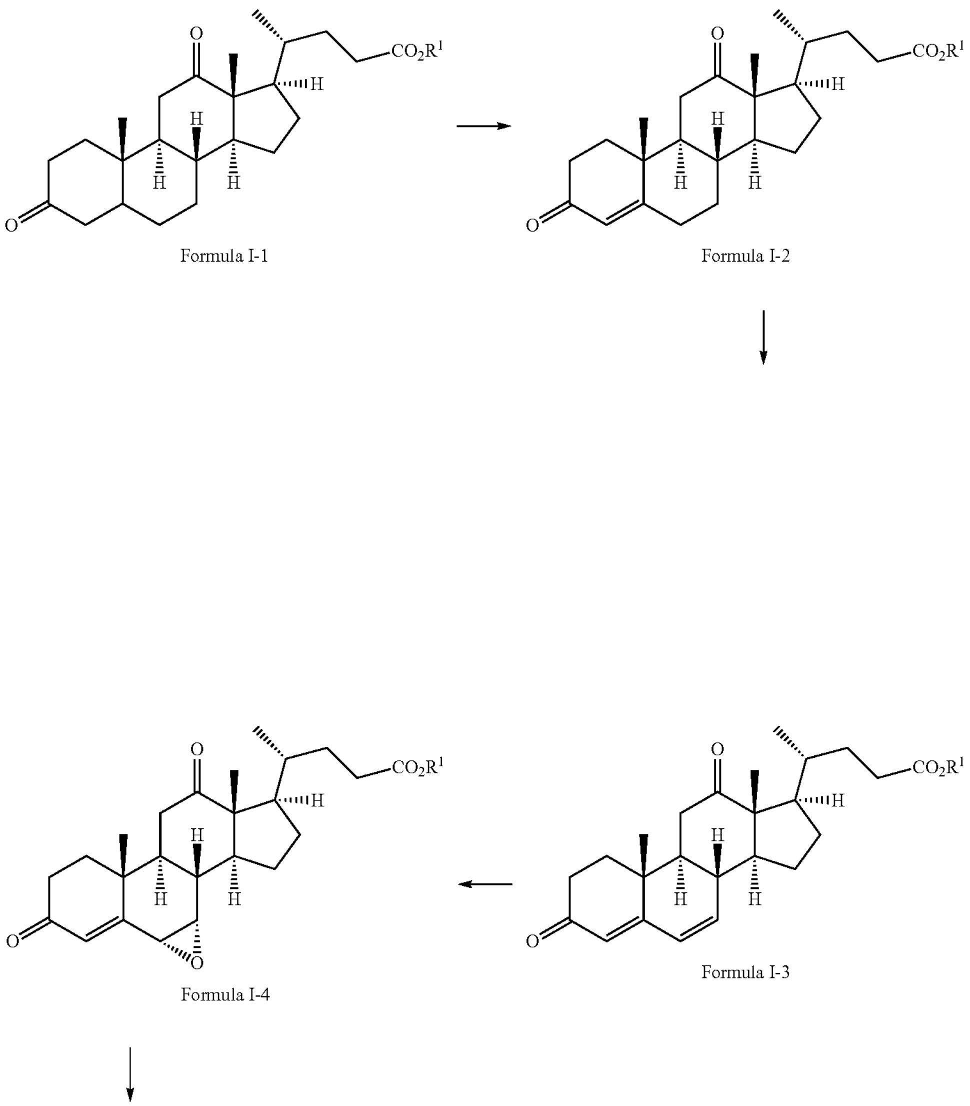
Formula I-1
Formula I-2
Formula I-3
Formula I-4

-continued

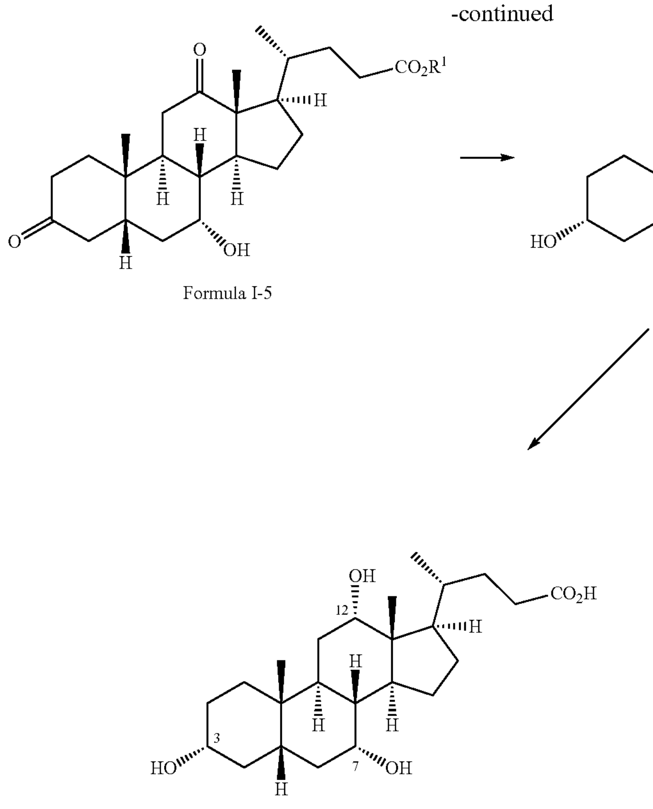

Formula I-5 Formula I-6

Cholic acid wherein $R^1$ is a H or an optionally substituted alkyl.

In some embodiments, the method comprises:

a) converting a compound of Formula I-1 into a compound of Formula I-2,

Formula I-1

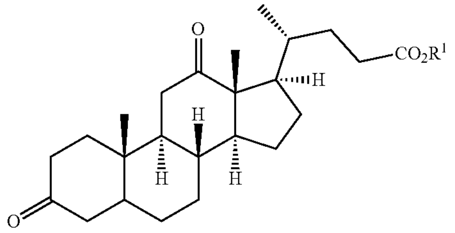

Formula I-2

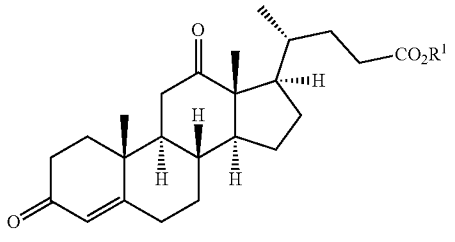

wherein $R^1$ is H or an optionally substituted alkyl group, b) oxidizing the compound of Formula I-2 to form a compound of Formula I-3, Formula I-3

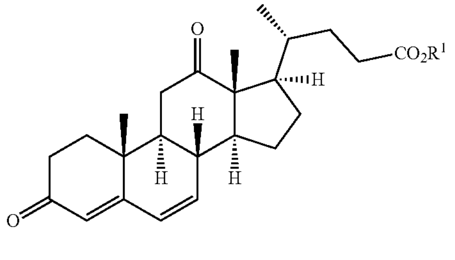

c) reacting the compound of Formula I-3 with an epoxide forming reagent to form an epoxide of Formula I-4

Formula I-4

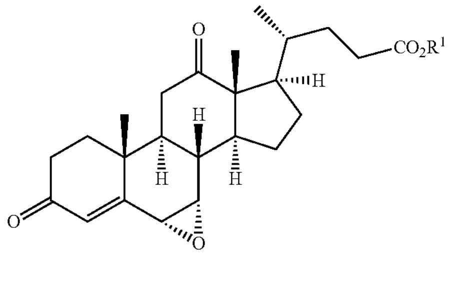

d) reducing the epoxide of Formula I-4 under hydrogenation condition to form a diketone of Formula I-5

Formula I-5

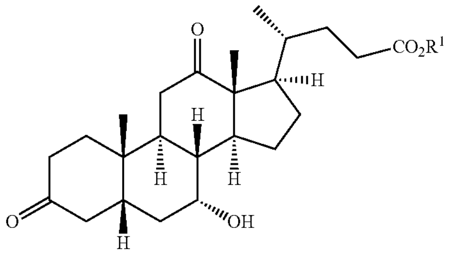

e) contacting the diketone of Formula I-5 with a ketone reducing agent to form a compound of Formula I-6

Formula I-6

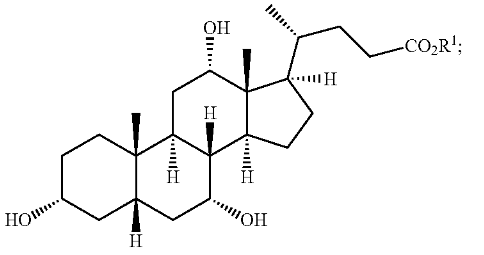

f) optionally, when $R^1$ is not H, hydrolyzing the compound of Formula I-6 to provide cholic acid.

In some embodiments, $R^1$ is hydrogen. However, for ease of purification, in preferred embodiments, $R^1$ is a $C_{1-6}$ alkyl (e.g., methyl or ethyl). In some embodiments, $R^1$ can also be an optionally substituted alkyl (e.g., an optionally substituted $C_{1-6}$ alkyl). For example, $R^1$ can be an alkyl optionally substituted by 1-3 (e.g., 1, 2, or 3) substituents, wherein the 1-3 substituents are independently a $C_{1-6}$ alkyl, $C_{2-6}$ alkenyl, $C_{2-6}$ alkynyl, $C_{3-6}$ carbocyclyl, 3-6 membered heterocyclyl, 5 or 6 membered heteroaryl, phenyl, a substituted phenyl (e.g., para-methoxyphenyl), hydroxyl, $C_{1-6}$alkoxy (e.g., a methoxy, ethoxy, etc.), halogen (e.g., F or Cl), or amino optionally substituted by one or two groups independently selected from $C_{1-6}$ alkyl. In preferred embodiments, $R^1$ is a $C_{1-6}$ alkyl (e.g., methyl or ethyl). The $R^1$ group in Formula I-1 to 1-6 can be the same or different. In some embodiments, $R^1$ group in Formula I-1 to 1-6 can be the same, for example, as a $C_{1-6}$ alkyl (e.g., methyl or ethyl).

Various conditions for effecting the transformations according to Scheme 1 or a), b), c), d), e), and f) described above can be used, which are exemplified in embodiments below and in the Examples section. Other useful conditions and details include those known in the art for analogous transformations.

Certain embodiments of the present disclosure are directed to a method of converting the compound of Formula I-1 into the compound of Formula I-2. Compounds of Formula I-1 useful for this conversion can have a 5-alpha hydrogen or a 5-beta hydrogen. In some embodiments, a substantially pure (e.g., at least 80%, at least 85%, at least 90%, at least 95%, or at least 98% by weight) diastereomer of Formula I-1 can be used, with a 5-alpha hydrogen or a 5-beta hydrogen. In some embodiments, a mixture of diastereomers of Formula I-1 can be used, for example, with a ratio of 5-alpha hydrogen compound to 5-beta hydrogen compound ranging from 50:1 to 1:50. In some embodiments, the converting comprises contacting the compound of Formula I-1 with a halogenating agent to form a halogenated intermediate, and subsequently treating the halogenated intermediate under elimination condition to form the compound of Formula I-2. Halogenating agents suitable for use include those known in the art for introducing an alpha-halogen to a ketone. In some embodiments, the halogenating agent is bromine. In some embodiments, the halogenating agent is N-bromosuccinimide (NBS). The halogenated intermediate formed can have either an alpha or beta configuration:

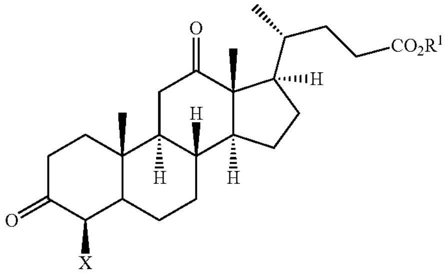

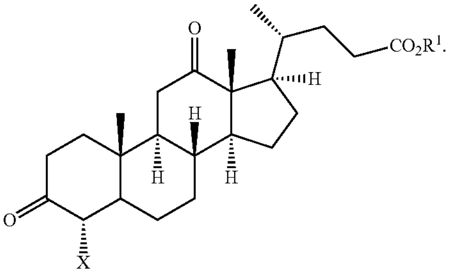

X = halogen

The 5-position stereochemistry of the halogenated intermediate depends on the corresponding stereochemistry of the starting material, Formula I-1, and can have either an alpha or beta hydrogen. In some embodiments, X is bromine and $R^1$ is an optionally substituted alkyl, e.g., a $C_{1-6}$ alkyl (e.g., methyl or ethyl). The halogenated intermediate (e.g., brominated intermediate) can then be treated under elimination condition to form the compound of Formula I-2, an alpha-beta-unsaturated ketone. In some embodiments, the halogenated intermediate is purified prior to the treating under elimination condition. However, preferably, the halogenated intermediate is not purified prior to the treating under elimination condition. Suitable elimination conditions include those known in the art for the elimination of HX (X is halogen, e.g., Br) of an alpha-halogenated ketone. For example, in some embodiments, the elimination condition comprises heating the halogenated intermediate, e.g., to a temperature ranging from 120° C. to 180° C. (e.g., 120° C., 130° C., 140° C., 150° C., 160° C., 170° C., 180° C., or any ranges between the recited values), in the presence of a base (e.g., $Li_2CO_3$) and an agent that facilitates the elimination (e.g., LiBr) in a suitable solvent (e.g., DMF, DMSO). Other methods known in the art for converting a ketone into an alpha-beta-unsaturated ketone can also be used to effect the conversion of the compound of Formula I-1 into the compound of Formula I-2.

Certain embodiments of the present disclosure are directed to a method of converting the compound of Formula I-2 into the compound of Formula I-3, for example, using an oxidizing agent. In some embodiments, the oxidizing agent is a benzoquinone based oxidizing agent such as chloranil (tetrachloro-1,4-benzoquinone) or 2,3-dichloro-5,6-dicyano-1,4-benzoquinone (DDQ). In some embodiments, the method comprises contacting the compound of Formula I-2 with chloranil or DDQ to form the compound of Formula I-3.

Certain embodiments of the present disclosure are directed to a method of converting the compound of Formula I-3 into the epoxide of Formula I-4. The compound of Formula I-3 includes olefin double bonds at the 6,7 positions and at the 4,5 positions, which can be converted into the epoxide of Formula I-4 by using an epoxide forming reagent. In some embodiments, the epoxide forming reagent is a peroxycarboxylic acid. In some embodiments, the epoxide forming reagent is meta-chloroperoxybenzoic acid. Other suitable epoxide forming reagents include those known in the art that can selectively produce an epoxide at the 6,7 positions with the olefin at the 4,5 positions intact.

Certain embodiments of the present disclosure are directed to a method of converting the epoxide of Formula I-4 into the diketone of Formula I-5. Various methods for reducing the epoxide can be used. Preferably, the method comprises hydrogenating the epoxide of Formula I-4. In some embodiments, the hydrogenation is catalyzed by a heterogeneous catalyst, for example, a heterogeneous metal catalyst comprising Pd, Ni, Pt, $PtO_2$, Rh, or Ru. In some embodiments, the heterogeneous metal catalyst is Pd/C. The hydrogenation can be conducted at various $H_2$ pressures. In some embodiments, the hydrogenation is conducted at a hydrogen pressure of at or near 1 atm. In some embodiments, the hydrogenation is conducted at a hydrogen pressure of greater than 1 atm (e.g., about 2 atms, about 3 atms, about 5 atms, about 10 atms, about 15 atms, or any ranges between the recited values). In some embodiments, the hydrogenation is conducted at a hydrogen pressure of about 15 psi to about 100 psi (e.g., about 50 psi).

Certain embodiments of the present disclosure are directed to a method of converting the diketone of Formula I-5 into the compound of Formula I-6, for example, using a ketone reducing agent. In some embodiments, the ketone reducing agent is a borohydride (such as $NaBH_4$, $NaCNBH_3$, etc.) or a trialkoxyaluminum hydride (e.g., tri-isopropoxyaluminum hydride, tri-tert-butoxyaluminum hydride). In preferred embodiments, the ketone reducing agent is lithium tri-tert-butoxyaluminum hydride ($LiAlH(O\text{-}tBu)_3$).

When $R^1$ is not hydrogen, for example, when $R^1$ is a $C_{1-6}$ alkyl, then to synthesize cholic acid, the method further comprises hydrolyzing the compound of Formula I-6. Thus, in some embodiments, when $R^1$ is not hydrogen, the method comprises hydrolyzing the compound of Formula I-6. Suitable hydrolyzing conditions include those known in the art. For example, the hydrolysis can be effected by reacting the compound of Formula I-6 under acid-mediated (e.g., $BF_3$ mediated), base-mediated (e.g., using an alkali metal hydroxide (e.g., NaOH or LiOH)), or nucleophile-mediated (e.g., $I^-$ mediated) hydrolysis conditions. In preferred embodiments, the hydrolysis comprises contacting the compound of Formula I-6 with an alkali metal hydroxide (e.g., NaOH or LiOH).

In some embodiments, an ester of cholic acid, e.g., the compound of Formula I-6 wherein $R^1$ is an optionally substituted alkyl, is the desired product. For example, in some embodiments, the method is directed to the synthesis of a pharmaceutically or cosmetically acceptable ester of cholic acid. In such embodiments, the preferred reaction conditions for sequences a)-e) are those that no or minimal hydrolysis of the ester (i.e., $—CO_2R^1$) occurs under the respective reaction conditions. However, if desired, the ester of cholic acid can also be prepared by esterification of cholic acid with a desired alcohol.

In some embodiments, a salt of cholic acid is the desired product. For example, in some embodiments, the method is directed to the synthesis of a pharmaceutically or cosmetically acceptable salt of cholic acid. Thus, in some embodiments, the method comprises forming a pharmaceutically or cosmetically acceptable salt of cholic acid, for example, by reacting cholic acid with a suitable base, e.g., metal or ammonium hydroxide (e.g., sodium, potassium, lithium, calcium, magnesium, ammonium, or tetraalkylammonium hydroxide).

The compound of Formula I-1 used in the methods described hereinabove can be prepared via different methods. In any of the embodiments described herein, the compound of Formula I-1 can be prepared by the methods described herein, e.g., Method 1A below. In any of the embodiments described herein, the compound of Formula I-1 can also be a synthetic material free of any animal derived impurities.

Method 1A: Synthesis of 3,12-Dioxygenated Steroid of Formula I-1

Certain embodiments of the present disclosure are directed to the synthesis of the compound of Formula I-1, wherein $R^1$ is H or an optionally substituted alkyl group. Formula I-1 can have a 5-alpha hydrogen or a 5-beta hydrogen. In some embodiments, compounds of Formula I-1 exist as a substantially pure (e.g., at least 80%, at least 85%, at least 90%, at least 95%, or at least 98% by weight) diastereomer, with a 5-alpha hydrogen or a 5-beta hydrogen. In some embodiments, compounds of Formula I-1 exist as a diastereomeric mixture in various ratios, for example, with a ratio of 5-alpha hydrogen compound to 5-beta hydrogen compound ranging from 50:1 to 1:50.

Formula I-1

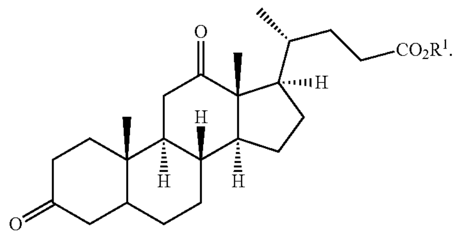

In some embodiments, the compound of Formula I-1 can be synthesized according to Scheme 2, wherein each variables and transformations are as described herein:

Scheme 2

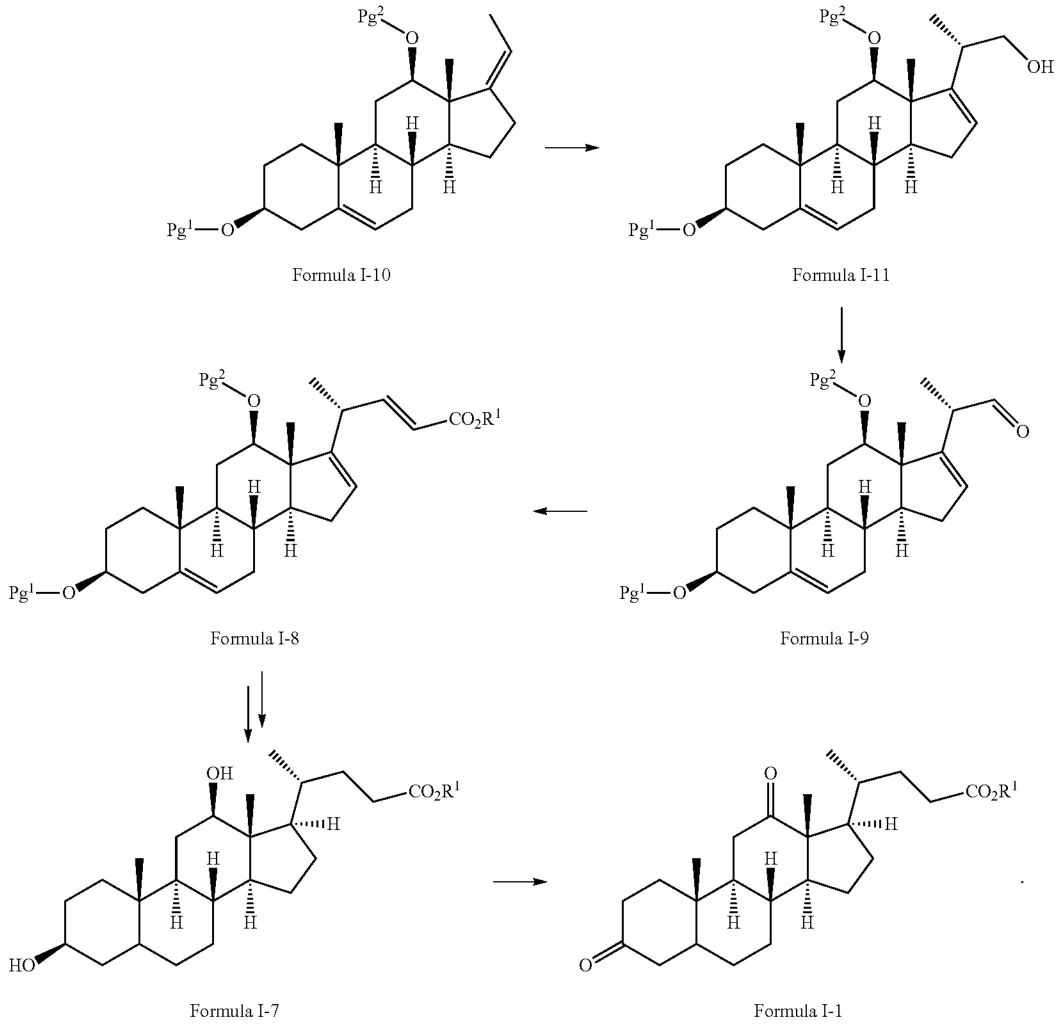

Formula I-10, Formula I-11, Formula I-9, Formula I-8, Formula I-7, Formula I-1

Certain embodiments are directed to a method of oxidizing a diol of Formula I-7 to provide the compound of Formula I-1

Formula I-7

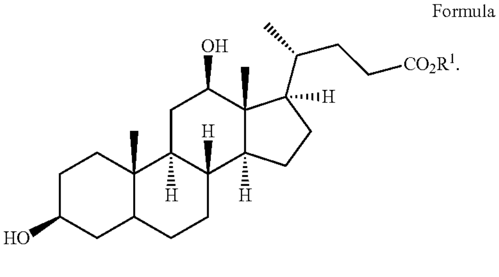

Formula I-7 can have a 5-alpha hydrogen or a 5-beta hydrogen. In some embodiments, compounds of Formula I-7 exist as a substantially pure (e.g., at least 80%, at least 85%, at least 90%, at least 95%, or at least 98% by weight) diastereomer, with a 5-alpha hydrogen or a 5-beta hydrogen. In some embodiments, compounds of Formula I-7 exist as a diastereomeric mixture in various ratios, for example, with a ratio of 5-alpha hydrogen compound to 5-beta hydrogen compound ranging from 50:1 to 1:50. In some embodiments, the oxidizing comprises a Chromium trioxide or chromate based oxidation or variations thereof. In some embodiments, the oxidizing comprises a Swern oxidation or variations thereof. In some embodiments, the oxidizing comprises a hypervalent iodine mediated oxidation. In some embodiments, the oxidizing comprises contacting the diol of Formula I-7 with a suitable oxidizing agent. In some embodiments, the oxidizing agent is a Chromium based oxidizing agent, for example, Jones reagent (a solution of chromium trioxide in dilute sulfuric acid); PCC (pyridinium chlorochromate), etc. In a preferred embodiment, the oxidizing agent is Jones reagent. In some embodiments, the oxidizing agent is a Swern oxidation reagent. As used herein, the term “Swern oxidation reagent” encompasses all activated forms of DMSO, such as a chlorosulfonium active species, that can oxidize an alcohol into a ketone or aldehyde in the presence of an organic base such as triethyl amine or diisopropylethylamine. Various Swern oxidation reagent systems are known. For example, a typical Swern oxidation can include using a DMSO/oxalyl chloride based system, in which DMSO first reacts with oxalyl chloride to generate a chloro (dimethyl)sulfonium chloride, which then converts an alcohol into an aldehyde or ketone group in the presence of an organic base (e.g., $Et_3N$). Other exemplary useful oxidizing agents include reagents for Swern oxidation or variations thereof which use cyanuric chloride, trifluoroacetic anhydride, carbodiimides, pyridine-sulfur trioxide complex to active DMSO, or use dimethyl sulfide and N-chlorosuccinimide to generate the chlorosulfonium active species. In some embodiments, the oxidizing agent can be 2-iodoxybenzoic acid (IBX) or Dess-Martin periodinane (1,1,1-Triacetoxy-1,1-dihydro-1,2-benziodoxol-3 (1H)-one).

In some embodiments, the diol of Formula I-7 can be synthesized by hydrogenating a compound of Formula I-8 or Formula I-8a, or a geometric isomer thereof, Formula I-8

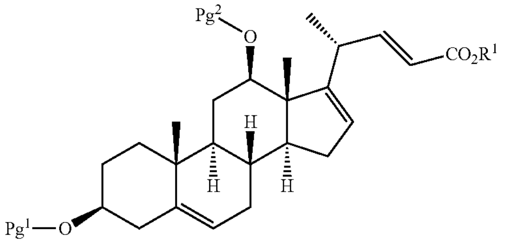

Formula I-8a

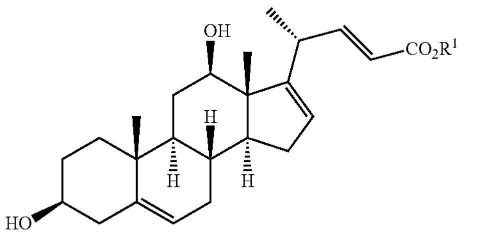

wherein $Pg^1$ and $Pg^2$ are independently a hydroxyl protecting group; and optionally removing the hydroxyl protecting groups. Suitable hydroxyl protecting groups include any of those known in the art, for example, those described herein. In some embodiments, $Pg^1$ and $Pg^2$ are the same. In some embodiments, $Pg^1$ and $Pg^2$ are different. In preferred embodiments, both $Pg^1$ and $Pg^2$ are hydroxyl protecting group that forms an ester with the hydroxyl group, for example, both $Pg^1$ and $Pg^2$ are acetyl. In some embodiments, the diol of Formula I-7 is synthesized by hydrogenating the compound of Formula I-8a. In some embodiments, the diol of Formula I-7 is synthesized by hydrogenating the compound of Formula I-8, which is followed by removing the hydroxyl protecting groups. In some embodiments, the diol of Formula I-7 is synthesized by removing the hydroxyl protecting groups of the compound of Formula I-8 to produce the compound of Formula I-8a, which is followed by hydrogenating the compound of Formula I-8a.

As the olefin double bonds in Formula I-8 or Formula I-8a are hydrogenated to form the diol of Formula I-7, the geometric isomers of the compounds of Formula I-8 and Formula I-8a can also be used. In some embodiments, the method comprises hydrogenating a compound of Formula I-8 or Formula I-8a. In some embodiments, the method comprises hydrogenating a geometric isomer of the compound of Formula I-8 or Formula I-8a. In some embodiments, the method comprises hydrogenating a mixture of the compound of Formula I-8 or Formula I-8a, and its geometric isomers.

Various methods for hydrogenating the compound of Formula I-8 or Formula I-8a can be used. Preferably, the method comprises hydrogenating the compound of Formula I-8 or Formula I-8a with $H_2$ in the presence of a heterogeneous catalyst, for example, a heterogeneous metal catalyst comprising Pd, Ni, Pt, $PtO_2$, Rh, or Ru. In some embodiments, the heterogeneous metal catalyst is Pd/C. The hydrogenation can be conducted at various $H_2$ pressures. In some embodiments, the hydrogenation is conducted at a hydrogen pressure of at or near 1 atm. In some embodiments, the hydrogenation is conducted at a hydrogen pressure of greater than 1 atm (e.g., about 2 atms, about 3 atms, about 5 atms, about 10 atms, about 15 atms, or any ranges between the recited values). In some embodiments, the hydrogenation is conducted at a hydrogen pressure of about 15 psi to about 100 psi (e.g., about 50 psi).

The compound of Formula I-8 can be obtained, for example, from reacting an aldehyde of Formula I-9 with an olefin forming reagent:

Formula I-9

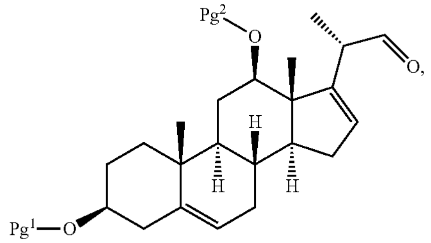

wherein $Pg^1$ and $Pg^2$ are independently a hydroxyl protecting group as described hereinabove. Various olefin forming reagents are suitable for this transformation. Preferably, the reaction and work-up conditions are controlled such that no or minimal epimerization at the C20 position occurs. In some embodiments, the olefin forming reagent comprises a phosphonate substituted acetate:

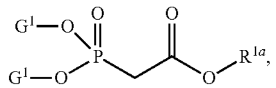

wherein $G^1$ at each occurrence and $R^{1a}$ are each independently an optionally substituted alkyl group (e.g., an optionally substituted $C_{1-6}$ alkyl, e.g., ethyl). The phosphonate substituted acetate can be deprotonated to form a phosphonate-stabilized carbanion, which reacts with the aldehyde group in Formula I-9 to form an alpha-beta-unsaturated ester. In some embodiments, the olefin forming reagent is ethyl 2-diethoxyphosphorylacetate. In some embodiments, the olefin forming reagent is a phosphorus ylide (e.g., triphenylcarbethoxymethylenephosphorane) or its precursor. In some embodiments, the olefin forming reagent can comprise an organometallic reagent, such as an organozinc reagent, which reacts with the aldehyde group in Formula I-9 to form a secondary alcohol, which upon dehydration, forms an alpha-beta-unsaturated ester. For example, in some embodiments, the olefin forming reagent comprises a two-carbon Reformatsky reagent:

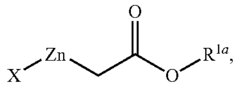

wherein X is halo, such as Cl, Br or I, and $R^{1a}$ is an optionally substituted alkyl group (e.g., an optionally substituted $C_{1-6}$ alkyl, e.g., ethyl). In preferred embodiments, the ester group of the olefin forming reagent (e.g., $R^{1a}$ in either of the phosphonate or the Reformatsky reagent) is the same as $COOR^1$ and $R^1$ is not H. However, in some embodiments, $R^{1a}$ is different from $R^1$, for example, when $R^1$ is H. In such embodiments, the method can optionally further include converting the $—CO_2R^{1a}$ in Formula I-8b into $—CO_2R^1$ in Formula I-8

Formula I-8b

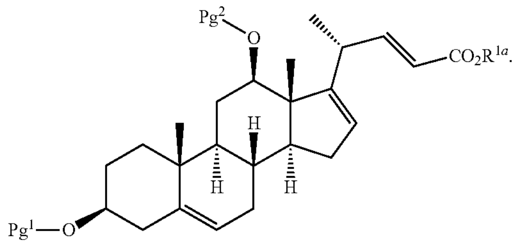

The aldehyde of Formula I-9 can be formed from oxidizing the corresponding alcohol of Formula I-11:

Formula I-11

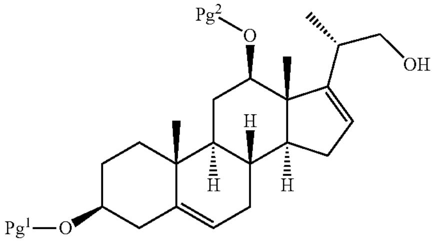

wherein $Pg^1$ and $Pg^2$ are independently a hydroxyl protecting group as described hereinabove. In some embodiments, the oxidizing comprises a Chromium trioxide or chromate based oxidation or variations thereof. In some embodiments, the oxidizing comprises a Swern oxidation or variations thereof. In some embodiments, the oxidizing comprises a hypervalent iodine mediated oxidation. In some embodiments, the oxidizing comprises contacting the compound of Formula I-11 with a suitable oxidizing agent. Various oxidizing agents are suitable. In some embodiments, the oxidizing agent is a Chromium based oxidizing agent, for example, PCC (pyridinium chlorochromate). In some embodiments, the oxidizing agent is a Swern oxidation reagent. Various Swern oxidation reagent systems are known. For example, a typical Swern oxidation can include using a DMSO/oxalyl chloride based system, in which DMSO first reacts with oxalyl chloride to generate a chloro(dimethyl)sulfonium chloride, which then converts an alcohol into an aldehyde or ketone group in the presence of an organic base (e.g., $Et_3N$). Other exemplary useful oxidizing agents include reagents for Swern oxidation or variations thereof which use cyanuric chloride, trifluoroacetic anhydride, carbodiimides, pyridine-sulfur trioxide complex to active DMSO, or use dimethyl sulfide and N-chlorosuccinimide to generate the chlorosulfonium active species. In some embodiments, the oxidizing agent can be 2-iodoxybenzoic acid (IBX) or Dess-Martin periodinane (1,1,1-Triacetoxy-1,1-dihydro-1,2-benziodoxol-3(1H)-one). Preferably, the reaction and work-up conditions are controlled such that no or minimal epimerization at the C20 position occurs.

Various methods can be employed for the synthesis of the compound of Formula I-11. In preferred embodiments, the compound of Formula I-11 can be synthesized from the compound of Formula I-10 or a geometric isomer thereof:

Formula I-10

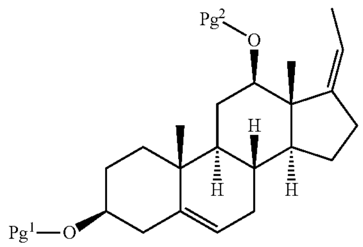

wherein $Pg^1$ and $Pg^2$ are independently a hydroxyl protecting group as described hereinabove. In some embodiments, the method comprises reacting the compound of Formula I-10 with formaldehyde or paraformaldehyde in the presence of a Lewis acid. Various Lewis acids can be used for this transformation, for example, boron or aluminum based Lewis acids can be used. In some embodiments, the Lewis acid comprises $BF_3$. Other suitable Lewis acids include those known in the art that can facilitate an analogous reaction of an olefin with an aldehyde to provide an alcohol.

The compound of Formula I-10 used in the methods described hereinabove can be prepared via different methods. In any of the embodiments described herein, the compound of Formula I-10 can be prepared by the methods described herein, e.g., Method 1B below. In any of the embodiments described herein, the compound of Formula I-10 can also be a synthetic material free of any animal derived impurities.

Method 1B: Synthesis of 3,12-Dioxygenated Steroid of Formula I-10

Certain embodiments of the present disclosure are directed to a method of preparing a compound of Formula I-10, or a geometric isomer thereof, wherein $Pg^1$ and $Pg^2$ are independently a hydroxyl protecting group. In some embodiments, the method comprises obtaining the compound of Formula I-10 from DHEA or a protected DHEA (e.g., acetyl-DHEA) as exemplified in Scheme 3, wherein $R^2$, $R^3$, $Pg^1$ and $Pg^2$ are defined herein:

Scheme 3

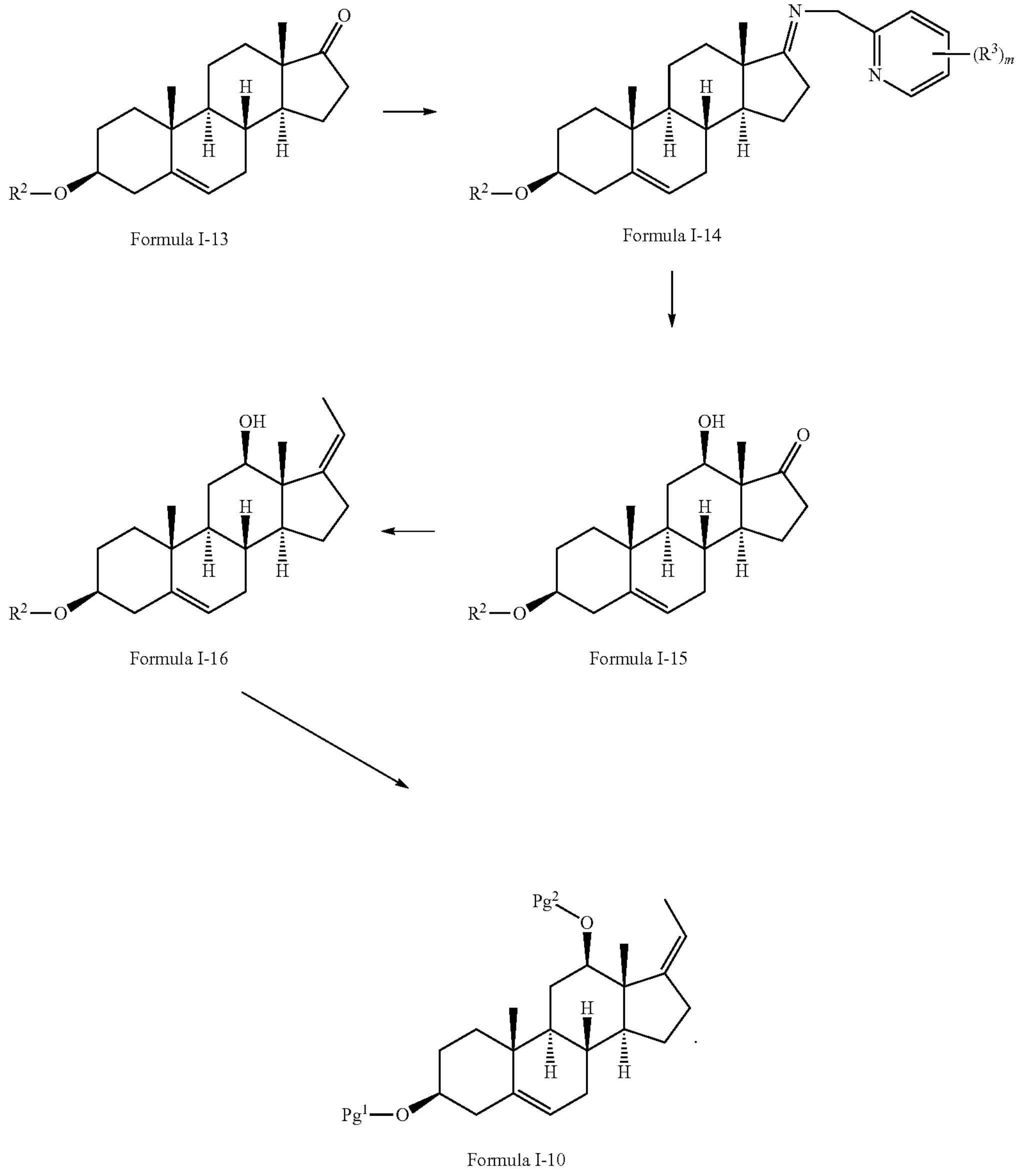

Formula I-13
Formula I-14
Formula I-15
Formula I-16
Formula I-10

In some embodiments, the method comprises:

a) reacting a compound of Formula I-13

Formula I-13

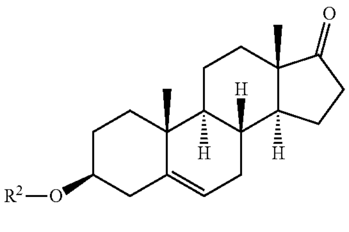

wherein $R^2$ is H or $Pg^1$; and $Pg^1$ is a hydroxyl protecting group (e.g., as described herein); with an amine to form an imine of Formula I-14

Formula I-14

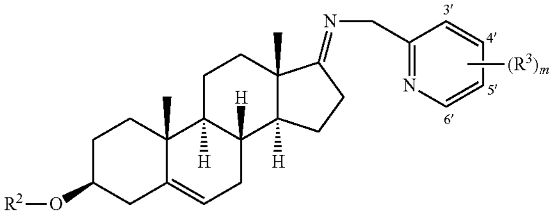

wherein m is 0, 1 or 2, and $R^3$ is $C_{1-6}$ alkyl (e.g., a methyl group at the 4'-position);

b) oxidizing the imine of Formula I-14 with $O_2$ in the presence of a copper salt to form a compound of Formula I-15

Formula I-15

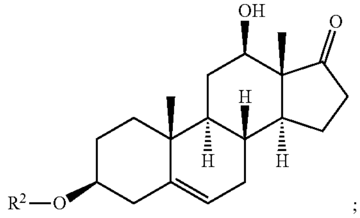

;

c) reacting the compound of Formula I-15 with an olefin forming reagent to form a compound of Formula I-16, or a geometric isomer thereof, Formula I-16

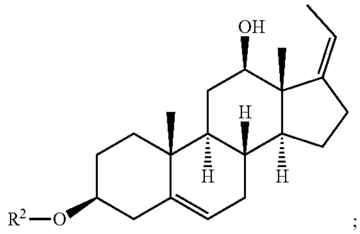

;

d) protecting the hydroxyl group(s) in Formula I-16 to provide the compound of Formula I-10, or geometric isomer thereof.

In some embodiments, the protection of the 12-hydroxy group can occur prior to the olefination of the 17-ketone function in Formula I-15. Thus, in some embodiments, the method can also comprise:

c') protecting the hydroxyl group(s) in the compound of Formula I-15 to form a compound of Formula I-15a Formula I-15a

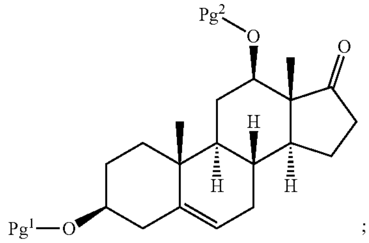

;

and d') then reacting the compound of Formula I-15a with an olefin forming reagent to provide the compound of Formula I-10, or geometric isomer thereof.

The imine formation of a), the copper mediated oxidation of b), and the olefination reaction of c) do not require the 3-hydroxy group to be protected. Thus, in some embodiments, the method can start with DHEA, i.e., $R^2$ is H. In some embodiments, the method can start with a protected version of DHEA, where $R^2$ is $Pg^1$, e.g., acetyl.

Various imines of Formula I-14 are suitable for the methods for preparing the compound of Formula I-10. In some embodiments, the pyridine ring in Formula I-14 is unsubstituted, i.e., m is 0. In some embodiments, the pyridine ring in Formula I-14 is substituted by one or two C1-6 alkyl groups. For example, in some embodiments, the pyridine ring in Formula I-14 is substituted at the 4'-position with a methyl group. The imine formation of a) is generally catalyzed by an acid, for example, para-toluenesulfonic acid.

Suitable copper salt for b) includes any of those known in the art for analogous transformations. In some embodiments, the copper salt is a copper (II) salt such as $Cu(OTf)_2$. In some embodiments, the copper salt is a copper (I) salt such as $Cu(MeCN)_4PF_6$.

In some embodiments, the olefin forming reagent in c) or d') can be a phosphorous ylide. In some embodiments, the olefin forming reagent in c) or d') can be ethylenetriphenylphosphorane or its precursor ethyltriphenylphosphonium salt. In some embodiments, the olefin forming reagent comprises a two-carbon organometallic reagent (e.g., an organozinc reagent), wherein the 17-ketone of Formula I-15 or Formula I-15a can be converted into an olefin by first forming an alcoholic intermediate with the organometallic reagent, which is then followed by dehydration.

Various protecting groups can be used for protecting either or both the 3- and 12-hydroxy groups. The protecting groups for the 3- and 12-hydroxy groups do not need to be the same. However, in preferred embodiments, $Pg^1$ and $Pg^2$ are the same, for example, both $Pg^1$ and $Pg^2$ are acetyl.

Method 2: Synthesis of Deoxycholic Acid from 3,12-Dioxygenated Steroids

Deoxycholic acid (DCA) contains two hydroxyl groups at the 3,12-positions, which can therefore be prepared by an intermediate such as a compound of Formula I-1 (in the beta form with a 5-beta hydrogen, Formula I-1b) through a reduction reaction. In some embodiments, the present disclosure is directed to a method of preparing deoxycholic acid, an ester thereof, or a pharmaceutically or cosmetically acceptable salt thereof from a 3,12-dioxygenated steroid. In some embodiments, the method comprises a reaction sequence according to Scheme 4:

Scheme 4

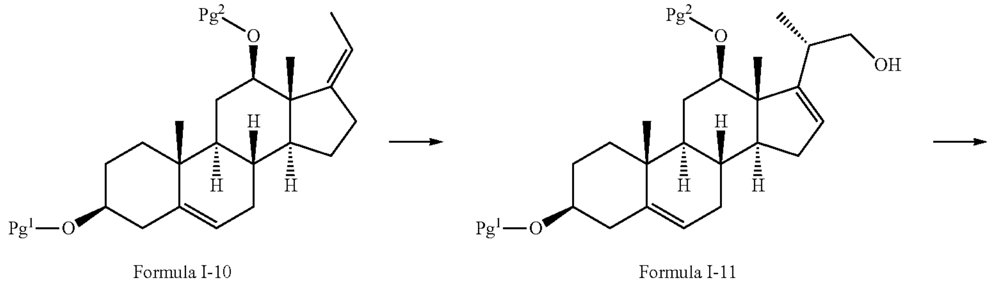

Formula I-10 Formula I-11

-continued

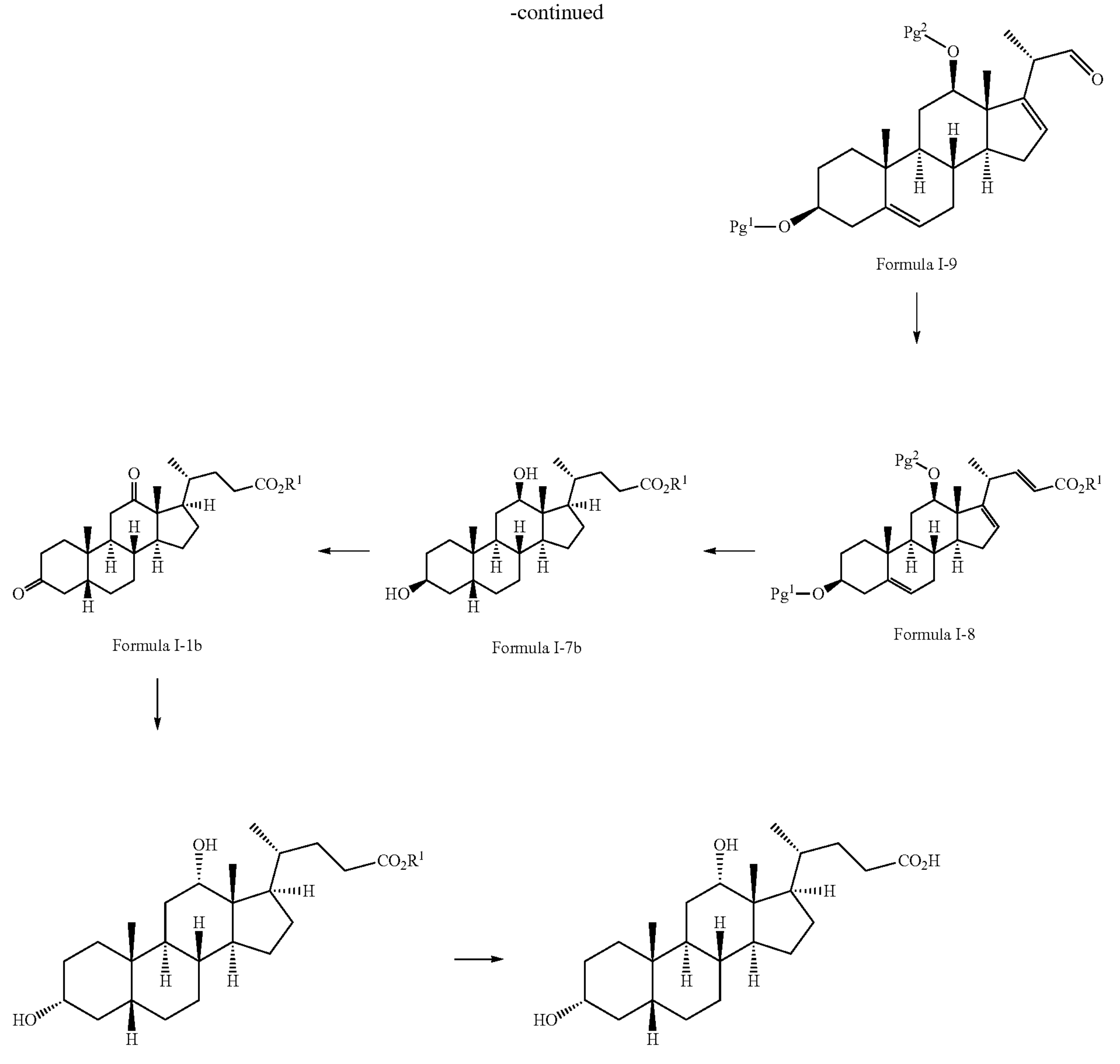

Formula I-9

Formula I-8

Formula I-7b

Formula I-1b

Formula I-12

Deoxycholic acid

In some embodiments, the method of preparing deoxycholic acid, an ester thereof, or a pharmaceutically or cosmetically acceptable salt thereof comprises:

a) reacting a compound of Formula I-10, or a geometric isomer thereof, with formaldehyde or paraformaldehyde in the presence of a Lewis acid Formula I-10

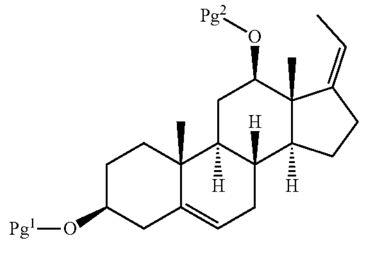

to form a compound of Formula I-11

Formula I-11

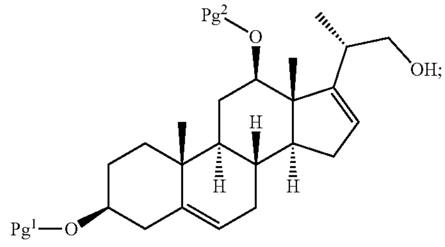

wherein $Pg^1$ and $Pg^2$ are independently a hydroxyl protecting group;

b) oxidizing the compound of Formula I-11 to provide an aldehyde of Formula I-9

Formula I-9

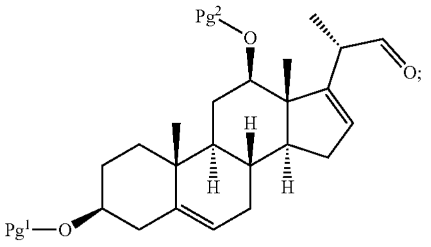

c) reacting the aldehyde of Formula I-9 with an olefin forming reagent to form a compound of Formula I-8, or a geometric isomer thereof, Formula I-8

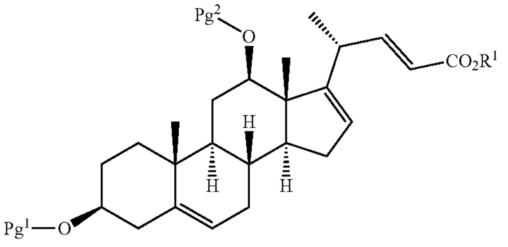

wherein $R^1$ is H or an optionally substituted alkyl group (e.g., an optionally substituted $C_{1-6}$ alkyl);

d) hydrogenating the compound of Formula I-8 and subsequently removing the hydroxyl protecting groups, or deprotecting the compound of Formula I-8 and subsequently hydrogenating the deprotected compound, to provide a diol of Formula I-7b Formula I-7b

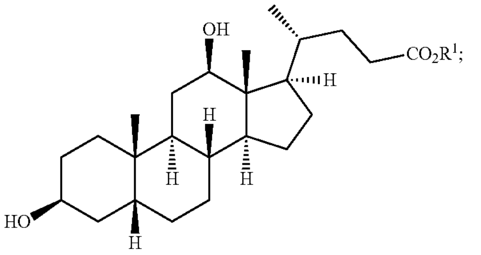

e) oxidizing the diol of Formula I-7b to provide a compound of Formula I-1b,

Formula I-1b

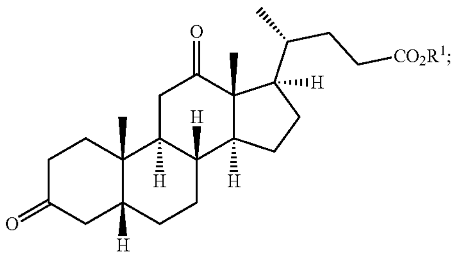

f) contacting the compound of Formula I-1b with a ketone reducing agent to form a compound of Formula I-12

Formula I-12

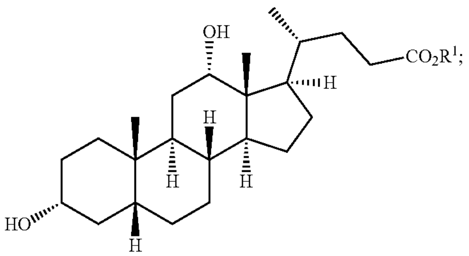

g) optionally, when $R^1$ in Formula I-12 is not H, hydrolyzing the compound of Formula I-12 to provide deoxycholic acid.

The $R^1$ group in Formula I-8, I-7b, I-1b, and I-12 can be the same or different. In some embodiments, $R^1$ group in Formulae I-8, I-7b, I-1b, and I-12 can be the same, for example, as a $C_{1-6}$ alkyl (e.g., methyl or ethyl).

In any of the embodiments described herein for Method 2, the compound of Formula I-1 can be prepared from the compound of Formula I-10 by any of the methods described herein, e.g., Method 1A. In any of the embodiments described herein, the compound of Formula I-10 can be prepared by any of the methods described herein, e.g., Method 1B.

Certain embodiments of the present disclosure are directed to a method of converting the compound of Formula I-1 into the compound of Formula I-12, for example, using a ketone reducing agent. In some embodiments, the ketone reducing agent is a borohydride (such as $NaBH_4$, $NaCNBH_3$, etc.) or a trialkoxyaluminum hydride (e.g., tri-isopropoxyaluminum hydride, tri-tert-butoxyaluminum hydride). In preferred embodiments, the ketone reducing agent is lithium tri-tert-butoxyaluminum hydride ($LiAlH(O\text{-}tBu)_3$).

When $R^1$ is not hydrogen, for example, when $R^1$ is a $C_{1-6}$ alkyl, then to synthesize deoxycholic acid, the method further comprises hydrolyzing the compound of Formula I-12. Thus, in some embodiments, when $R^1$ is not hydrogen, the method comprises hydrolyzing the compound of Formula I-12. Suitable hydrolyzing conditions include those known in the art. For example, the hydrolysis can be effected by reacting the compound of Formula I-12 under acid-mediated (e.g., $BF_3$ mediated), base-mediated (e.g., using an alkali metal hydroxide (e.g., NaOH or LiOH)), or nucleophile-mediated (e.g., $I^-$ mediated) hydrolysis conditions. In preferred embodiments, the hydrolysis comprises contacting the compound of Formula I-12 with an alkali metal hydroxide (e.g., NaOH or LiOH).

In some embodiments, an ester of deoxycholic acid, e.g., the compound of Formula I-12 wherein $R^1$ is an optionally substituted alkyl, is the desired product. For example, in some embodiments, the method is directed to the synthesis of a pharmaceutically or cosmetically acceptable ester of deoxycholic acid. In such embodiments, the preferred reaction conditions for sequences a)-f) are those that no or minimal hydrolysis of the ester (i.e., $—CO_2R^1$) occurs under the respective reaction conditions. However, if desired, the esters of deoxycholic acid can also be prepared by esterification of deoxycholic acid with a desired alcohol.

In some embodiments, a salt of deoxycholic acid is the desired product. For example, in some embodiments, the method is directed to the synthesis of a pharmaceutically or cosmetically acceptable salt of deoxycholic acid. Thus, in some embodiments, the method comprises forming a pharmaceutically or cosmetically acceptable salt of deoxycholic acid, for example, by reacting deoxycholic acid with a suitable base, e.g., metal or ammonium hydroxide (e.g., sodium, potassium, lithium, calcium, magnesium, ammonium, or tetraalkylammonium hydroxide).

Novel Synthetic Intermediates from Methods 1, 1A, 1B and 2

Certain embodiments of the present disclosure are directed to novel synthetic intermediates useful for the preparation of cholic acid and/or deoxycholic acid. In some embodiments, the synthetic intermediate is a compound of Formula II-1, Formula II-2, Formula II-3, or Formula II-4, or a geometric isomer thereof, or a salt thereof:

Formula II-1

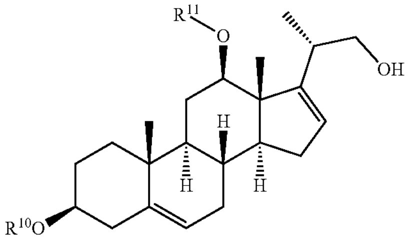

Formula II-2

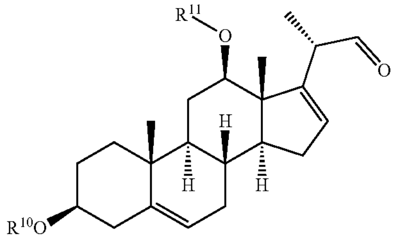

Formula II-3

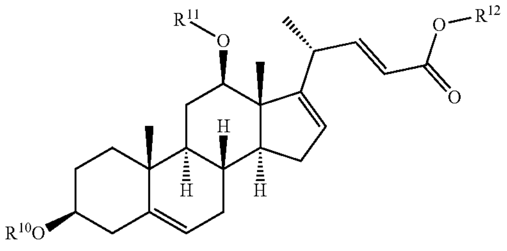

-continued

Formula II-4

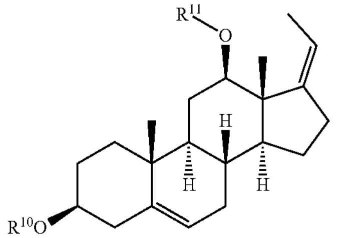

wherein each of $R^{10}$ and $R^{11}$ in each formula is independently H or a hydroxyl protecting group, and $R^{12}$ is H or an optionally substituted alkyl.

In some embodiments, $R^{10}$ and $R^{11}$ are the same. In some embodiments, $R^{10}$ and $R^{11}$ are different. In some embodiments, both $R^{10}$ and $R^{11}$ are H. In some embodiments, one of $R^{10}$ and $R^{11}$ is H and the other of $R^{10}$ and $R^{11}$ is a hydroxyl protecting group (e.g., as described herein, e.g., acetyl). In some embodiments, both $R^{10}$ and $R^{11}$ are hydroxyl protecting groups (e.g., as described herein, e.g., acetyl).

In some embodiments, $R^{12}$ is H. In some embodiments, $R^{12}$ is an optionally substituted alkyl (e.g., optionally substituted $C_{1-6}$ alkyl). In some embodiments, $R^{12}$ is methyl. In some embodiments, $R^{12}$ is ethyl.

In some embodiments, the compound of Formula II-1, Formula II-2, Formula II-3, or Formula II-4 is isolated. In some embodiments, the isolated compound of Formula II-1, Formula II-2, Formula II-3, or Formula II-4 is substantially pure (e.g., at least 80%, at least 85%, at least 90%, at least 95%, or at least 98% pure by weight). In some embodiments, the isolated compound of Formula II-1, Formula II-2, Formula II-3, or Formula II-4 is about 80%, about 85%, about 90%, about 95%, about 98% pure by weight, or any ranges between the specified values. In some embodiments, the isolated compound of Formula II-1, Formula II-2, Formula II-3, or Formula II-4 is substantially free (e.g., less than 5%, less than 3%, less than 2%, less than 1%, less than 0.5%, or less than 0.1% by weight) of other diastereomers and/or geometric isomer. In some embodiments, the isolated compound of Formula II-1, Formula II-2, Formula II-3, or Formula II-4 has about 5%, about 3%, about 2%, about 1%, about 0.5%, about 0.1% by weight, or any ranges between the specified values, of other diastereomers and/or geometric isomer. In some embodiments, the isolated compound of Formula II-1, Formula II-2, Formula II-3, or Formula II-4 is free of (i.e., non-detectable using current analytical tools) other diastereomers and/or geometric isomer.

In some embodiments, the present disclosure also provides a compound of Formula II-5, Formula II-6, Formula II-7, or Formula II-8 having a structure of:

Formula II-5

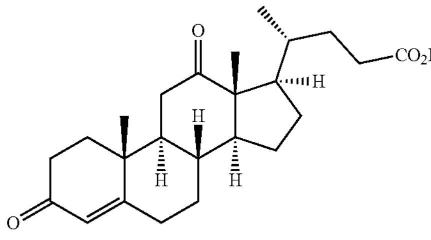

-continued

Formula II-6

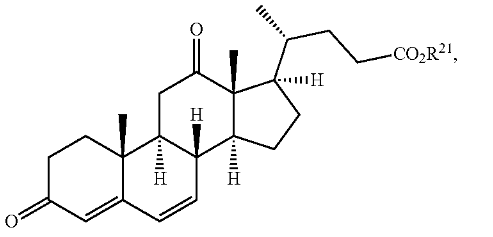

Formula II-7

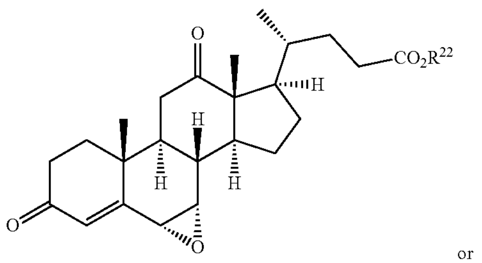

or

Formula II-8

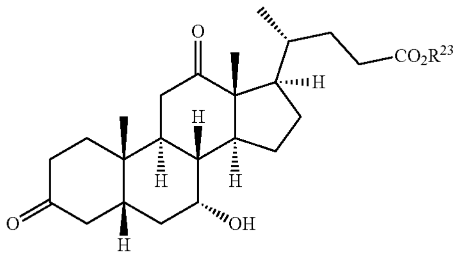

wherein $R^{20}$ and $R^{23}$ are each independently an optionally substituted alkyl, provided that $R^{20}$ and $R^{23}$ are not methyl; and $R^{21}$ and $R^{22}$ are each independently H or an optionally substituted alkyl, or a salt thereof.

In some embodiments, $R^{20}$ is an optionally substituted C2-6 alkyl. In some embodiments, $R^{20}$ is a C2-4 alkyl, e.g., ethyl, isopropyl, etc.

In some embodiments, $R^{23}$ is an optionally substituted C2-6 alkyl. In some embodiments, $R^{23}$ is a C2-4 alkyl, e.g., ethyl, isopropyl, etc.

In some embodiments, $R^{21}$ is H. In some embodiments, $R^{21}$ is an optionally substituted alkyl, e.g., an optionally substituted C1-6 alkyl. In some embodiments, $R^{21}$ is a C2-4 alkyl, e.g., ethyl, isopropyl, etc.

In some embodiments, $R^{22}$ is H. In some embodiments, $R^{22}$ is an optionally substituted alkyl, e.g., an optionally substituted C1-6 alkyl. In some embodiments, $R^{22}$ is a C2-4 alkyl, e.g., ethyl, isopropyl, etc.

In some embodiments, the compound of Formula II-5, Formula II-6, Formula II-7, or Formula II-8 is isolated. In some embodiments, the isolated compound of Formula II-5, Formula II-6, Formula II-7, or Formula II-8 is substantially pure (e.g., at least 80%, at least 85%, at least 90%, at least 95%, or at least 98% pure by weight). In some embodiments, the isolated compound of Formula II-5, Formula II-6, Formula II-7, or Formula II-8 is about 80%, about 85%, about 90%, about 95%, about 98% pure by weight, or any ranges between the specified values. In some embodiments, the isolated compound of Formula II-5, Formula II-6, Formula II-7, or Formula II-8 is substantially free (e.g., less than 5%, less than 3%, less than 2%, less than 1%, less than 0.5%, or less than 0.1% by weight) of other diastereomers and/or geometric isomer. In some embodiments, the isolated compound of Formula II-5, Formula II-6, Formula II-7, or Formula II-8 has about 5%, about 3%, about 2%, about 1%, about 0.5%, about 0.1% by weight, or any ranges between the specified values, of other diastereomers and/or geometric isomer. In some embodiments, the isolated compound of Formula II-5, Formula II-6, Formula II-7, or Formula II-8 is free of (i.e., non-detectable using current analytical tools) other diastereomers and/or geometric isomer.

The compound of any one of Formula II-1 to Formula II-8 can be prepared and purified according to the methods described herein, e.g., the Examples section.

Method 3: Synthesis of Cholic Acid from 3,7-Dioxygenated or 3,7,12-Trioxygenated Steroids As described above, synthesis of cholic acid can also start with 3,7-dioxygenated or 3,7,12-trioxygenated steroids. In some embodiments, the 3,7-dioxygenated or 3,7,12-trioxygenated steroids can be obtained from a 3-hydroxy steroid starting material (e.g., DHEA) by first introducing a 7-hydroxy group followed by introducing a 12-hydroxy group. In various embodiments, the present disclosure also provides a method of preparing cholic acid, an ester thereof, or a pharmaceutically or cosmetically acceptable salt thereof, which comprises converting a 3,7-dioxygenated or 3,7,12-trioxygenated steroid into cholic acid, ester thereof, or a pharmaceutically or cosmetically acceptable salt thereof. For example, in some embodiments, the method comprises a reaction sequence shown in Scheme 5, wherein $R^{30}$, $Pg^{10}$, $Pg^{11}$ and $Pg^{12}$ are defined herein:

Scheme 5
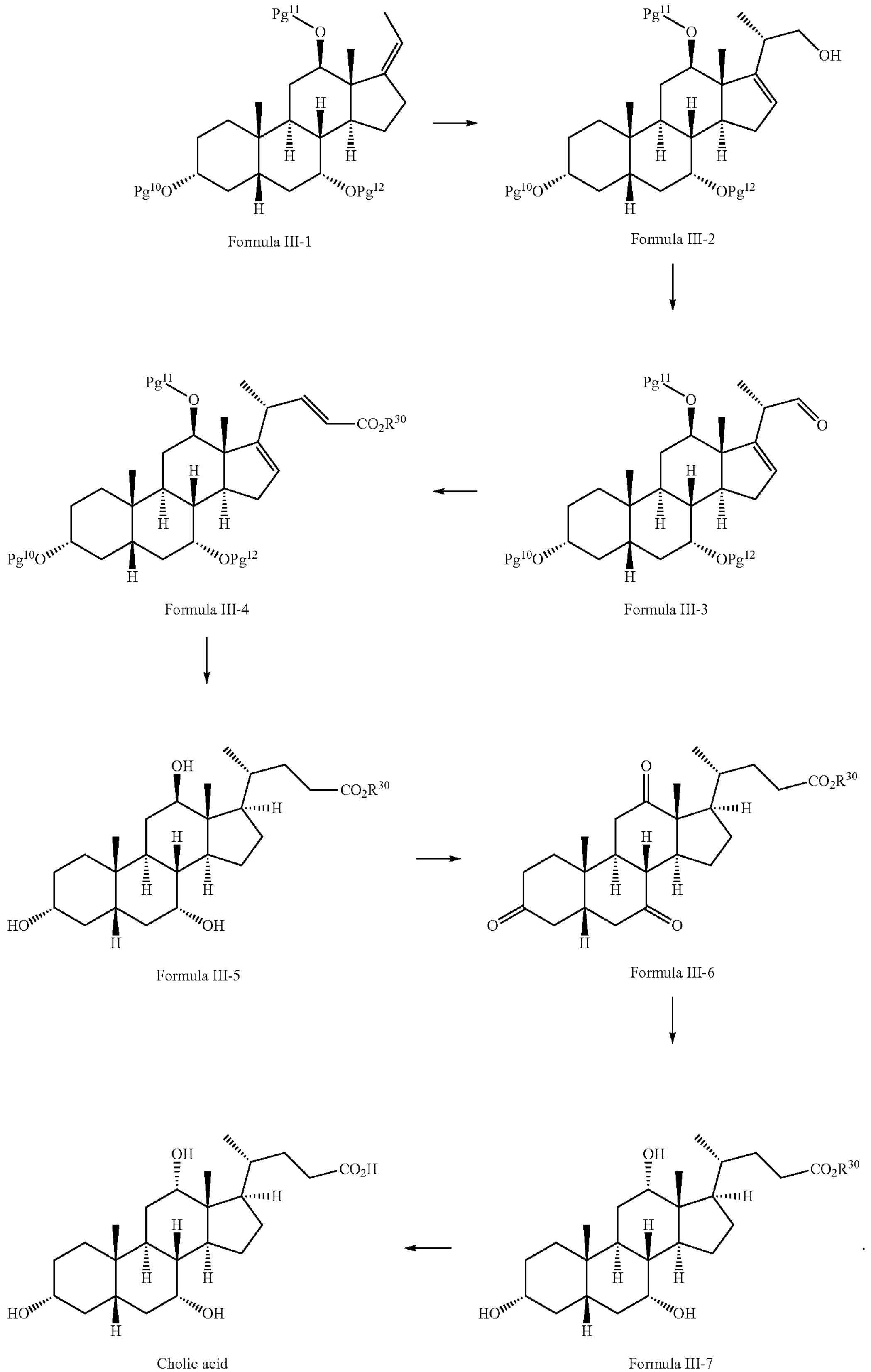
Formula III-1
Formula III-2
Formula III-3
Formula III-4
Formula III-5
Formula III-6
Formula III-7
Cholic acid In some embodiments, the method of preparing cholic acid, an ester thereof, or a pharmaceutically or cosmetically acceptable salt thereof, comprises a) reacting a compound of Formula III-1, or a geometric isomer thereof, with formaldehyde or paraformaldehyde in the presence of a Lewis acid to form a compound of Formula III-2

Formula III-1

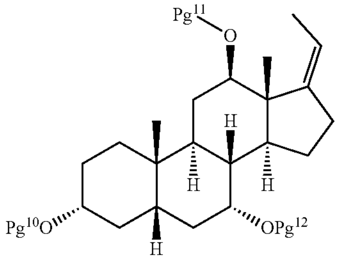

Formula III-2

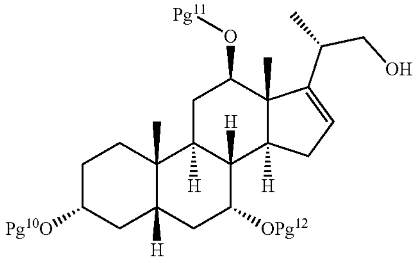

wherein $Pg^{10}$, $Pg^{11}$ and $Pg^{12}$ are each independently a hydroxyl protecting group;

b) oxidizing the compound of Formula III-2 to provide an aldehyde of Formula III-3

Formula III-3

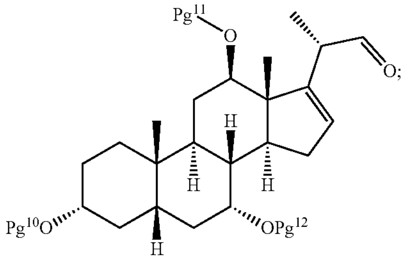

c) reacting the aldehyde of Formula III-3 with an olefin forming reagent to form a compound of Formula III-4, or a geometric isomer thereof, Formula III-4

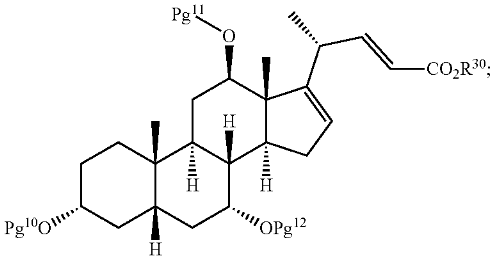

wherein $R^{30}$ is H or an optionally substituted alkyl group;

d) hydrogenating the compound of Formula III-4 with $H_2$ gas in the presence of a metal catalyst and subsequently removing the hydroxyl protecting groups, or removing the hydroxyl protecting groups in Formula III-4 and subsequently hydrogenating the deprotected compound with $H_2$ gas in the presence of a metal catalyst, to provide a triol of Formula III-5

Formula III-5

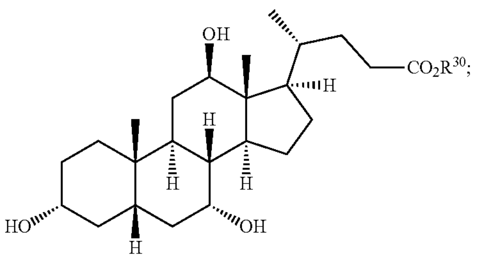

e) oxidizing the triol of Formula III-5 to provide a compound of Formula III-6,

Formula III-6

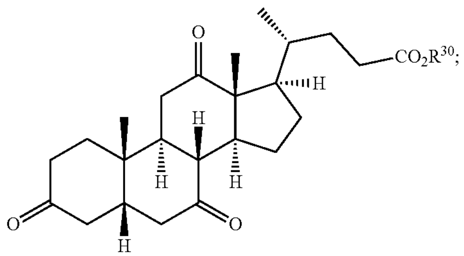

f) contacting the compound of Formula III-6 with a ketone reducing agent to form a compound of Formula III-7

Formula III-7

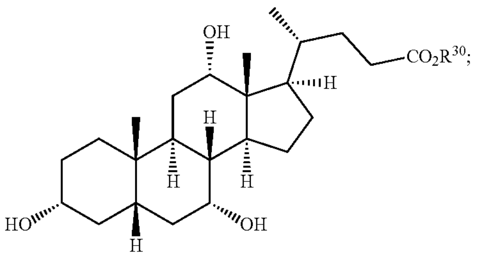

g) optionally, when $R^{30}$ is not H in Formula III-7, hydrolyzing the compound of Formula III-7 to provide cholic acid.

In some embodiments, $R^{30}$ is hydrogen. However, for ease of purification, in preferred embodiments, $R^{30}$ is an alkyl (e.g., methyl or ethyl). In some embodiments, $R^{30}$ can also be an optionally substituted alkyl (e.g., an optionally substituted $C_{1-6}$ alkyl). For example, $R^{30}$ can be an alkyl optionally substituted by 1-3 (e.g., 1, 2, or 3) substituents, wherein the 1-3 substituents are independently a $C_{1-6}$ alkyl, $C_{2-6}$ alkenyl, $C_{2-6}$ alkynyl, $C_{3-6}$ carbocyclyl, 3-6 membered heterocyclyl, 5 or 6 membered heteroaryl, phenyl, a substituted phenyl (e.g., para-methoxyphenyl), hydroxyl, $C_{1-6}$ alkoxy (e.g., a methoxy, ethoxy, etc.), halogen (e.g., F or Cl), or amino optionally substituted by one or two groups independently selected from $C_{1-6}$ alkyl. In preferred embodiments, $R^{30}$ is a $C_{1-6}$ alkyl (e.g., methyl or ethyl). The $R^{30}$ group in Formula III-4 to III-7 can be the same or different. In some embodiments, $R^{30}$ group in Formula III-4 to III-7 can be the same, for example, as a $C_{1-6}$ alkyl (e.g., methyl or ethyl).

$Pg^{10}$, $Pg^{11}$ and $Pg^{12}$ are each independently a hydroxyl protecting group (e.g., as described herein). In some embodiments, $Pg^{10}$, $Pg^{11}$ an $Pg^{12}$ are each acetyl.

Various conditions for effecting the transformations according to Scheme 5 or a), b), c), d), e), f) and g) described above can be used, which are exemplified in embodiments below and in the Examples section. Other useful conditions and details include those known in the art for analogous transformations.

Certain embodiments of the present disclosure are directed to the method of converting the compound of Formula III-1 or a geometric isomer thereof, into the compound of Formula III-2. In some embodiments, the method comprises reacting a compound of Formula III-1 with formaldehyde or paraformaldehyde in the presence of a Lewis acid. Various Lewis acids can be used for this transformation, for example, boron or aluminum based Lewis acids can be used. In some embodiments, the Lewis acid comprises $BF_3$. Other suitable Lewis acids include those known in the art that can facilitate an analogous reaction of an olefin with an aldehyde to provide an alcohol.

Certain embodiments of the present disclosure are directed to the method of oxidizing the compound of Formula III-2 into the compound of Formula III-3. In some embodiments, the oxidizing comprises a Chromium trioxide or chromate based oxidation or variations thereof. In some embodiments, the oxidizing comprises a Swern oxidation or variations thereof. In some embodiments, the oxidizing comprises a hypervalent iodine mediated oxidation. In some embodiments, the oxidizing comprises contacting the compound of Formula I-11 with a suitable oxidizing agent. Various oxidizing agents are suitable. In some embodiments, the oxidizing agent is a Chromium based oxidizing agent, for example, PCC (pyridinium chlorochromate). In some embodiments, the oxidizing agent is a Swern oxidation reagent. Various Swern oxidation reagent systems are known. For example, a typical Swern oxidation can include using a DMSO/oxalyl chloride based system, in which DMSO first reacts with oxalyl chloride to generate a chloro (dimethyl)sulfonium chloride, which then converts an alcohol into an aldehyde or ketone group in the presence of an organic base (e.g., $Et_3N$). Other exemplary useful oxidizing agents include reagents for Swern oxidation or variations thereof which use cyanuric chloride, trifluoroacetic anhydride, carbodiimides, pyridine-sulfur trioxide complex to active DMSO, or use dimethyl sulfide and N-chlorosuccinimide to generate the chlorosulfonium active species. In some embodiments, the oxidizing agent can be 2-iodoxybenzoic acid (IBX) or Dess-Martin periodinane (1,1,1-Triacetoxy-1,1-dihydro-1,2-benziodoxol-3 (1H)-one). Preferably, the reaction and work-up conditions are controlled such that no or minimal epimerization at the C20 position occurs.

Certain embodiments of the present disclosure are directed to the method of converting the compound of Formula III-3 into the compound of Formula III-4 using an olefin forming reagent. Preferably, the reaction and work-up conditions are controlled such that no or minimal epimerization at the C20 position occurs. In some embodiments, the olefin forming reagent comprises a phosphonate substituted acetate:

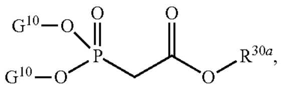

wherein $G^{10}$ at each occurrence and $R^{30a}$ are each independently an optionally substituted alkyl group (e.g., an optionally substituted $C_{1-6}$ alkyl, e.g., ethyl). The phosphonate substituted acetate can be deprotonated to form a phosphonate-stabilized carbanion, which reacts with the aldehyde group in Formula III-3 to form an alpha-beta-unsaturated ester. In some embodiments, the olefin forming reagent is ethyl 2-diethoxyphosphorylacetate. In some embodiments, the olefin forming reagent is a phosphorus ylide (e.g., triphenylcarbethoxymethylenephosphorane) or its precursor. In some embodiments, the olefin forming reagent can comprise an organometallic reagent, such as an organozinc reagent, which reacts with the aldehyde group in Formula III-3 to form a secondary alcohol, which upon dehydration, forms an alpha-beta-unsaturated ester. For example, in some embodiments, the olefin forming reagent comprises a two-carbon Reformatsky reagent:

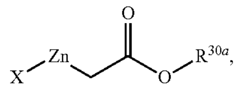

wherein X is halo, such as Cl, Br or I, and $R^{30a}$ is an optionally substituted alkyl group (e.g., an optionally substituted $C_{1-6}$ alkyl, e.g., ethyl). In preferred embodiments, the ester group of the olefin forming reagent (e.g., $R^{30a}$ in either of the phosphonate or the Reformatsky reagent) is the same as $COOR^{30}$ and $R^{30}$ is not H. However, in some embodiments, $R^{30a}$ is different from $R^{30}$, for example, when $R^{30}$ is H. In such embodiments, the method can optionally further include converting the $—CO_2R^{30a}$ in Formula III-4a into $—CO_2R^{30}$ in Formula III-4

Formula III-4a

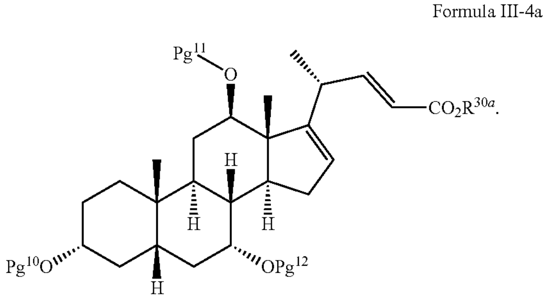

Certain embodiments of the present disclosure are directed to the method of converting the compound of Formula III-4 into the compound of Formula III-5. In some embodiments, the method comprises hydrogenating the compound of Formula III-4 with $H_2$ gas in the presence of a metal catalyst and subsequently removing the hydroxyl protecting groups. In some embodiments, the method comprises removing the hydroxyl protecting groups in Formula III-4 to provide a triol analog and subsequently hydrogenating the deprotected triol analog with $H_2$ gas in the presence of a metal catalyst.

As the olefin double bonds in Formula III-4 or the triol analog of Formula III-4 are hydrogenated during the above transformation to form the triol of Formula III-5, the geometric isomers of the compounds of Formula III-4 or the triol analog of Formula III-4 can also be used. In some embodiments, the method comprises hydrogenating a compound of Formula III-4 or the triol analog of Formula III-4. In some embodiments, the method comprises hydrogenating a geometric isomer of the compound of Formula III-4 or the triol analog of Formula III-4. In some embodiments, the method comprises hydrogenating a mixture of the compound of Formula III-4 or the triol analog of Formula III-4, and its geometric isomers.

Various methods for hydrogenating the compound of Formula III-4 or the triol analog of Formula III-4 can be used. Preferably, the method comprises hydrogenating the compound of Formula III-4 or the triol analog of Formula III-4 with $H_2$ in the presence of a heterogeneous catalyst, for example, a heterogeneous metal catalyst comprising Pd, Ni, Pt, $PtO_2$, Rh, or Ru. In some embodiments, the heterogeneous metal catalyst is Pd/C. The hydrogenation can be conducted at various $H_2$ pressures. In some embodiments, the hydrogenation is conducted at a hydrogen pressure of at or near 1 atm. In some embodiments, the hydrogenation is conducted at a hydrogen pressure of greater than 1 atm (e.g., about 2 atms, about 3 atms, about 5 atms, about 10 atms, about 15 atms, or any ranges between the recited values). In some embodiments, the hydrogenation is conducted at a hydrogen pressure of about 15 psi to about 100 psi (e.g., about 50 psi).

In some embodiments, the compound of Formula III-4 is converted into Formula III-5a by a process comprising hydrogenation, deprotection, and ester hydrolysis, regardless of sequence:

Formula III-5a

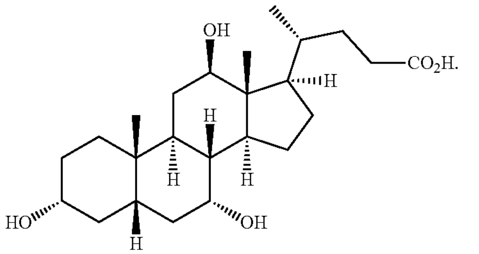

In such embodiments, the method comprises converting Formula III-5a into cholic acid, an ester thereof, or a pharmaceutically or cosmetically acceptable salt thereof, for example, according to the reaction sequence in Scheme 5a:

Scheme 5a

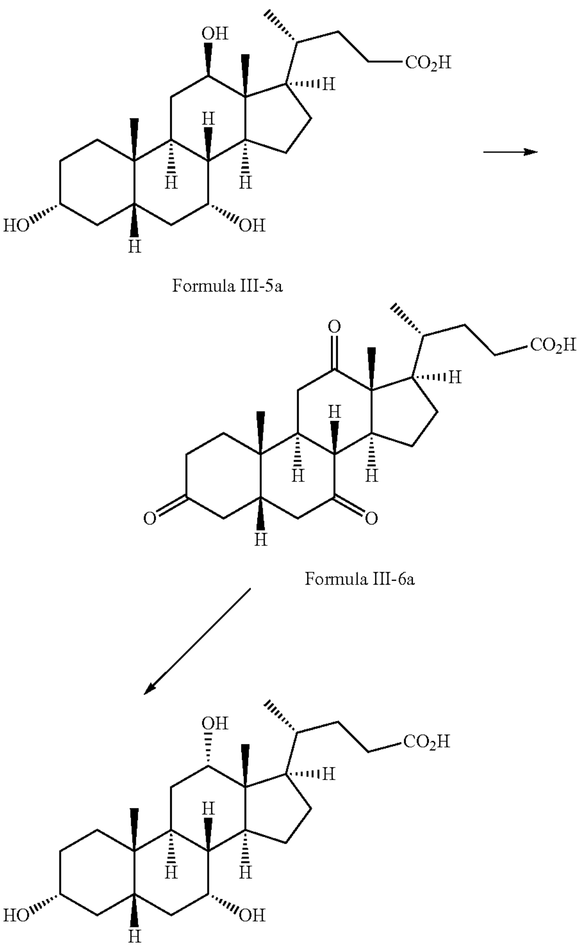

Formula III-5a

Formula III-6a

Cholic acid

Suitable conditions for the transformations in Scheme 5a include those described herein, for example, in the Examples section.

Certain embodiments of the present disclosure are directed to the method of oxidizing the compound of Formula III-5 into the compound of Formula III-6. In some embodiments, the oxidizing comprises a Chromium trioxide or chromate based oxidation or variations thereof. In some embodiments, the oxidizing comprises a Swern oxidation or variations thereof. In some embodiments, the oxidizing comprises a hypervalent iodine mediated oxidation. In some embodiments, the oxidizing comprises contacting the triol of Formula III-5 with a suitable oxidizing agent. In some embodiments, the oxidizing agent is a Chromium based oxidizing agent, for example, Jones reagent (a solution of chromium trioxide in dilute sulfuric acid); PCC (pyridinium chlorochromate), etc. In a preferred embodiment, the oxidizing agent is Jones reagent. In some embodiments, the oxidizing agent is a Swern oxidation reagent. Various Swern oxidation reagent systems are known. For example, a typical Swern oxidation can include using a DMSO/oxalyl chloride based system, in which DMSO first reacts with oxalyl chloride to generate a chloro(dimethyl)sulfonium chloride, which then converts an alcohol into an aldehyde or ketone group in the presence of an organic base (e.g., $Et_3N$). Other exemplary useful oxidizing agents include reagents for Swern oxidation or variations thereof which use cyanuric chloride, trifluoroacetic anhydride, carbodiimides, pyridine-sulfur trioxide complex to active DMSO, or use dimethyl sulfide and N-chlorosuccinimide to generate the chloro-sulfonium active species. In some embodiments, the oxidizing agent can be 2-iodoxybenzoic acid (IBX) or Dess-Martin periodinane (1,1,1-Triacetoxy-1,1-dihydro-1,2-benziodoxol-3 (1H)-one).

Certain embodiments of the present disclosure are directed to the method of converting the compound of Formula III-6 into the compound of Formula III-7, for example, using a ketone reducing agent. In some embodiments, the ketone reducing agent is a borohydride (such as $NaBH_4$, $NaCNBH_3$, etc.) or a trialkoxyaluminum hydride (e.g., tri-isopropoxyaluminum hydride, tri-tert-butoxyaluminum hydride). In preferred embodiments, the ketone reducing agent is lithium tri-tert-butoxyaluminum hydride ($LiAlH(O\text{-}tBu)_3$).

When $R^{30}$ is not hydrogen, for example, when $R^{30}$ is a $C_{1-6}$ alkyl, then to synthesize cholic acid, the method further comprises hydrolyzing the compound of Formula III-7. Thus, in some embodiments, when $R^{30}$ is not hydrogen, the method comprises hydrolyzing the compound of Formula III-7. Suitable hydrolyzing conditions include those known in the art. For example, the hydrolysis can be effected by reacting the compound of Formula III-7 under acid-mediated (e.g., $BF_3$ mediated), base-mediated (e.g., using an alkali metal hydroxide (e.g., NaOH or LiOH)), or nucleophile-mediated (e.g., $I^-$ mediated) hydrolysis conditions. In preferred embodiments, the hydrolysis comprises contacting the compound of Formula III-7 with an alkali metal hydroxide (e.g., NaOH or LiOH).

In some embodiments, an ester of cholic acid, e.g., the compound of Formula III-7 wherein $R^{30}$ is an optionally substituted alkyl, is the desired product. For example, in some embodiments, the method is directed to the synthesis of a pharmaceutically or cosmetically acceptable ester of cholic acid. In such embodiments, the preferred reaction conditions for sequences a)-f) are those that no or minimal hydrolysis of the ester (i.e., $—CO_2R^{30}$) occurs under the respective reaction conditions. However, if desired, the esters of cholic acid can also be prepared by esterification of cholic acid with a desired alcohol.

In some embodiments, a salt of cholic acid is the desired product. For example, in some embodiments, the method is directed to the synthesis of a pharmaceutically or cosmetically acceptable salt of cholic acid. Thus, in some embodiments, the method comprises forming a pharmaceutically or cosmetically acceptable salt of cholic acid, for example, by reacting cholic acid with a suitable base, e.g., metal or ammonium hydroxide (e.g., sodium, potassium, lithium, calcium, magnesium, ammonium, or tetraalkylammonium hydroxide).

The compound of Formula III-1 or geometric isomer thereof used in the methods described hereinabove can be prepared via different methods. For example, in some embodiments, the compound of Formula III-1 or geometric isomer thereof can be synthesized from reacting a compound of Formula III-8 with an olefin forming reagent:

Formula III-8

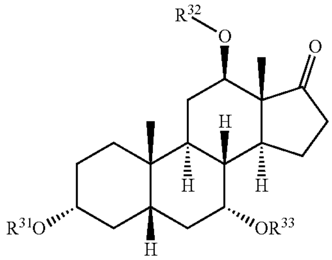

wherein $R^{31}$ is H or $Pg^{10}$; $R^{32}$ is H or $Pg^{11}$; and $R^{33}$ is H or $Pg^{12}$; provided that when one or more of $R^{31}$, $R^{32}$ and $R^{33}$ are H, then a protecting step is carried out after reacting the compound of Formula III-8 with the olefin forming reagent. However, in some embodiments, when one or more of $R^{31}$, $R^{32}$ and $R^{33}$ are H, the protecting step can also be carried out first before reacting with the olefin forming reagent. Various olefin forming reagents are suitable for the transformation. In some embodiments, the olefin forming reagent can be a phosphorous ylide. In some embodiments, the olefin forming reagent can be ethylenetriphenylphosphorane or its precursor ethyltriphenylphosphonium salt. In some embodiments, the olefin forming reagent comprises a two-carbon organometallic reagent (e.g., an organozinc reagent), wherein the 17-ketone of Formula III-8 can be converted into an olefin by first forming an alcoholic intermediate with the organometallic reagent, which is then followed by dehydration.

In some embodiments, $R^{31}$, $R^{32}$ and $R^{33}$ are all H (a compound of Formula III-8a) and the protecting step can be carried out before or after reacting with the olefin forming reagent:

Formula III-8a

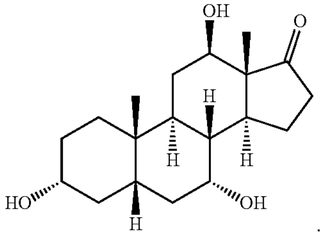

The compound of Formula III-8a can also be served as starting material for the synthesis of the compound of Formula III-8, where at least one of $R^{31}$, $R^{32}$ and $R^{33}$ are not H. For example, in some embodiments, $R^{31}$, $R^{32}$ and $R^{33}$ are each acetyl, the compound of Formula III-8 can be prepared by reacting the compound of Formula III-8a with a suitable acetyl donor (e.g., acetic anhydride).

In any of the embodiments described herein, the compound of Formula III-8a can be prepared by the methods described herein, e.g., Method 3A below. In any of the embodiments described herein, the compound of Formula III-8a can also be a synthetic material free of any animal derived impurities.

Method 3A: Synthesis of the Compound of Formula III-8a from DHEA Via 3,7-Dioxygenated Steroids Certain embodiments of the present disclosure are directed to a method of preparing a compound of Formula III-8a. In some embodiments, the method comprises obtaining the compound of Formula III-8a from DHEA as exemplified in Scheme 6:

Scheme 6

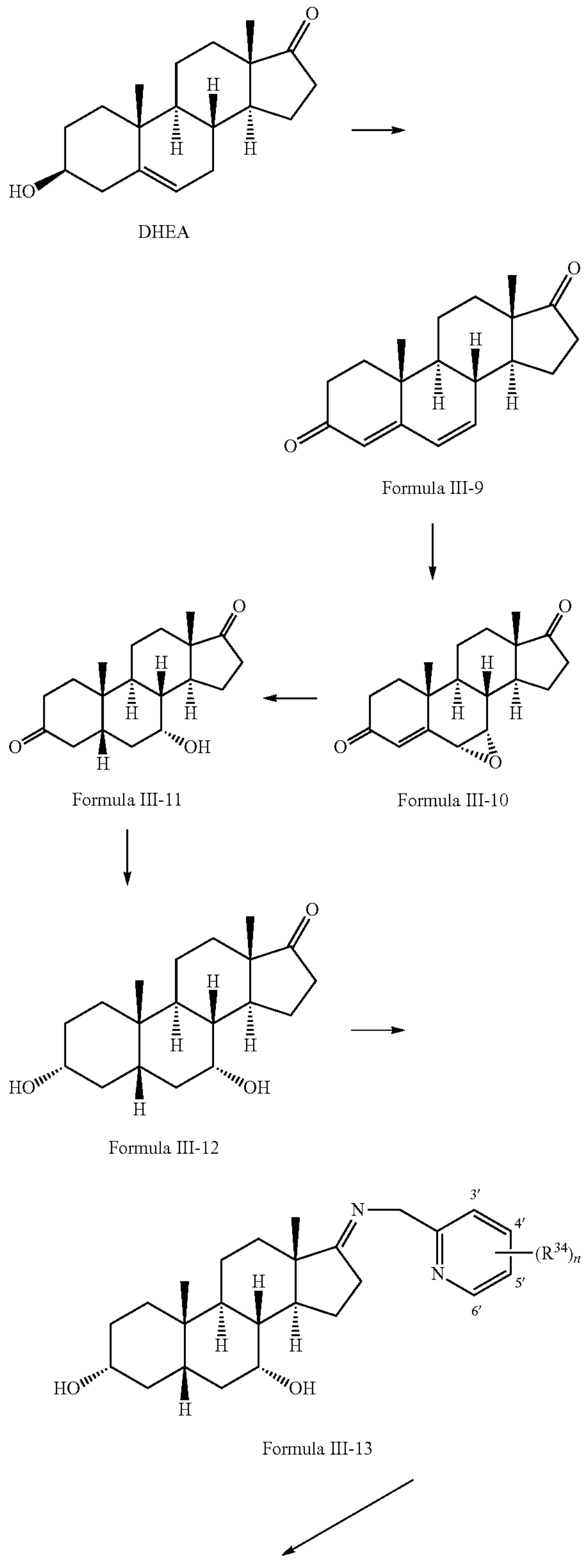

DHEA

Formula III-9

Formula III-11

Formula III-10

Formula III-12

Formula III-13

-continued

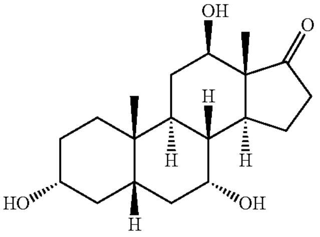

Formula III-8a wherein n is 0, 1 or 2, and $R^{34}$ is $C_{1-6}$ alkyl.

In some embodiments, the method comprises:

a) oxidizing dehydroepiandrosterone (DHEA) into a compound of Formula III-9

DHEA

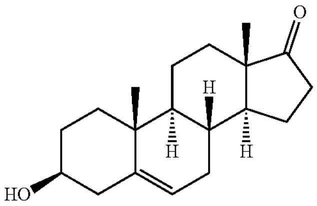

Formula III-9

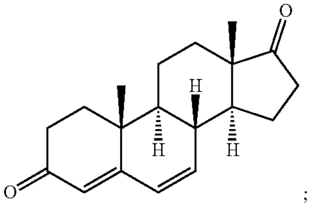

;

b) reacting the compound of Formula III-9 with an epoxide forming reagent to form an epoxide of Formula III-10

Formula III-10

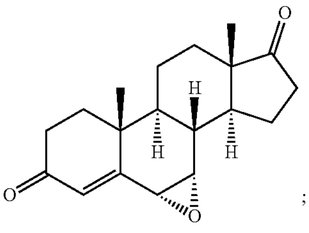

;

c) reducing the epoxide of Formula III-10 under hydrogenation condition to form a diketone of Formula III-11

Formula III-11

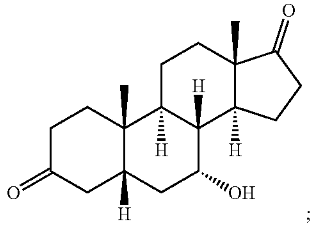

;

d) contacting the diketone of Formula III-11 with a ketone reducing agent to form a compound of Formula III-12

Formula III-12

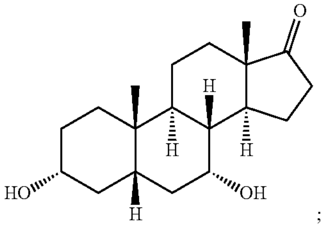

;

e) reacting the compound of Formula III-12 with an amine to form an imine of Formula III-13

Formula III-13

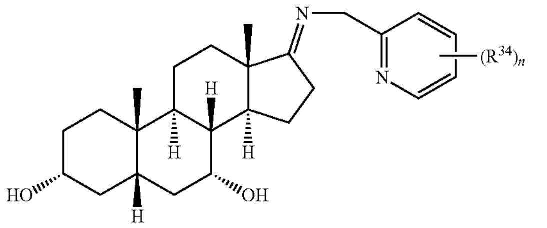

wherein n is 0, 1 or 2, and $R^{34}$ is $C_{1-6}$ alkyl; and f) oxidizing the imine of Formula III-13 with $O_2$ in the presence of a copper salt to form the compound of Formula III-8a.

Various conditions are suitable for the transformations described in scheme 6 or a)-f) above, which are exemplified in the embodiments below and in the Examples section. Other useful conditions and details include those known in the art for analogous transformations.

For example, DHEA can be converted into the compound of Formula III-9 through oxidation. In some embodiments, the oxidation can be carried out with a benzoquinone based oxidizing agent (e.g., DDQ or chloranil) and an amine oxide (e.g., TEMPO (2,2,6,6-tetramethylpiperidin-1-yl)oxidanyl)).

The compound of Formula III-9 can be converted into the compound of Formula III-10 using an epoxide forming reagent. In some embodiments, the epoxide forming reagent is a peroxycarboxylic acid. In some embodiments, the epoxide forming reagent is meta-chloroperoxybenzoic acid. Other suitable epoxide forming reagents include those known in the art that can selectively produce an epoxide at the 6,7 positions with the olefin at the 4,5 positions intact.

In some embodiments, conversion of the compound of Formula III-10 into the compound of Formula III-11 can be achieved through a hydrogenation reaction. For example, in some embodiments, the method comprises hydrogenating the compound of Formula III-10 with $H_2$ under the catalysis of a heterogeneous catalyst, for example, a heterogeneous metal catalyst comprising Pd, Ni, Pt, $PtO_2$, Rh, or Ru. In some embodiments, the heterogeneous metal catalyst is Pd/C. The hydrogenation can be conducted at various $H_2$ pressures. In some embodiments, the hydrogenation is conducted at a hydrogen pressure of at or near 1 atm. In some embodiments, the hydrogenation is conducted at a hydrogen pressure of greater than 1 atm (e.g., about 2 atms, about 3 atms, about 5 atms, about 10 atms, about 15 atms, or any ranges between the recited values). In some embodiments, the hydrogenation is conducted at a hydrogen pressure of about 15 psi to about 100 psi (e.g., about 50 psi).

In some embodiments, conversion of the compound of Formula III-11 into the compound of Formula III-12 can be achieved through a reduction reaction. Various ketone reducing agents can be used to effect this transformation. In some embodiments, the ketone reducing agent is a borohydride (such as $NaBH_4$, $NaCNBH_3$, etc.) or a trialkoxyaluminum hydride (e.g., tri-isopropoxyaluminum hydride, tri-tert-butoxyaluminum hydride). In preferred embodiments, the ketone reducing agent is lithium tri-tert-butoxyaluminum hydride (LiAl $H(O\text{-}tBu)_3$).

In some embodiments, the 3,7-dihydoxy compound of Formula III-12 can be converted into the imine of Formula III-13 with a corresponding amine. Various imines of Formula III-13 are suitable for the methods described herein. In some embodiments, the pyridine ring in Formula III-13 is unsubstituted, i.e., n is 0. In some embodiments, the pyridine ring in Formula III-13 is substituted by one or two C1-6 alkyl groups. For example, in some embodiments, the pyridine ring in Formula III-13 is substituted at the 4'-position by a methyl group. The imine formation is generally catalyzed by an acid, for example, para-toluenesulfonic acid.

Suitable copper salt for the transformation of the compound of Formula III-13 into the compound of Formula III-8a includes any of those known in the art for analogous transformations. In some embodiments, the copper salt is a copper (II) salt such as $Cu(OTf)_2$. In some embodiments, the copper salt is a copper (I) salt such as $Cu(MeCN)_4PF_6$.

The reduction of the compound of Formula III-11, the imine formation of the compound of Formula III-12, and the copper mediated oxidation of the imine of Formula III-13 do not require the hydroxyl group to be protected or to be a free hydroxyl group. Thus, in some embodiments, one or more of Formula III-11, Formula III-12, and Formula III-13 can be protected and used for the synthesis of either the compound of Formula III-8a or Formula III-8, with appropriate protection or deprotection depending on the target product. In some embodiments, the present disclosure provides a method of preparing a compound of Formula III-8 according to scheme 7, wherein $R^{31}$, $R^{32}$, $R^{33}$, and $R^{34}$ are as described hereinabove:

Scheme 7

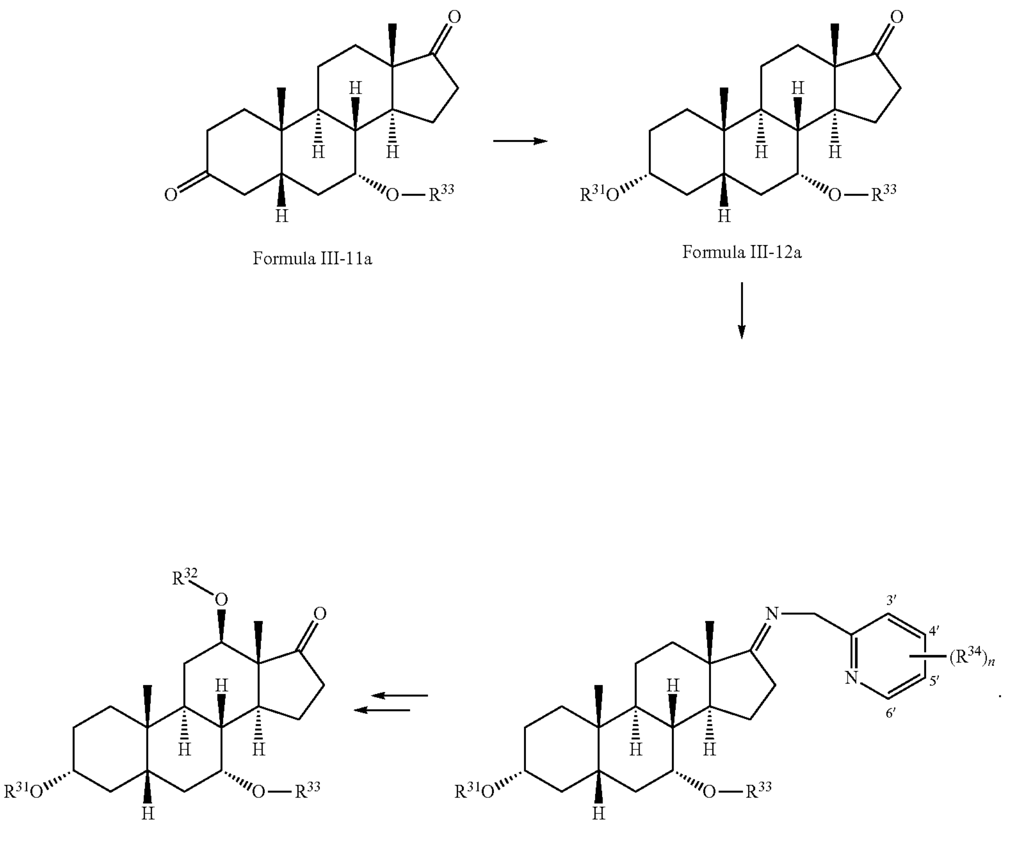

Formula III-11a

Formula III-12a

Formula III-8

Formula III-13a

The transformations described in scheme 7 are similar to those described in Scheme 6, except that $R^{33}$ in Formula III-11a, Formula III-12a, and Formula III-13a, and $R^{31}$ in Formula III-12a, and Formula III-13a, can be hydrogen or a hydroxyl protecting group as described herein.

Method 4: Synthesis of Chenodeoxycholic Acid from 3,7-Dioxygenated Steroids

Chenodeoxycholic acid (CDCA) contains two hydroxyl groups at the 3,7-positions, which can be prepared by an intermediate such as a compound of Formula III-12 or a hydroxyl-protected derivative thereof. In some embodiments, the present disclosure is directed to a method of preparing chenodeoxycholic acid, an ester thereof, or a pharmaceutically or cosmetically acceptable salt thereof from a 3,7-dioxygenated steroid. In some embodiments, the method comprises a reaction sequence according to Scheme 8, wherein $Pg^{20}$ and $Pg^{21}$ are each independently a hydroxyl protecting group and $R^{40}$ is H or an optionally substituted alkyl group:

Scheme 8

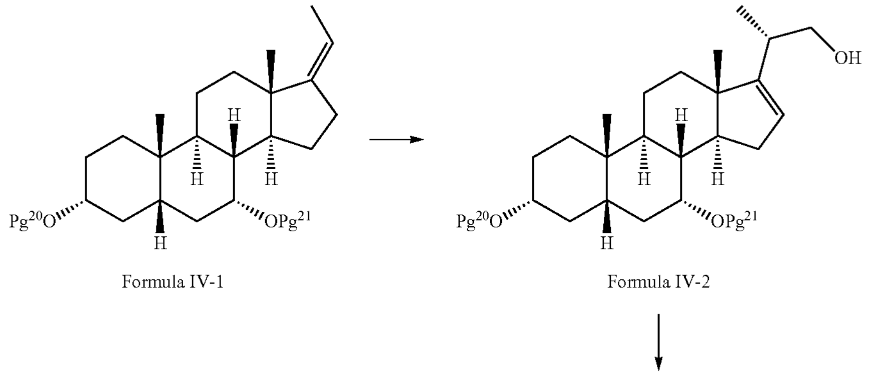

Formula IV-1

Formula IV-2

-continued

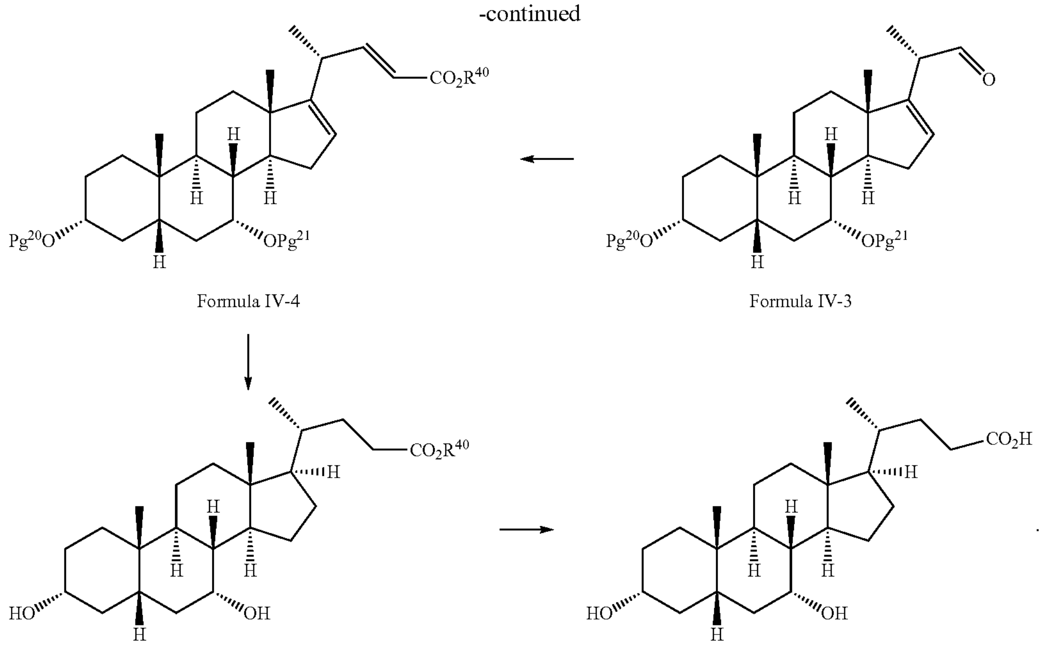

Formula IV-4

Formula IV-3

Formula IV-5 chenodeoxycholic acid

In some embodiments, the method comprises:

a) reacting a compound of Formula IV-1, or a geometric isomer thereof, with formaldehyde or paraformaldehyde in the presence of a Lewis acid to form a compound of Formula IV-2

Formula IV-1

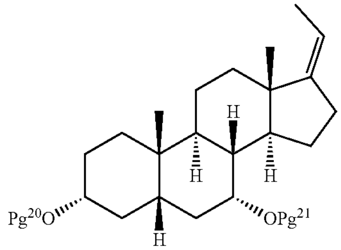

Formula IV-2

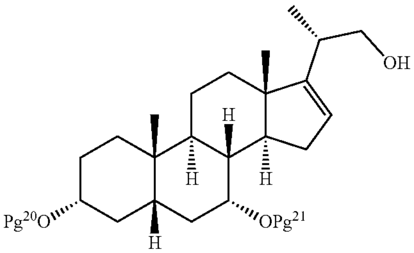

wherein $Pg^{20}$ and $Pg^{21}$ are each independently a hydroxyl protecting group;

b) oxidizing the compound of Formula IV-2 to provide an aldehyde of Formula IV-3

Formula IV-3

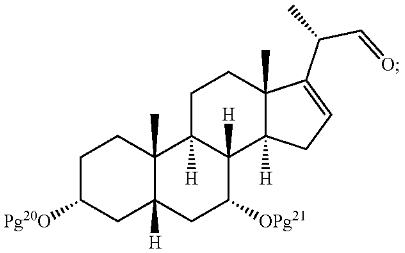

c) reacting the aldehyde of Formula IV-3 with an olefin forming reagent to form a compound of Formula IV-4, or a geometric isomer thereof, Formula IV-4

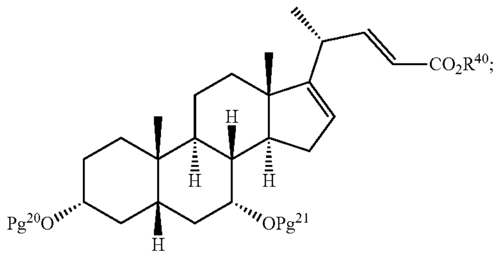

wherein $R^{40}$ is H or an optionally substituted alkyl group;

d) hydrogenating the compound of Formula IV-4 with $H_2$ gas in the presence of a metal catalyst and subsequently removing the hydroxyl protecting groups, or removing the hydroxyl protecting groups of Formula IV-4 and subsequently hydrogenating the deprotected compound with $H_2$ gas in the presence of a metal catalyst, to provide a diol of Formula IV-5

Formula IV-5

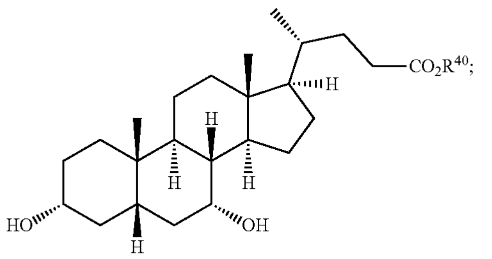

and e) optionally, when $R^{40}$ is not H in Formula IV-5, hydrolyzing the compound of Formula IV-5 into chenodeoxycholic acid.

Suitable hydroxyl protecting groups for $Pg^{20}$ and $Pg^{21}$ include any of those known in the art, for example, those described herein. In some embodiments, $Pg^{20}$ and $Pg^{21}$ are the same. In some embodiments, $Pg^{20}$ and $Pg^{21}$ are different. In preferred embodiments, both $Pg^{20}$ and $Pg^{21}$ are hydroxyl protecting group that forms an ester with the hydroxyl group, for example, both $Pg^{20}$ and $Pg^{21}$ are acetyl.

In some embodiments, $R^{40}$ is hydrogen. However, for ease of purification, in preferred embodiments, $R^{40}$ is a $C_{1-6}$ alkyl (e.g., methyl or ethyl). In some embodiments, $R^{40}$ can also be an optionally substituted alkyl (e.g., an optionally substituted $C_{1-6}$ alkyl). For example, $R^{40}$ can be an alkyl optionally substituted by 1-3 (e.g., 1, 2, or 3) substituents, wherein the 1-3 substituents are independently a $C_{1-6}$ alkyl, $C_{2-6}$ alkenyl, $C_{2-6}$ alkynyl, $C_{3-6}$ carbocyclyl, 3-6 membered heterocyclyl, 5 or 6 membered heteroaryl, phenyl, a substituted phenyl (e.g., para-methoxyphenyl), hydroxyl, $C_{1-6}$ alkoxy (e.g., a methoxy, ethoxy, etc.), halogen (e.g., F or Cl), or amino optionally substituted by one or two groups independently selected from $C_{1-6}$ alkyl. In preferred embodiments, $R^{40}$ is a $C_{1-6}$ alkyl (e.g., methyl or ethyl). $R^{40}$ group in Formulae IV-4 and IV-5 can be the same or different. In some embodiments, $R^{40}$ group in Formulae IV-4 and IV-5 can be the same, e.g., as a $C_{1-6}$ alkyl (e.g., methyl or ethyl).

Various conditions for effecting the transformations in Scheme 8 and a), b), c), d) and e) in Method 4 can be used, which are exemplified in the embodiments below and in the Examples section. Other useful conditions and details include those known in the art for analogous transformations.

Certain embodiments of the present disclosure are directed to a method of converting the compound of Formula IV-1 into the compound of Formula IV-2. In some embodiments, the conversion comprises reacting a compound of Formula IV-1 or a geometric isomer thereof, with formaldehyde or paraformaldehyde in the presence of a Lewis acid. Various Lewis acids can be used for this transformation, for example, boron or aluminum based Lewis acids can be used. In some embodiments, the Lewis acid comprises $BF_3$. Other suitable Lewis acids include those known in the art that can facilitate an analogous reaction of an olefin with an aldehyde to provide an alcohol.

Certain embodiments of the present disclosure are directed to a method of oxidizing the compound of Formula IV-2 into the compound of Formula IV-3 by using an oxidizing agent. In some embodiments, the oxidizing comprises a Chromium trioxide or chromate based oxidation or variations thereof. In some embodiments, the oxidizing comprises a Swern oxidation or variations thereof. In some embodiments, the oxidizing comprises a hypervalent iodine mediated oxidation. In some embodiments, the oxidizing comprises contacting the compound of Formula IV-2 with a suitable oxidizing agent. In some embodiments, the oxidizing agent is a Chromium based oxidizing agent, for example, PCC (pyridinium chlorochromate). In some embodiments, the oxidizing agent is a Swern oxidation reagent. Various Swern oxidation reagent systems are known. For example, a typical Swern oxidation can include using a DMSO/oxalyl chloride based system, in which DMSO first reacts with oxalyl chloride to generate a chloro(dimethyl)sulfonium chloride, which then converts an alcohol into an aldehyde or ketone group in the presence of an organic base (e.g., $Et_3N$). Other exemplary useful oxidizing agents include reagents for Swern oxidation or variations thereof, which use cyanuric chloride, trifluoroacetic anhydride, carbodiimides, pyridine-sulfur trioxide complex to active DMSO, or use dimethyl sulfide and N-chlorosuccinimide to generate the chlorosulfonium active species. In some embodiments, the oxidizing agent can be 2-iodoxybenzoic acid (IBX) or Dess-Martin periodinane (1,1,1-Triacetoxy-1,1-dihydro-1,2-benziodoxol-3 (1H)-one). Preferably, the reaction and work-up conditions are controlled such that no or minimal epimerization at the C20 position occurs.

Certain embodiments of the present disclosure are directed to a method of converting the compound of Formula IV-3 into the compound of Formula IV-4 by using an olefin forming reagent. Various olefin forming reagents are suitable for this transformation. Preferably, the reaction and work-up conditions are controlled such that no or minimal epimerization at the C20 position occurs. In some embodiments, the olefin forming reagent comprises a phosphonate substituted acetate:

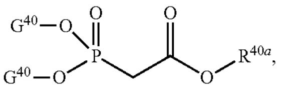

wherein $G^{40}$ at each occurrence and $R^{40a}$ are each independently an optionally substituted alkyl group (e.g., an optionally substituted $C_{1-6}$ alkyl, e.g., ethyl). The phosphonate substituted acetate can be deprotonated to form a phosphonate-stabilized carbanion, which reacts with the aldehyde group in Formula IV-3 to form an alpha-beta-unsaturated ester. In some embodiments, the olefin forming reagent is ethyl 2-diethoxyphosphorylacetate. In some embodiments, the olefin forming reagent is a phosphorus ylide (e.g., triphenylcarbethoxymethylenephosphorane) or its precursor. In some embodiments, the olefin forming reagent can comprise an organometallic reagent, such as an organozinc reagent, which reacts with the aldehyde group in Formula IV-3 to form a secondary alcohol, which upon dehydration, forms an alpha-beta-unsaturated ester. For example, in some embodiments, the olefin forming reagent comprises a two-carbon Reformatsky reagent:

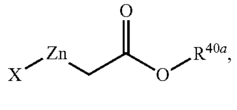

wherein X is halo, such as Cl, Br or I, and $R^{40a}$ is an optionally substituted alkyl group (e.g., an optionally substituted $C_{1-6}$ alkyl, e.g., ethyl). In preferred embodiments, the ester group of the olefin forming reagent (e.g., $R^{40a}$ in either of the phosphonate or the Reformatsky reagent) is the same as $COOR^{40}$ and $R^{40}$ is not H. However, in some embodiments, $R^{40a}$ is different from $R^{40}$, for example, when $R^{40}$ is H. In such embodiments, the method can optionally further include converting the $—CO_2R^{40a}$ in Formula IV-4a into $—CO_2R^{40}$ in Formula IV-4

Formula IV-4a

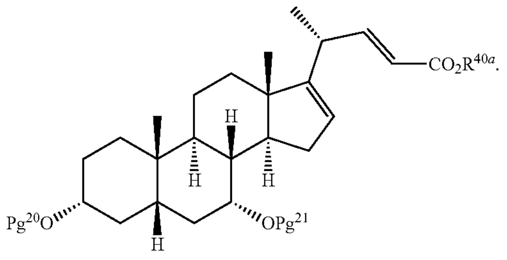

Certain embodiments of the present disclosure are directed to a method of converting the compound of Formula IV-4 into the compound of Formula IV-5. In some embodiments, the diol of Formula IV-5 is synthesized by hydrogenating the compound of Formula IV-4 followed by removing the hydroxyl protecting groups. In some embodiments, the diol of Formula IV-5 is synthesized by removing the hydroxyl protecting groups of the compound of Formula IV-4 followed by hydrogenation of the double bonds. As the olefin double bonds in Formula IV-4 are hydrogenated during the above transformation to form the diol of Formula IV-5, the geometric isomers of the compounds of Formula IV-4 can also be used. In some embodiments, the method comprises hydrogenating the compound of Formula IV-4. In some embodiments, the method comprises hydrogenating a geometric isomer of the compound of Formula IV-4. In some embodiments, the method comprises hydrogenating a mixture of the compound of Formula IV-4, and its geometric isomers.

Various methods for hydrogenating the compound of Formula IV-4 can be used. Preferably, the method comprises hydrogenating the compound of Formula IV-4 with $H_2$ in the presence of a heterogeneous catalyst, for example, a heterogeneous metal catalyst comprising Pd, Ni, Pt, $PtO_2$, Rh, or Ru. In some embodiments, the heterogeneous metal catalyst is Pd/C. The hydrogenation can be conducted at various $H_2$ pressures. In some embodiments, the hydrogenation is conducted at a hydrogen pressure of at or near 1 atm. In some embodiments, the hydrogenation is conducted at a hydrogen pressure of greater than 1 atm (e.g., about 2 atms, about 3 atms, about 5 atms, about 10 atms, about 15 atms, or any ranges between the recited values). In some embodiments, the hydrogenation is conducted at a hydrogen pressure of about 15 psi to about 100 psi (e.g., about 50 psi).

Various methods can be used for the synthesis of the compound of Formula IV-1 or a geometric isomer thereof. In some embodiments, the compound of Formula IV-1 or a geometric isomer thereof is obtained from reacting a compound of Formula IV-6 with an olefin forming reagent Formula IV-6

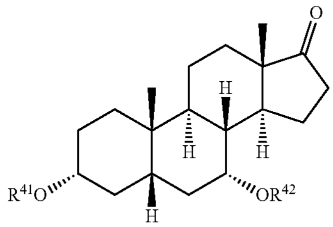

wherein $R^{41}$ is H or P $Pg^{20}$; $R^{42}$ is H or $Pg^{21}$; provided that when one or both of $R^{41}$ and $R^{42}$ are H, then a protecting step is followed after reacting the compound of Formula IV-6 with the olefin forming reagent. In some embodiments, the olefin forming reagent can be a phosphorous ylide. In some embodiments, the olefin forming reagent can be ethylenetriphenylphosphorane or its precursor ethyltriphenylphosphonium salt. In some embodiments, the olefin forming reagent comprises a two-carbon organometallic reagent (e.g., an organozinc reagent), wherein the 17-ketone of Formula IV-6 can be converted into an olefin by first forming an alcoholic intermediate with the organometallic reagent, which is then followed by dehydration.

When $R^{40}$ is not hydrogen, for example, when $R^{40}$ is a $C_{1-6}$ alkyl, then to synthesize chenodeoxycholic acid, the method further comprises hydrolyzing the compound of Formula IV-5. Thus, in some embodiments, when $R^{40}$ is not hydrogen, the method comprises hydrolyzing the compound of Formula IV-5. Suitable hydrolyzing conditions include those known in the art. For example, the hydrolysis can be effected by reacting the compound of Formula IV-5 under acid-mediated (e.g., $BF_3$ mediated), base-mediated (e.g., using an alkali metal hydroxide (e.g., NaOH or LiOH)), or nucleophile-mediated (e.g., $I^-$ mediated) hydrolysis conditions. In preferred embodiments, the hydrolysis comprises contacting the compound of Formula IV-5 with an alkali metal hydroxide (e.g., NaOH or LiOH).

In some embodiments, an ester of chenodeoxycholic acid, e.g., the compound of Formula IV-5, wherein $R^{40}$ is an optionally substituted alkyl, is the desired product. For example, in some embodiments, the method is directed to the synthesis of a pharmaceutically or cosmetically acceptable ester of chenodeoxycholic acid. In such embodiments, the preferred reaction conditions for sequences a)-d) are those that no or minimal hydrolysis of the ester (i.e., $—CO_2R^{40}$) occurs under the respective reaction conditions. However, if desired, the esters of chenodeoxycholic acid can also be prepared by esterification of chenodeoxycholic acid with a desired alcohol.

In some embodiments, a salt of chenodeoxycholic acid is the desired product. For example, in some embodiments, the method is directed to the synthesis of a pharmaceutically or cosmetically acceptable salt of chenodeoxycholic acid. Thus, in some embodiments, the method comprises forming a pharmaceutically or cosmetically acceptable salt of chenodeoxycholic acid, for example, by reacting chenodeoxycholic acid with a suitable base, e.g., metal or ammonium hydroxide (e.g., sodium, potassium, lithium, calcium, magnesium, ammonium, or tetraalkylammonium hydroxide).

Compounds of Formula IV-6 can be readily available from either Formula III-11 or Formula III-12. For example, when both $R^{41}$ and $R^{42}$ are H, Formula IV-6 is the same as Formula III-12. When both $R^{41}$ and $R^{42}$ are the same hydroxyl protecting group, a double protection of Formula III-12 with an appropriate protecting group can provide the compound of Formula IV-6. Further, when $R^{41}$ and $R^{42}$ are different, the compound of Formula IV-6 can be provided through the compound of Formula III-11 by using a combination of protection/deprotection and reduction steps, so as to differentiate the two 3- and 7-hydroxyl groups regardless of their intrinsic reactivity.

In any of the embodiments described herein for Method 4, the compound of Formula IV-6 can be prepared from the compound of Formula III-11 or Formula III-12, which in turn can be prepared by any of the methods described herein, e.g., Method 3. In any of the embodiments described herein, the compound of Formula III-11 or Formula III-12 can also be a synthetic material free of any animal derived impurities.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in "Protective Groups in Organic Synthesis", 4$^{th}$ ed. P. G. M. Wuts; T. W. Greene, John Wiley, 2007, and references cited therein. The reagents for the reactions described herein are generally known compounds or can be prepared by known procedures or obvious modifications thereof. For example, many of the reagents are available from commercial suppliers such as Aldrich Chemical Co. (Milwaukee, Wis., USA), Bachem (Torrance, Calif., USA), Emka-Chem or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplemental (Elsevier Science Publishers, 1989), Organic Reactions, Volumes 1-40 (John Wiley and Sons, 1991), March's Advanced Organic Chemistry, (Wiley, 7$^{th}$ Edition), and Larock's Comprehensive Organic Transformations (Wiley-VCH, 1999).

Novel Synthetic Intermediates from Methods 3 and 4

Certain embodiments of the present disclosure are directed to useful novel synthetic intermediates, for example, for the preparation of cholic acid and/or chenodeoxycholic acid. In some embodiments, the synthetic intermediate is a compound of Formula V-1, Formula V-2, Formula V-3, or Formula V-4, or a geometric isomer thereof, or a salt thereof:

Formula V-1

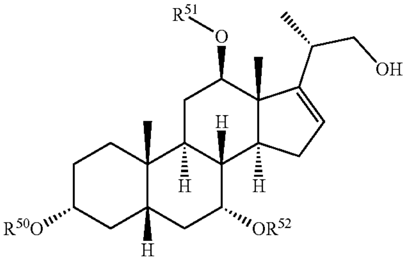

-continued

Formula V-2

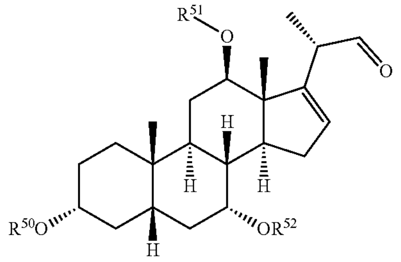

Formula V-3

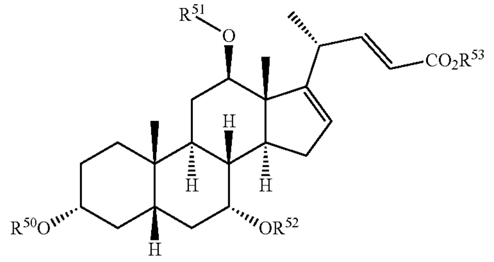

Formula V-4

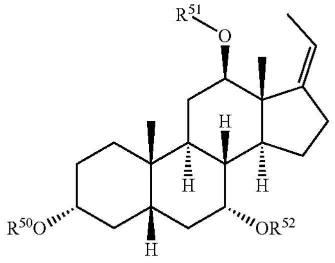

wherein each of $R^{50}$, $R^{51}$, and $R^{52}$ is independently H or a hydroxyl protecting group, and $R^{53}$ is H or an optionally substituted alkyl.

$R^{50}$, $R^{51}$, and $R^{52}$ in each of Formula V-1, Formula V-2, Formula V-3, and Formula V-4 can be independently selected. In some embodiments, $R^{50}$, $R^{51}$, and $R^{52}$ are each H. In some embodiments, $R^{50}$, $R^{51}$, and $R^{52}$ are each independently a hydroxyl protecting group (e.g., as described herein). In some embodiments, $R^{50}$, $R^{51}$, and $R^{52}$ are the same hydroxyl protecting group. In some embodiments, at least two of $R^{50}$, $R^{51}$, and $R^{52}$ are the same hydroxyl protecting group. In some embodiments, at least two of $R^{50}$, $R^{51}$, and $R^{52}$ are different. For example, one of $R^{50}$, $R^{51}$, and $R^{52}$ can be hydrogen and the other two of $R^{50}$, $R^{51}$, and $R^{52}$ can be the same or different hydroxyl protecting group. Suitable hydroxyl protecting groups include any of those described herein. In some embodiments, the hydroxyl protecting group is acetyl.

Some embodiments are directed to the compound of Formula V-3, a geometric isomer thereof, or a salt thereof. $R^{50}$, $R^{51}$, and $R^{52}$ in Formula V-3 are described hereinabove. In some embodiments, $R^{53}$ is H. In some embodiments, $R^{53}$ is an optionally substituted alkyl (e.g., optionally substituted $C_{1-6}$ alkyl). In some embodiments, $R^{53}$ is methyl. In some embodiments, $R^{53}$ is ethyl.

In some embodiments, the compound of Formula V-1, Formula V-2, Formula V-3, or Formula V-4 is isolated. In some embodiments, the isolated compound of Formula V-1, Formula V-2, Formula V-3, or Formula V-4 is substantially pure (e.g., at least 80%, at least 85%, at least 90%, at least 95%, or at least 98% pure by weight). In some embodiments, the isolated compound of Formula V-1, Formula V-2, Formula V-3, or Formula V-4 is about 80%, about 85%, about 90%, about 95%, about 98% pure by weight, or any ranges between the specified values. In some embodiments, the isolated compound of Formula V-1, Formula V-2, Formula V-3, or Formula V-4 is substantially free (e.g., less than 5%, less than 3%, less than 2%, less than 1%, less than 0.5%, or less than 0.1% by weight) of other diastereomers and/or geometric isomer. In some embodiments, the isolated compound of Formula V-1, Formula V-2, Formula V-3, or Formula V-4 has about 5%, about 3%, about 2%, about 1%, about 0.5%, about 0.1% by weight, or any ranges between the specified values, of other diastereomers and/or geometric isomer. In some embodiments, the isolated compound of Formula V-1, Formula V-2, Formula V-3, or Formula V-4 is free of (i.e., non-detectable using current analytical tools) other diastereomers and/or geometric isomer.

In some embodiments, the synthetic intermediate is a compound of Formula V-5, Formula V-6, or Formula V-7, or a compound of Formula V-8 or a geometric isomer or a salt thereof:

Formula V-5

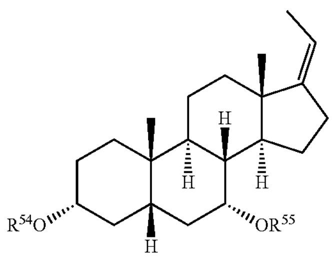

Formula V-6

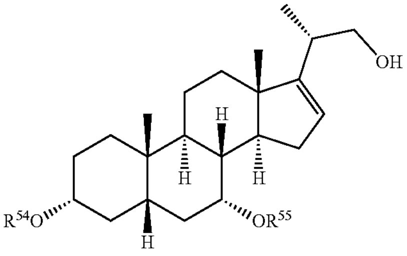

Formula V-7

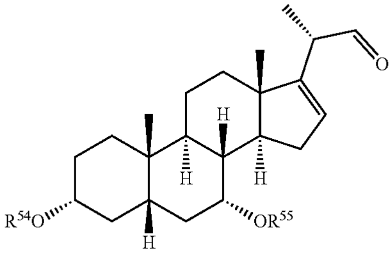

Formula V-8

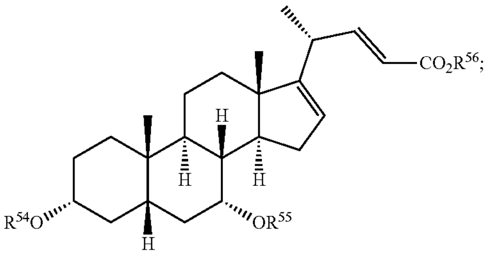

wherein each of $R^{54}$ and $R^{55}$ is independently H or a hydroxyl protecting group, and $R^{56}$ is H or an optionally substituted alkyl, provided that when $R^{54}$ and $R^{55}$ are both acetyl, then $R^{56}$ is not methyl.

$R^{54}$ and $R^{55}$ in each of Formula V-5, Formula V-6, Formula V-7, and Formula V-8 can be independently selected. In some embodiments, $R^{54}$ and $R^{55}$ are each H. In some embodiments, $R^{54}$ and $R^{55}$ are each independently a hydroxyl protecting group (e.g., as described herein). In some embodiments, $R^{54}$ and $R^{55}$ are the same hydroxyl protecting group. In some embodiments, $R^{54}$ and $R^{55}$ are different. For example, one of $R^{54}$ and $R^{55}$ can be hydrogen and the other of $R^{54}$ and $R^{55}$ can be a hydroxyl protecting group. Suitable hydroxyl protecting groups include any of those described herein. In some embodiments, the hydroxyl protecting group is acetyl.

Some embodiments are directed to the compound of Formula V-8, a geometric isomer thereof, or a salt thereof. $R^{54}$, $R^{55}$, and $R^{56}$ in Formula V-8 are described hereinabove. In some embodiments, $R^{56}$ is H. In some embodiments, $R^{56}$ is an optionally substituted alkyl (e.g., optionally substituted $C_{1-6}$ alkyl), provided that when $R^{54}$ and $R^{55}$ are both acetyl, then $R^{56}$ is not methyl. In some embodiments, $R^{56}$ is ethyl.

In some embodiments, the compound of Formula V-5, Formula V-6, Formula V-7, or Formula V-8 is isolated. In some embodiments, the isolated compound of Formula V-5, Formula V-6, Formula V-7, or Formula V-8 is substantially pure (e.g., at least 80%, at least 85%, at least 90%, at least 95%, or at least 98% pure by weight). In some embodiments, the isolated compound of Formula V-5, Formula V-6, Formula V-7, or Formula V-8 is about 80%, about 85%, about 90%, about 95%, about 98% pure by weight, or any ranges between the specified values. In some embodiments, the isolated compound of Formula V-5, Formula V-6, Formula V-7, or Formula V-8 is substantially free (e.g., less than 5%, less than 3%, less than 2%, less than 1%, less than 0.5%, or less than 0.1% by weight) of other diastereomers and/or geometric isomer. In some embodiments, the isolated compound of Formula V-5, Formula V-6, Formula V-7, or Formula V-8 has about 5%, about 3%, about 2%, about 1%, about 0.5%, about 0.1% by weight, or any ranges between the specified values, of other diastereomers and/or geometric isomer. In some embodiments, the isolated compound of Formula V-5, Formula V-6, Formula V-7, or Formula V-8 is free of (i.e., non-detectable using current analytical tools) other diastereomers and/or geometric isomer.

In some embodiments, the synthetic intermediate is a compound having a structure of Formula III-8

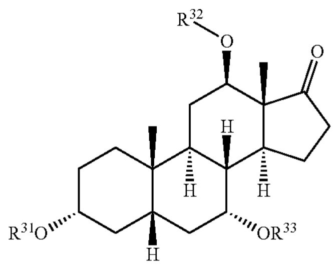

wherein $R^{31}$, $R^{32}$ and $R^{33}$ are each independently H or a hydroxyl protecting group. In some embodiments, $R^{31}$, $R^{32}$, and $R^{33}$ are each H. In some embodiments, $R^{31}$, $R^{32}$, and $R^{33}$ are each independently a hydroxyl protecting group (e.g., as described herein). In some embodiments, $R^{31}$, $R^{32}$, and $R^{33}$ are the same hydroxyl protecting group. In some embodiments, at least two of $R^{31}$, $R^{32}$, and $R^{33}$ are the same hydroxyl protecting group. In some embodiments, at least two of $R^{31}$, $R^{32}$, and $R^{33}$ are different. For example, one of $R^{31}$, $R^{32}$, and $R^{33}$ can be hydrogen and the other two of $R^{31}$, $R^{32}$, and $R^{33}$ can be the same or different hydroxyl protecting group. Suitable hydroxyl protecting groups for Formula III-8 include any of those described herein. In some embodiments, the hydroxyl protecting group is acetyl.

In some embodiments, the compound of Formula III-8 is isolated. In some embodiments, the isolated compound of Formula III-8 is substantially pure (e.g., at least 80%, at least 85%, at least 90%, at least 95%, or at least 98% pure by weight). In some embodiments, the isolated compound of Formula III-8 is about 80%, about 85%, about 90%, about 95%, about 98% pure by weight, or any ranges between the specified values. In some embodiments, the isolated compound of Formula III-8 is substantially free (e.g., less than 5%, less than 3%, less than 2%, less than 1%, less than 0.5%, or less than 0.1% by weight) of other diastereomers. In some embodiments, the isolated compound of Formula III-8 has about 5%, about 3%, about 2%, about 1%, about 0.5%, about 0.1% by weight, or any ranges between the specified values, of other diastereomers. In some embodiments, the isolated compound of Formula III-8 is free of (i.e., non-detectable using current analytical tools) other diastereomers.

Pharmaceutical or Cosmetic Compositions

Certain embodiments of the present disclosure are directed to pharmaceutical or cosmetic compositions comprising one or more of CA, DCA, CDCA and their esters and salts, which are free of animal derived impurities.

In some embodiments, the pharmaceutical or cosmetic composition comprises an effective amount of high purity (e.g., a purity of at least 98%, at least 99%, at least 99.5%, or at least 99.9% by weight) cholic acid or a pharmaceutically or cosmetically acceptable salt thereof, or a high purity cholic acid composition herein, and a pharmaceutically or cosmetically acceptable excipient. In some embodiments, the cholic acid or pharmaceutically or cosmetically acceptable salt thereof has at least a purity of 99% by weight, for example, 99.2%, 99.5%, 99.9%, or greater than 99.9% by weight. In any of the embodiments described herein, the cholic acid or pharmaceutically or cosmetically acceptable salt thereof can also be characterized by being free of any animal derived impurities. In some embodiments, the pharmaceutical or cosmetic composition further comprises an effective amount of high purity (e.g., a purity of at least 98%, at least 99%, at least 99.5%, or at least 99.9% by weight) chenodeoxycholic acid or a pharmaceutically or cosmetically acceptable salt thereof. In any of the embodiments described herein, the chenodeoxycholic acid or pharmaceutically or cosmetically acceptable salt thereof can also be characterized by being free of any animal derived impurities. In some embodiments, the pharmaceutical or cosmetic composition further comprises an effective amount of high purity (e.g., a purity of at least 98%, at least 99%, at least 99.5%, or at least 99.9% by weight) deoxycholic acid or a pharmaceutically or cosmetically acceptable salt thereof. In any of the embodiments described herein, the deoxycholic acid or pharmaceutically or cosmetically acceptable salt thereof can also be characterized by being free of any animal derived impurities.

The high purity cholic acid can be obtained, for example, by the synthetic methods provided herein. In some embodiments, the present disclosure also provides a high purity cholic acid composition. Typically, the high purity cholic acid composition herein comprises cholic acid or a salt thereof, along with one or more process impurities. For example, in some embodiments, the high purity cholic acid composition comprises, consists essentially of, or consists of, cholic acid or a salt thereof, and one or more (e.g., 1, 2, 3, or all) compounds selected from Compounds 32-35 (see Example 6) or a salt thereof. In some embodiments, the high purity cholic acid composition can comprise any one of Compounds 32-35, or a salt thereof, any two of Compounds 32-35, or a salt thereof, any three of Compounds 32-35, or a salt thereof, or all of Compounds 32-35, or a salt thereof. In some embodiments, the total amount of Compounds 32-35 and salts thereof, as applicable, is less than 5% (e.g., less than 5%, less than 4%, less than 3%, less than 2%, less than 1%, less than 0.5%, less than 0.2%, less than 0.1%), more preferably, less than 2%, or less than 1% (e.g., less than 0.5%, less than 0.2%, less than 0.1%), by weight and/or by HPLC area of the cholic acid and salt thereof. For the avoidance of doubt, when the purity level is recited as weight percentage, the respective compound and all of its salt forms are considered, and the equivalent weight of the free acid form is then used for the weight percentage calculation. For example, when it is said that the weight percentage of Compound 32 and salt is less than 1% of the cholic acid and salt thereof, it should be understood that the equivalent weight of Compound 32 as free acid, after considering all salt forms of Compound 32 that may be present in the composition, is less than 1% by weight of cholic acid, also expressed as equivalent weight of the free acid, after considering all salt forms of cholic acid that may be present in the composition. Methods for determining purity of a composition are known to those skilled in the art. For example, the purity of the cholic acid composition herein can be analyzed based on weight, HPLC area, or both. Those skilled in the art would know how to validate an analytical method in determining such purity level. In any of the embodiments described herein, the purity of the cholic acid composition herein can be based on weight percentages.

Each of Compounds 32-35 or a salt thereof, if present in the high purity cholic acid composition, should be preferably less than 5% (e.g., less than 5%, less than 4%, less than 3%, less than 2%, less than 1%, less than 0.5%, less than 0.2%, less than 0.1%), more preferably, less than 2%, or less than 1% (e.g., less than 0.5%, less than 0.2%, less than 0.1%), by weight and/or by HPLC area of the cholic acid and salt thereof. For example, in some embodiments, the high purity cholic acid composition comprises Compound 32, or a salt thereof, in an amount of less than 1% (e.g., less than 0.5%, less than 0.2%, less than 0.1%) by weight and/or by HPLC area of the cholic acid and salt thereof. In some embodiments, the high purity cholic acid composition comprises Compound 33, or a salt thereof, in an amount of less than 5% (e.g., less than 5%, less than 4%, less than 3%, less than 2%, less than 1%, less than 0.5%, less than 0.2%, less than 0.1%), more preferably, less than 2%, or less than 1% (e.g., less than 0.5%, less than 0.2%, less than 0.1%), by weight and/or by HPLC area of the cholic acid and salt thereof. In some embodiments, the high purity cholic acid composition comprises Compound 34, or a salt thereof, in an amount of less than 1% (e.g., less than 0.5%, less than 0.2%, less than 0.1%) by weight and/or by HPLC area of the cholic acid and salt thereof. In some embodiments, the high purity cholic acid composition comprises Compound 35, or a salt thereof, in an amount of less than 5% (e.g., less than 5%, less than 4%, less than 3%, less than 2%, less than 1%, less than 0.5%, less than 0.2%, less than 0.1%), more preferably, less than 2%, or less than 1% (e.g., less than 0.5%, less than 0.2%, less than 0.1%), by weight and/or by HPLC area of the cholic acid and salt thereof. In some embodiments, the high purity cholic acid composition comprises cholic acid or salt thereof with a purity of at least 95% (e.g., at least 96%, at least 97%, at least 98%, or at least 99%). In some embodiments, the high purity cholic acid composition comprises cholic acid or salt thereof with a purity of at least 99% by weight and/or HPLC area, for example, 99.2%, 99.5%, 99.9%, or greater than 99.9% by weight, by HPLC area, or both.

The levels of Compounds 32-35 in a high purity cholic acid composition herein can be controlled. For example, when needed, further purification of a cholic acid composition herein can be made to reduce the level of (or even eliminate) one or more of Compounds 32-35. For example, as shown in FIG. 2, these impurities can be readily separated by HPLC, which has baseline separation in FIG. 2. See also Example 6, where each of Compounds 32-35 were isolated by reverse phase HPLC and characterized and identified. Although typically not desired, the level of one or more of Compounds 32-35 can also be increased by adding the respective substantially pure (e.g., at least 80%, at least 85%, at least 90%, at least 95%, or at least 98% pure by weight) Compounds 32-35 to the high purity cholic acid composition. Compounds 32-35 are themselves also useful, for example, they can be useful in quality control for cholic acid manufacturing, in identifying sources of cholic acid, or identifying potential synthetic pathways to such cholic acid.

The pharmaceutical or cosmetic composition comprising cholic acid or a pharmaceutically or cosmetically acceptable salt thereof can be formulated in various forms with suitable excipient(s). Suitable excipients can be any solid, liquid, semi-solid or, in the case of an aerosol composition, gaseous excipient that is generally available to one of skill in the art. Solid excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Examples of liquid and semisolid excipients can include glycerol, propylene glycol, water, ethanol and various oils, including those of petroleum, vegetable or synthetic origin, e.g., peanut oil, soybean oil, mineral oil, sesame oil, etc. Examples of liquid carriers, particularly for injectable solutions, include water, saline, aqueous dextrose, and glycols.

In some embodiments, the pharmaceutical or cosmetic composition is preferably an aqueous solution, e.g., suitable for subcutaneous injection. In some embodiments, the aqueous solution comprises: (i) high purity cholic acid, chenodeoxycholic acid, a pharmaceutically or cosmetically acceptable salt thereof, or a combination thereof; e.g., a high purity cholic acid composition described herein; and (ii) a pharmaceutical, veterinary, or cosmetic excipient. In some embodiments, the solution can further comprise a second therapeutic agent selected from the group consisting of: anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and anti-diarrhea agents. In some embodiments, a solution is in a container that contains up to 500 mL of solution. Such container can be a syringe or syringe-loadable container.

Non-limiting exemplary methods for formulating the cholic acid or pharmaceutically or cosmetically acceptable salt thereof include those described in WO 2015/198150, titled "Methods and Compositions of Bile Acids and Salts for Reduction of Fat," the content of which is hereby incorporated by reference in its entirety.

Method of Use

Cholic acid, deoxycholic acid, and chenodeoxycholic acid are known to have medical and/or cosmetic uses. For example, WO 2015/198150 describes the use of cholate and/or chenodeoxycholate to reduce subcutaneous fat accumulations in a mammal by local administration to a target site. WO 2015/198150 also describes that cholate and/or chenodeoxycholate compositions can be used for dissolving lipomas, fat, mesotherapy, separating tissue, tumor reduction, cancer reduction, cancer treatment, and any other clinical situation where one might want to use loosen, remove, assist the body consumption or resolution of wax, lipids, proteins, or carbohydrates from a part or region of the body. For example, in the treatment of lipomas, the cholate and/or chenodeoxycholate compositions can be injected subcutaneously in contact with the lipomas to lyse the lipomas. Methods of using deoxycholic acid are described, for example, in U.S. Pat. No. 7,622,130, and U.S. Application Publication Nos. 2005-0267080 A1 and 2006-0127468 A1, etc.

The CA, DCA, CDCA, and their esters and salts described herein can also be used for any of the known medical and/or cosmetic uses. In some embodiments, the present disclosure also provides a method for non-surgical removal of a localized fat deposit in a subject. In some embodiments, the method comprises administering to the subject an effective amount of any of the pharmaceutical or cosmetic compositions described hereinabove, for example, a pharmaceutical or cosmetic composition comprising a fat-lysing effective amount of high purity (e.g., a purity of at least 98%, at least 99%, at least 99.5%, or at least 99.9% by weight) cholic acid, chenodeoxycholic acid, a pharmaceutically or cosmetically acceptable salt thereof, or a combination thereof, e.g., a high purity cholic acid composition described herein, and a pharmaceutically or cosmetically acceptable excipient.

EXAMPLES

The various starting materials, intermediates, and compounds of the preferred embodiments can be isolated and purified where appropriate using conventional techniques such as precipitation, filtration, crystallization, evaporation, distillation, and chromatography. Characterization of these compounds can be performed using conventional methods such as by melting point, mass spectrum, nuclear magnetic resonance, and various other spectroscopic analyses. Exemplary embodiments of steps for performing the synthesis of products described herein are described in greater detail infra. Table 1 describes abbreviations used to express various compounds/moieties/apparatus/procedure/property in the exemplary reaction schemes and synthetic routes described in the following examples and throughout the specification.

TABLE 1

List of Abbreviations

| Ac | Acetyl |
|---|---|
| Ac-DHEA | Acetyl-dehydroepiandrosterone |
| CA | Cholic acid |
| CDCA | Chenodeoxycholic acid |
| $Cu(OTf)_2$ | Copper triflate |
| DCA | Deoxycholic acid |
| DCM | Dichloromethane |

TABLE 1-continued

List of Abbreviations

| Ac | Acetyl |
|---|---|
| DDQ | Dichloro-5,6-dicyano-1,4-benzoquinone |
| DHEA | Dehydroepiandrosterone |
| DMAP | 4-dimethylaminopyridine |
| DMF | N,N-dimethylformamide |
| DMSO | Dimethyl sulfoxide |
| EDTA | Ethylenediaminetetraacetic acid |
| Et | ethyl |
| $Et_3N$ | triethylamine |
| EtOAc/EA | ethyl acetate |
| EtOH | ethanol |
| Eq/equiv | equivalent |
| g(s) | gram(s) |
| h/hr(s) | hour(s) |
| HPLC | High pressure liquid chromatography |
| $^1$H NMR | Proton nuclear magnetic resonance |
| mCPBA/ MCPBA | 3-Chloroperoxybenzoic acid |
| Me | methyl |
| MeOH | methanol |
| mL | milliliter(s) |
| mg | milligram(s) |
| mol | mole(s) |
| mmol | millimole(s) |
| min(s) | minute(s) |

TABLE 1-continued

List of Abbreviations

| Ac | Acetyl |
|---|---|
| NaH | Sodium hydride |
| NCS | N-chlorosuccinimide |
| NBS | N-bromosuccinimide |
| PE | petroleum ether |
| PTSA/ p-TsOH | Para-toluenesulfonic acid |
| Py | pyridine |
| pre-TLC/ prep-TLC | Preparative thin layer chromatography |
| rt | Room tempreture |
| TEA | triethylamine |
| TEMPO | (2,2,6,6-tetramethylpiperidin-1-yl)oxidanyl |
| THF | tetrahydrofuran |
| TLC | Thin layer chromatography |
| μL/uL | microliter |
| μmol/ umol | micromole(s) |

Example 1

Synthesis of Cholic Acid from DHEA: Route 1

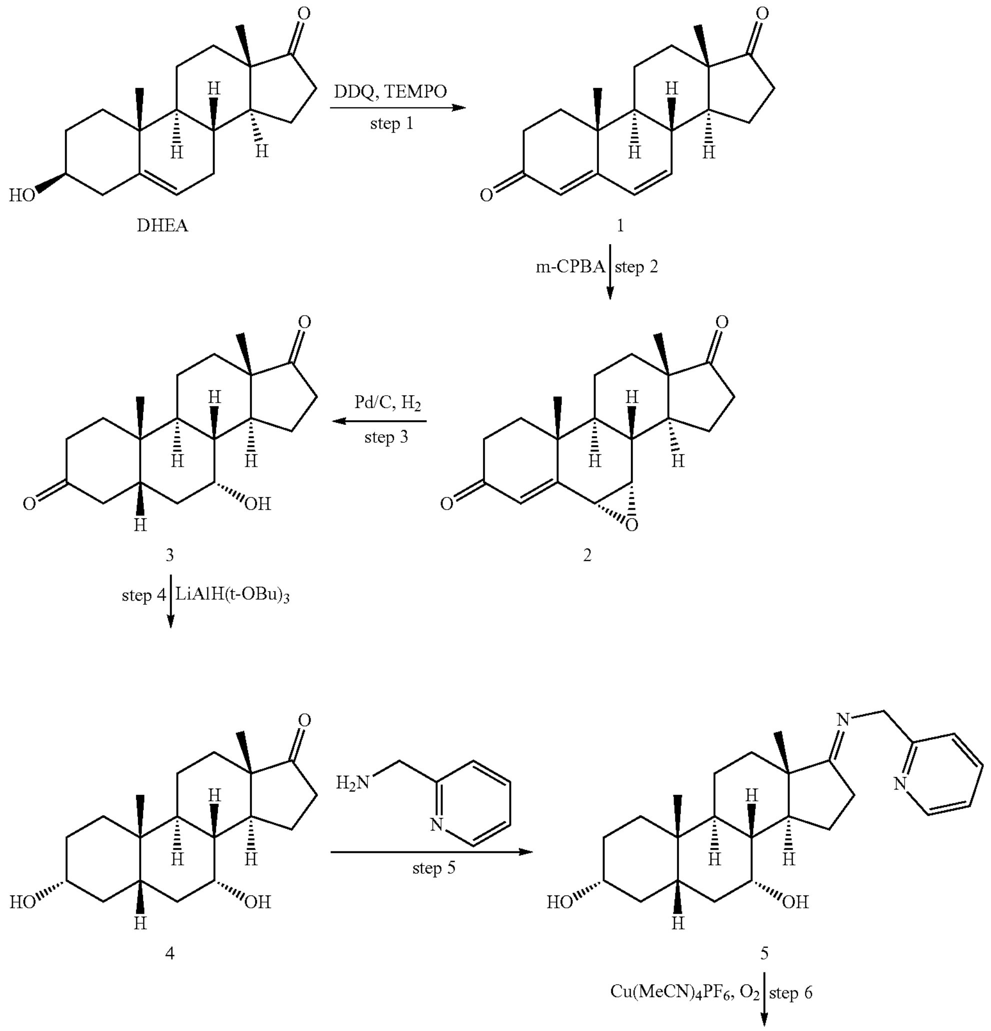

DHEA

1

2

3

4

5

-continued
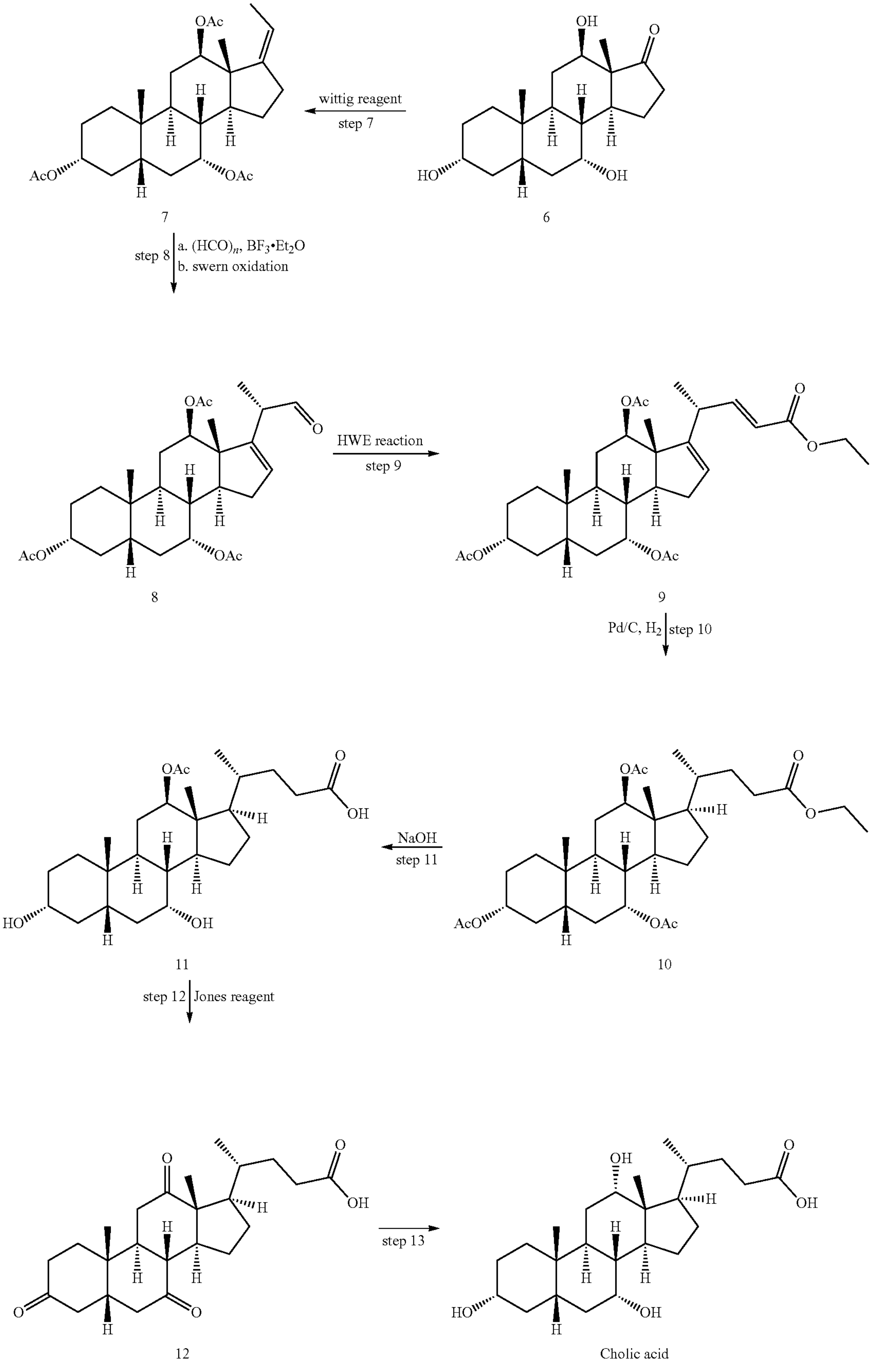

Step 1

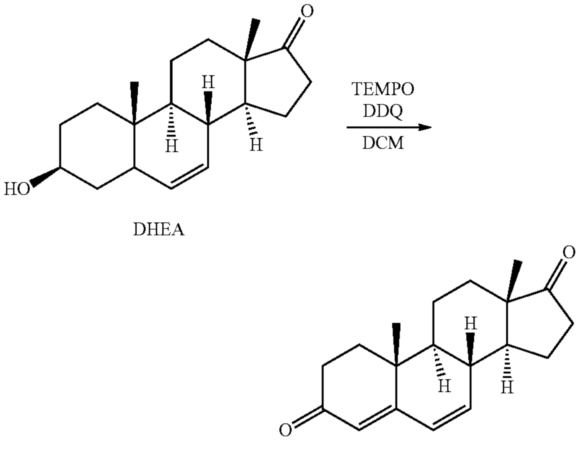

DHEA

1

To a flask was added DHEA (50.00 g, 173.36 mmol, 1.00 eq) and DCM (1.00 L) at 15° C. Then, it was cooled to 0° C., TEMPO (2.73 g, 17.34 mmol, 0.10 eq) was added, and DDQ (86.58 g, 381.39 mmol, and 2.20 eq) was added in portions at 0° C. The reaction mixture was warmed to 25° C. and stirred at 25° C. for 48 hrs, TLC showed one new main spot was formed. The reaction was filtered, and the filtrate was washed with saturated $Na_2SO_3$ (100 mL*2) and brine (200 mL*2). The combined organic phase was dried with anhydrous $Na_2SO_4$ and concentrated in vacuum. The residue was purified by column chromatography (PE/EA=50/1 to 10/1) to afford Compound 1 (39.0 g, 135.35 mmol, 78.08% yield) as white solid. $^1$H NMR, (400 MHz, CDC13); δ=6.21 (s, 2H), 5.78-5.71 (m, 1H), 2.66-2.55 (m, 1H), 2.53-2.46 (m, 1H), 2.46-2.35 (m, 2H), 2.22-2.13 (m, 2H), 2.08-2.01 (m, 1H), 1.92 (td, J=3.1, 13.0 Hz, 1H), 1.80-1.69 (m, 3H), 1.56-1.50 (m, 1H), 1.48-1.42 (m, 1H), 1.39-1.32 (m, 1H), 1.32-1.24 (m, 1H), 1.16 (s, 3H), 0.99 (s, 3H).

Step 2

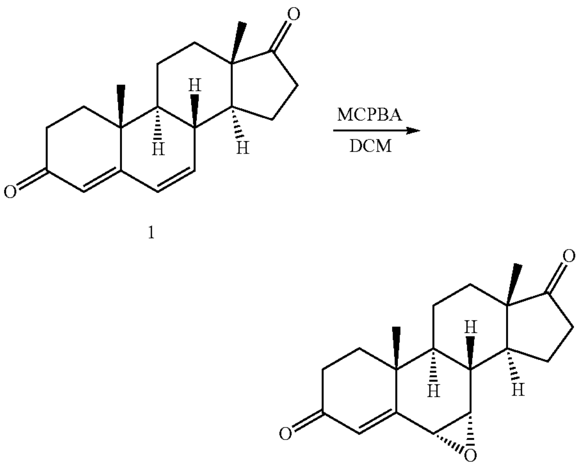

1

2

To a solution of compound 1 (39.00 g, 137.14 mmol, 1.00 eq) in DCM (400.00 mL) was drop-wise added m-CPBA (61.25 g, 301.71 mmol, 87% purity, 2.20 eq) which dissolved in DCM (50.00 mL) to the reaction at 5° C. The resulting solution was stirred at 5° C. for 24 h, TLC showed the starting material was consumed completely, and one new main spot was formed. Then the reaction was filtered and the filtrate was washed with saturated $Na_2SO_3$ solution (200 mL) at 25° C. for 0.5 h. The organic phase was separated and concentrated in vacuum. The residue was purified by column chromatography (PE/EA=20/1 to 5/1) to afford Compound 2 (16.12 g, 51.79 mmol, 37.76% yield) as white solid. $^1$H NMR, (400 MHz, $CDCl_3$): δ=6.16 (s, 1H), 3.55 (d, J=3.8 Hz, 1H), 3.48 (d, J=3.6 Hz, 1H), 2.63-2.50 (m, 3H), 2.30-2.22 (m, 2H), 2.21-2.14 (m, 1H), 1.98 (ddd, J=2.3, 5.3, 13.2 Hz, 2H), 1.91-1.85 (m, 2H), 1.80-1.72 (m, 4H), 1.43-1.33 (m, 3H), 1.30-1.25 (m, 2H), 1.15 (s, 3H), 0.97 (s, 3H).

Step 3

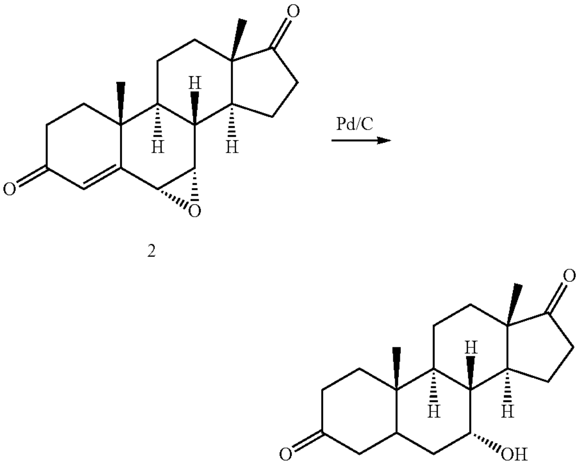

2

3

To a solution of compound 2 (16.12 g, 53.66 mmol, 1.00 eq) in Py (160.00 mL) was added Pd/C (10%, 1.70 g) under $N_2$ protection at 25° C. The suspension was degassed under vacuum and purged with $H_2$ several times. The reaction was stirred (50 psi) at 25° C. for 12 hours under $H_2$ atmosphere, TLC showed the starting material was consumed completely and one new main spot was formed. The reaction mixture was filtered with celite, the filtrate was washed with 5% HCl (100 mL) and extracted with EA (150 mL). The organic phase was separated and concentrated in vacuum to give 16.34 g of crude compound 3 as light yellow solid.

Step 4

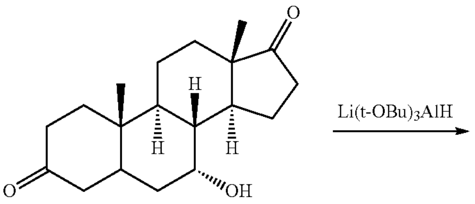

3

-continued

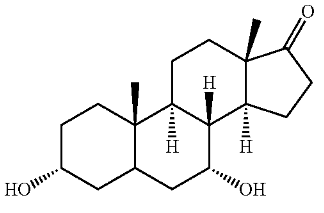

4

To a solution of compound 3 (16.34 g, 53.68 mmol, 1.00 eq) in THF (150.00 mL) was drop-wise added LiAlH(t-BuO)$_3$ (16.99 g, 67.10 mmol, 18.88 mL, 1.25 eq) which was dissolved in THF (30.00 mL) at 5° C., The resulting solution was stirred at 5° C. for 0.5 hr. TLC showed one main spot was formed. The reaction mixture was quenched by 5% HCl (50 ml), extracted with EA (50 ml*2), the organic phase was separated and concentrated in vacuum. The residue was purified by silica gel chromatography (PE/EA=5:1 to 2:1) to afford Compound 4 (6.20 g, 35.62% yield) as colorless oil.

Step 5

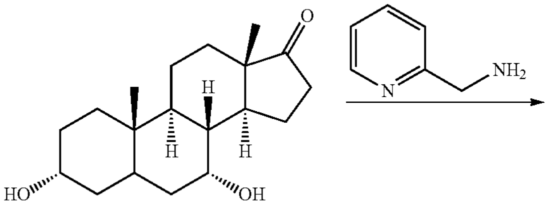

4

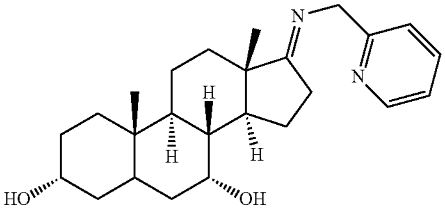

5

To a mixture of compound 4 (6.00 g, 19.58 mmol, 1.00 eq) and 2-pyridylmethanamine (10.59 g, 97.90 mmol, 9.99 mL, 5.00 eq) in toluene (50.00 mL) was added PTSA (101.15 mg, 0.58 mmol, 0.03 eq) at 25° C., the mixture was stirred at 120° C. for 2 hrs with Dean-Stark apparatus. Then the reaction mixture was diluted with EA (100 ml), washed with saturated $NaHCO_3$ (20 ml) and water (50 ml). The organic phase was separated and concentrated in vacuum. The residue was triturated by EA (10 ml) at 25° C. to afford Compound 5 (4.12 g, 10.13 mmol, 51.73% yield, and 96.5% purity) as white solid. $^1$H NMR, (400 MHz, $CDCl_3$): δ=8.45 (br d, J=4.5 Hz, 1H), 7.63-7.56 (m, 1H), 7.34 (d, J=7.8 Hz, 1H), 7.10-7.04 (m, 1H), 4.61-4.47 (m, 2H), 3.91 (br s, 1H), 3.47-3.36 (m, 2H), 2.46-2.36 (m, 1H), 2.31-2.20 (m, 1H), 2.18-2.07 (m, 2H), 2.01-1.92 (m, 2H), 1.91-1.78 (m, 3H), 1.68-1.62 (m, 2H), 1.48-1.39 (m, 2H), 1.38-1.25 (m, 5H), 1.20-1.11 (m, 2H), 0.98-0.93 (m, 1H), 0.88 (s, 3H), 0.83 (s, 3H).

Step 6

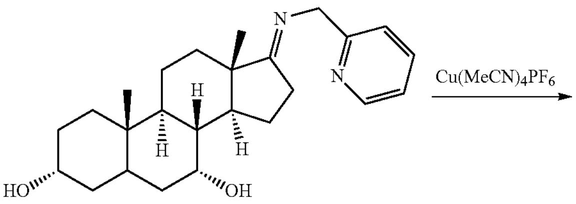

5

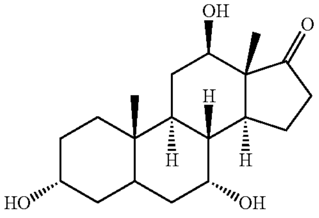

6

To a solution of compound 5 (2.00 g, 5.04 mmol, 1.00 eq) in acetone (10.00 mL) and MeOH (10.00 mL) was added sodium ascorbate (2.00 g, 10.09 mmol, 2.0 eq) and Cu(MeCN)$_4$PF$_6$ (2.63 g, 7.06 mmol, 1.40 eq) in sequence at 25° C. After stirred at 25° C. for 5 mins, oxygen (15 psi) was bubbled through the reaction mixture for 10 mins. Then the reaction was heated to 50° C. and stirred at 50° C. for 2 hrs under $O_2$ atmosphere. TLC showed one new main spot was formed. After cooled to 25° C., EA (100 mL) and saturated EDTA-Na$_4$ (50 mL) was added, the mixture was stirred at 25° C. for 30 mins. The organic phase was separated and concentrated in vacuo. The residue was purified by column chromatography (PE/EA=3/1 to 1/2) to afford Compound 6 (0.25 g, 0.75 mmol, 14.95% yield) as light yellow solid.

Step 7

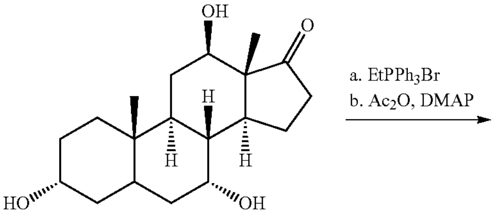

6

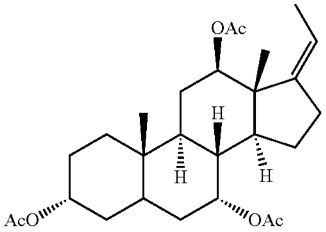

7

EtPPh3Br (2.41 g, 6.50 mmol, 5.00 eq) in a flask was dried under high vacuum for 1 hr at 70° C. Dry THF (3.00 mL) was added, followed by adding t-BuOK (0.73 g, 6.50 mmol, 5.00 eq) under $N_2$. The entire mixture was still stirred at 70° C. for 0.5 hr under $N_2$. The solution of Compound 6 (0.42 g, 1.30 mmol, 1.00 eq) in dry THF (2.00 mL) was added to the reaction at 70° C., the reaction was stirred at 70°

C. for another 2 hrs. TLC showed the starting material was all consumed and one new main spot was formed. After cooling to room temperature, the solution was diluted by EA (40 mL), quenched by saturated NaCl solution (10 mL). The aqueous solution was extracted with EA (20 mL), dried over $Na_2SO_4$, concentrated in vacuum to give 0.48 g as light yellow oil.

The obtained yellow oil (0.48 g, 1.45 mmol, 1.00 eq) was dissolved in DCM (5.00 mL) at 25° C., followed by adding $Ac_2O$ (621.97 mg, 6.05 mmol, 570.62 uL, 4.2 eq), $Et_3N$ (0.88 g, 8.70 mmol, 1.21 mL, 6.00 eq) and DMAP (35.44 mg, 290.11 umol, 0.20 eq) at 25° C. The reaction was stirred at 25° C. for 7 hrs. TLC showed the starting material was consumed completely and one new main spot was formed. The reaction was diluted with EA (50 ml), washed with $H_2O$ (10 mL), dried over $Na_2SO_4$ and filtered, the organic layer was concentrated in vacuo. The residue was purified by column chromatography (PE/EA=50/1 to 20/1) to give Compound 7 (0.18 g, 0.38 mmol, 26.28% yield) as colorless oil.

Step 8

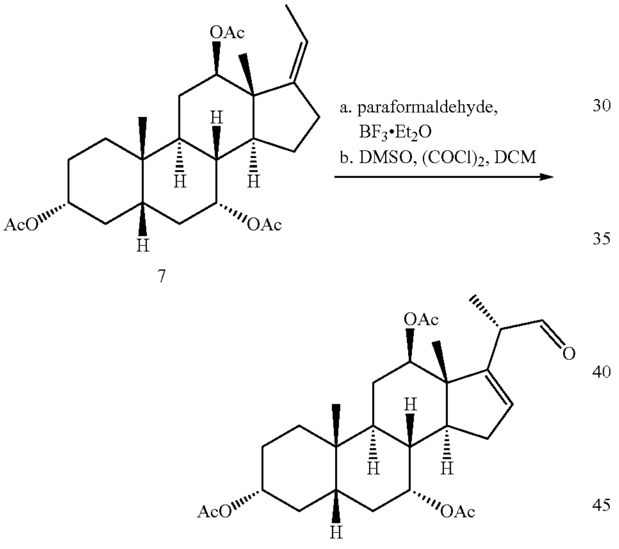

7

8

To a 50 ml flask was added compound 7 (50.00 mg, 108.55 umol, 1.00 eq) and DCM (5.00 mL). The reaction was cooled to 0° C.; paraformaldehyde (48.89 mg, 542.77 umol, 5.00 eq) was added to the reaction at 0° C., followed by adding $BF_3.Et_2O$ (1.54 mg, 10.86 umol, 1.34 uL, 0.10 eq) to the reaction at 0° C. The reaction was warmed to 15° C., and stirred at 15° C. for 2 hrs. TLC showed one new main spot was formed. The reaction was diluted with DCM (50 ml), and quenched by water (30 ml). The organic layer was concentrated in vacuo. The residue was purified by pre-TLC (PE/EA=1/1) to give colorless oil residue (40 mg).

To a 10 ml tube was added $(COCl)_2$ (61.84 mg, 487.18 umol, 42.65 uL, 2.40 eq) and DCM (6.00 mL). The mixture was cooled to −78° C. DMSO (63.44 mg, 811.96 umol, 63.44 uL, 4.00 eq) was added drop-wise to the reaction mixture at −78° C. After addition, the reaction was stirred at −78° C. for 0.5 hrs. The colorless oil residue which previous prepared (two batches, 100 mg) was added to the reaction at −78° C. It was stirred at −78 for 0.5 hrs. TEA (205.41 mg, 2.03 mmol, 281.38 uL, 10.00 eq) was added drop-wise at −78° C. After addition, the reaction was warmed to 15° C., and it was stirred at 15° C. for 0.5 hr. TLC showed one new main spot was formed. The reaction was diluted with DCM (50 ml), and quenched by water (30 ml). The separated organic layer was concentrated in vacuo. The residue was purified by pre-TLC to give compound 8 (50 mg, 50% yield).

Step 9

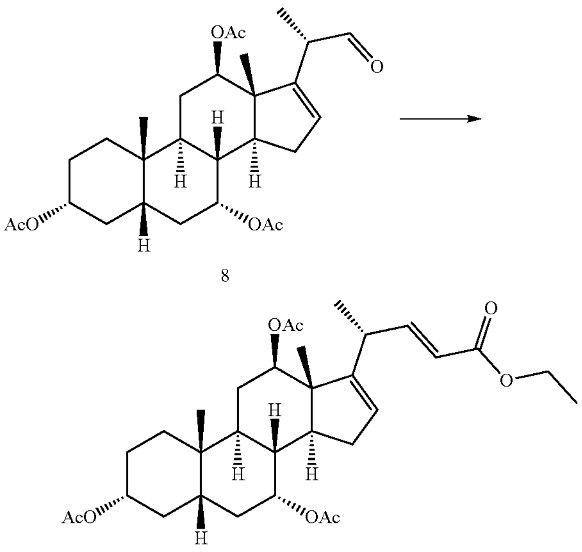

8

9

To a 10 ml tube was added NaH (32.75 mg, 818.64 umol, 60% purity, 4.00 eq) and THF (2.00 mL), followed by adding ethyl 2-diethoxyphosphorylacetate (229.41 mg, 1.02 mmol, 203.02 uL, 5.00 eq) to the flask at 15° C. The resulting mixture was stirred at 15° C. for 10 mins. Compound 8 (100.00 mg, 204.66 umol, 1.00 eq) was added to the flask at 15° C., and it was stirred at 15° C. for 0.5 hr, TLC showed one new main spot was formed. The reaction was quenched by water (5 ml), and extracted with DCM (2*30 ml). The organic layer was concentrated in vacuo. The residue was purified by pre-TLC to give compound 9 (100 mg, 87.46% yield) as colorless oil. Mass (m/z): 581.4 ($M^+$+23).

Step 10

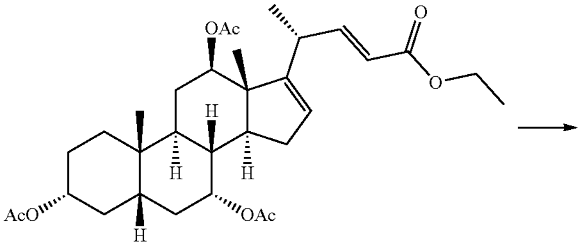

9

-continued

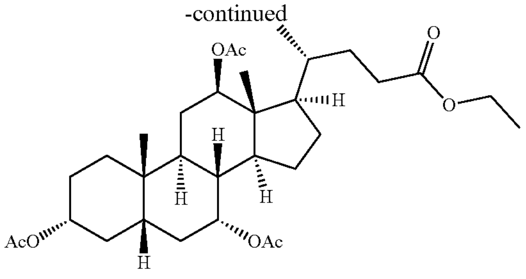

10

To a 35 ml pressure tube was added compound 9 (100.00 mg, 178.99 umol, 1.00 eq), EtOH (4.00 mL) and Pd/C (10.00 mg) at 25° C. The mixture was purged with $H_2$ gas (50 psi) and stirred at 25° C. for 4 hrs. TLC showed one new main spot was formed. The resulting mixture was filtered, the filtrate was concentrated in vacuo to give compound 10 (60 mg, crude) as colorless oil. Mass (m/z): 585.4 ($M^+$+23).

Step 11

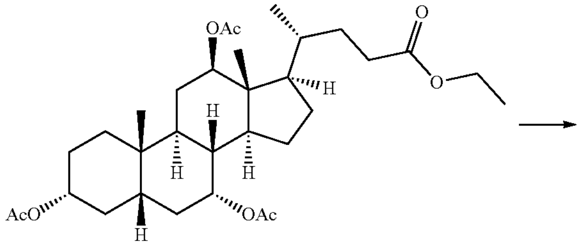

10

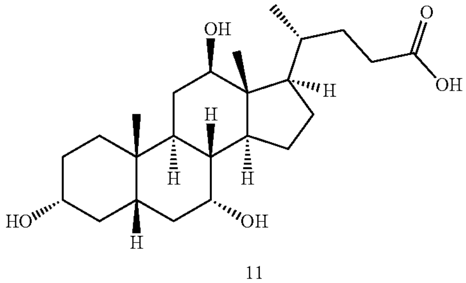

11

To a solution of compound 10 (60.00 mg, 106.62 umol, 1.00 eq) in MeOH (4.00 mL) was added NaOH (51.18 mg, 1.28 mmol, 12.00 eq) at 25° C. After that, the reaction was heated to 60° C., and it was stirred at 60° C. for 2 hrs. TLC showed one new main spot was formed. The reaction was cooled to rt, concentrated in vacuo to remove solvent, the resulting residue was dissolved in water (5 ml), acidized by HCl to PH=3. The resulting aqueous layer was extracted with EA (3*15 ml). The organic layer was concentrated in vacuo to give compound 10 (70 mg, crude) as white solid. Mass (m/z): 431.1 ($M^+$+23), 839.1(2$M^+$+23).

Step 12

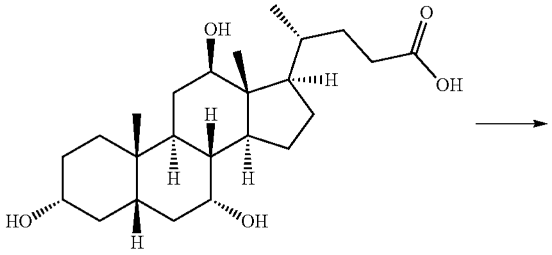

11

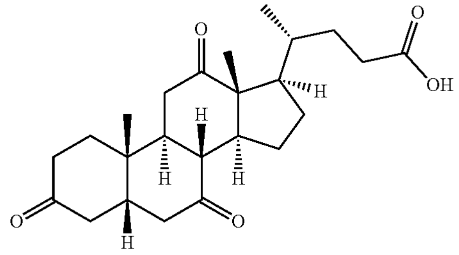

12

To a solution of compound 11 (70 mg, 160.32 umol, 1.00 eq) in acetone (3 mL) was added Jones reagent (95.27 mg, 480.96 umol, 3 eq) drop-wise at 20° C. After addition, the reaction was stirred at 20° C. for 10 mins, TLC showed one new main spot was formed. The reaction was quenched by isopropanol (0.5 ml) and diluted with water (5 ml). The resulting aqueous mixture was extracted with EA (3*15 ml). The organic layer was concentrated in vacuo. The residue was purified by pre-TLC to give compound 12 (20 mg, 48 umol, 29.9% yield) as white solid. Mass (m/z): 403.3 ($M^+$+1).

Step 13

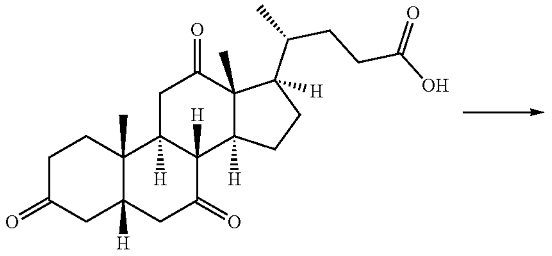

12

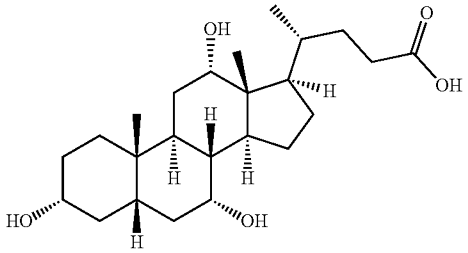

Cholic acid

To a solution of compound 12 (10.00 mg, 24.84 umol, 1 eq) in THF (5 mL) was added LiAlH(t-BuO)$_3$ (94.38 mg, 372.65 umol, 104.40 uL, 15 eq) at 20° C. It was stirred at 20° C. for 1 hr and at 40° C. for 16 hrs, TLC showed one new main spot was formed. The reaction was diluted by EA (50 ml), quenched by HCl (10 ml, 1M). The separated organic layer was concentrated in vacuo. The residue was purified by pre-TLC to give CA (3 mg, 29.6% yield) as white solid. $^1$H NMR, (400 MHz, DMSO-d6): δ=11.91 (br s, 1H), 4.30 (d, J=4.39, 1H), 4.10 (d, J=3.51, 1H), 3.99 (d, J=3.26, 1H), 3.79 (br d, J=2.64, 1H), 3.62 (br s, 1H), 3.23-3.14 (m, 1H), 2.27-2.06 (m, 5H), 1.82-1.63 (m, 6H), 1.41-1.13 (m, 11H), 1.01-0.96 (m, 1H), 0.92 (d, J=6.4, 3H), 0.88-0.84 (m, 1H), 0.81 (s, 3H), 0.59 (s, 3H). $^{13}$C NMR, (100 MHz, DMSO-d6): δ=175.45, 71.45, 70.90, 66.71, 46.56, 46.22, 41.99, 41.84, 35.78, 35.52, 35.34, 34.86, 31.31, 31.27, 30.88, 29.01, 27.75, 26.68, 23.27, 23.10, 17.41, 12.81.
Example 2
Synthesis of Cholic Acid from DHEA: Route 2
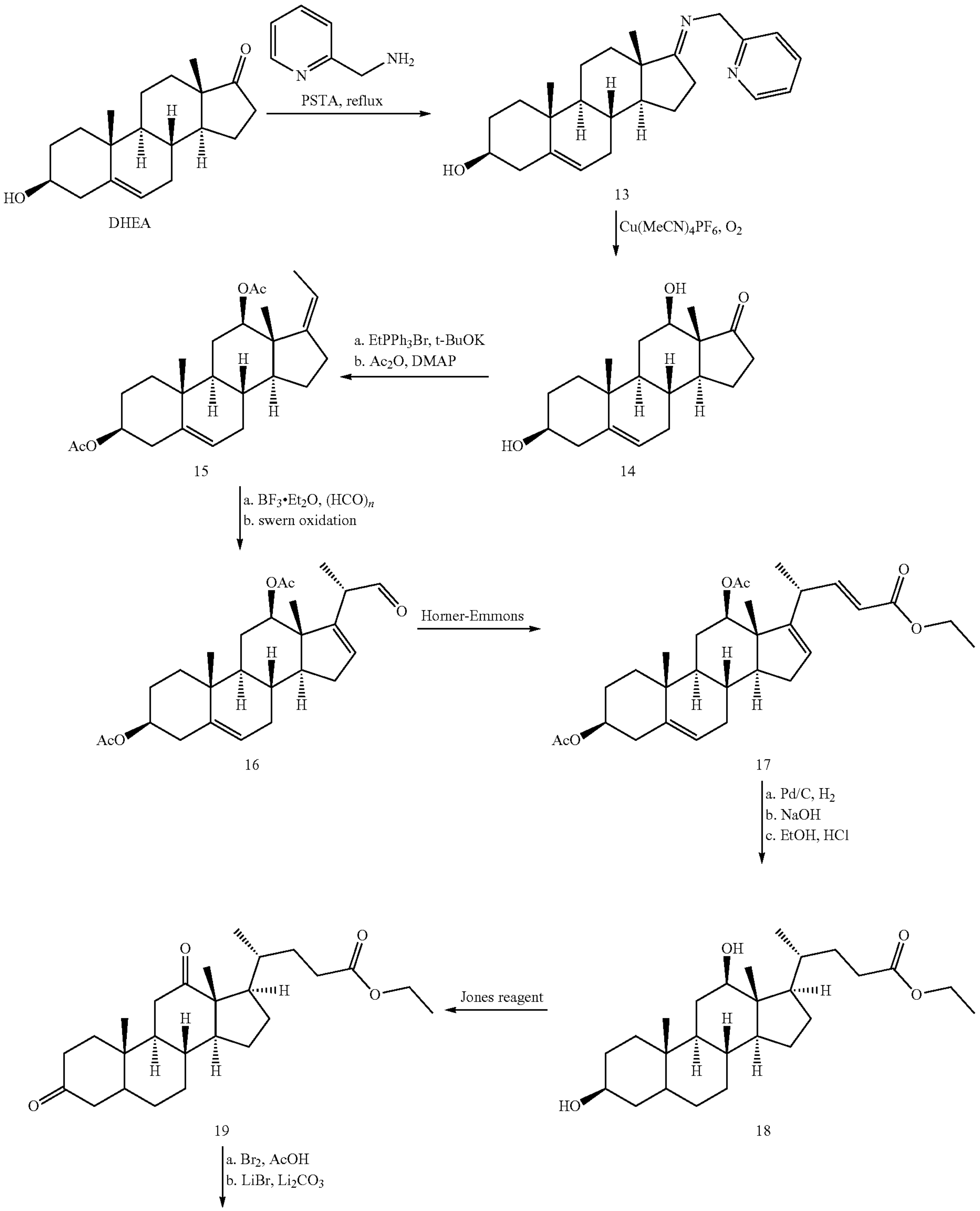

-continued

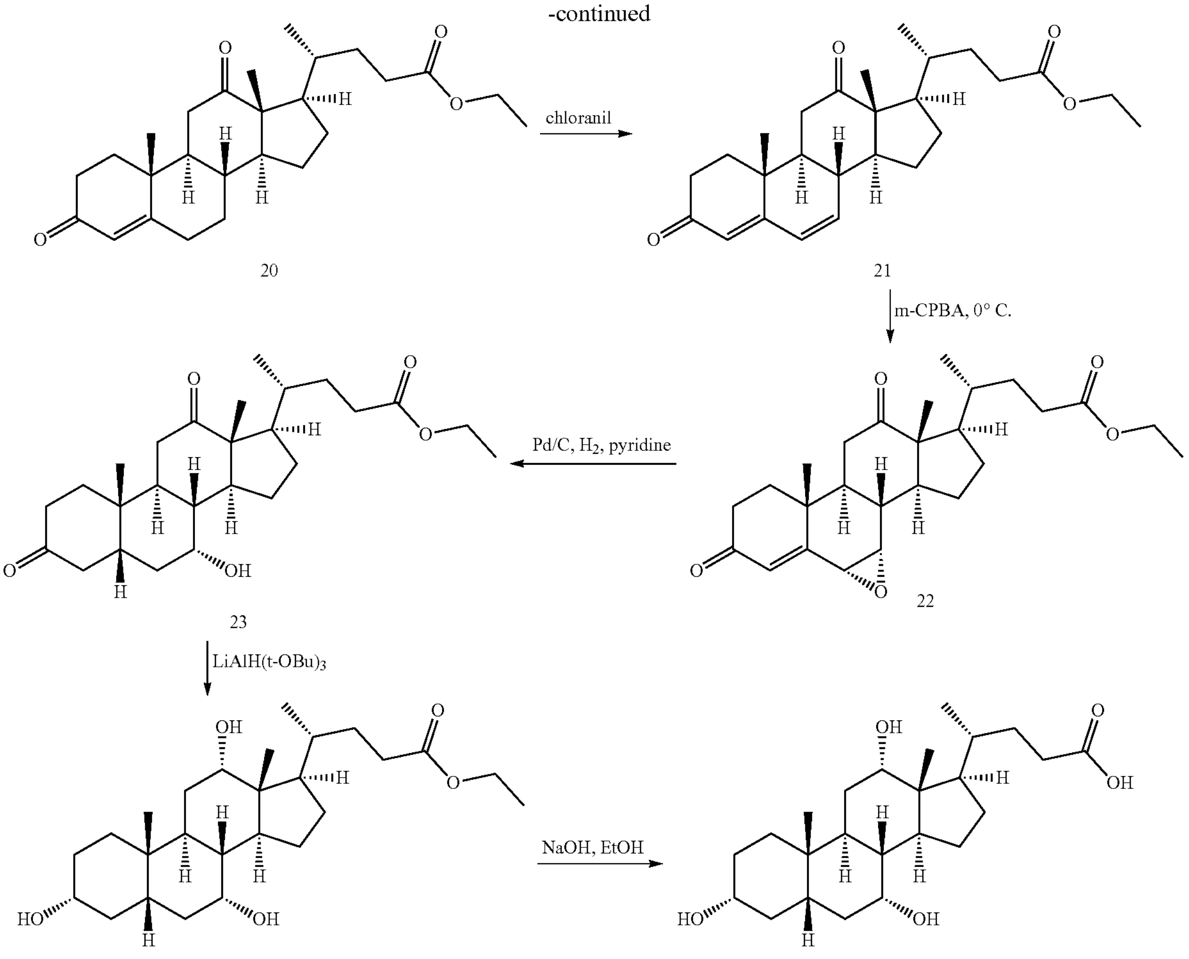

20, 21, 22, 23, 24, Cholic acid

Step 1

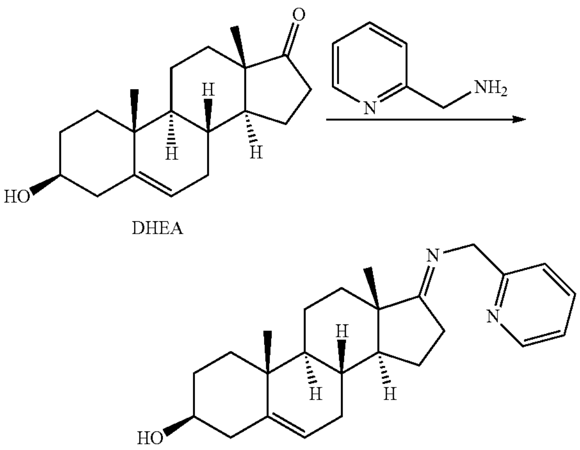

DHEA

13

To a mixture of DHEA (20.00 g, 69.34 mmol, 1.00 eq) and 2-pyridylmethanamine (37.49 g, 346.70 mmol, 35.37 mL, 5.00 eq) in toluene (250.00 mL) was added PTSA (358.23 mg, 2.08 mmol, 0.03 eq) at 25° C., the mixture was stirred at 120° C. for 2 hrs with Dean-Stark apparatus. Then the reaction mixture was diluted with EA (400 ml), washed with saturated $NaHCO_3$ (100 ml*2) and water (100 ml*2). The organic layer was concentrated. The residue was triturated by EA (30 ml) at 25° C. to afford Compound 13 (23.40 g, 57.80 mmol, 83.36% yield, 93.5% purity) as white solid. $^1$H NMR, (400 MHz, $CDCl_3$): δ=8.54 (d, J=4.1 Hz, 1H), 7.67 (dt, J=1.7, 7.7 Hz, 1H), 7.45 (d, J=7.8 Hz, 1H), 7.19-7.11 (m, 1H), 5.40 (br d, J=4.9 Hz, 1H), 4.70-4.53 (m, 2H), 3.63-3.48 (m, 1H), 2.54-2.43 (m, 1H), 2.38-2.25 (m, 3H), 2.15-2.03 (m, 2H), 1.96-1.85 (m, 3H), 1.75-1.70 (m, 1H), 1.64-1.36 (m, 6H), 1.26-1.10 (m, 2H), 1.07 (s, 3H), 1.03 (br d, J=4.5 Hz, 1H), 0.94 (s, 3H).

Step 2

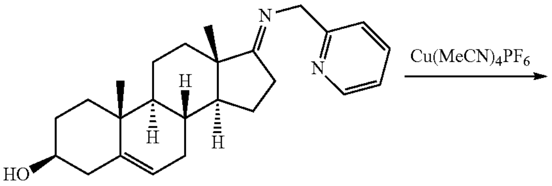

13

-continued

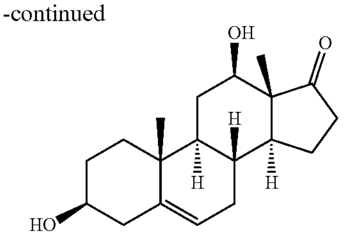

14

To a solution of compound 13 (6.00 g, 15.85 mmol, 1.00 eq) in acetone (60.00 mL) and MeOH (60.00 mL) was added sodium ascorbate (6.28 g, 31.70 mmol, 2.00 eq) and $Cu(MeCN)_4PF_6$ (8.27 g, 22.19 mmol, 1.40 eq) in sequence at 25° C. After stirred at 25° C. for 5 mins, oxygen (15 psi) was bubbled through the reaction mixture for 10 mins. Then the reaction was heated to 50° C. and stirred at 50° C. for 2 hrs under $O_2$ atmosphere. After cooled to 25° C., EA (300 mL) and saturated EDTA-$Na_4$ (100 mL) was added, the mixture was stirred at 25° C. for 30 mins. The organic phase was separated and concentrated in vacuo. The residue was purified by column chromatography (PE/EA=15/1 to 5/1) to afford Compound 14 (2.40 g, 7.88 mmol, 49.74% yield) as white solid. $^1$H NMR, (400 MHz, $CDCl_3$): δ=5.43-5.38 (m, 1H), 3.88-3.79 (m, 1H), 3.59-3.51 (m, 1H), 3.09 (s, 1H), 2.51 (dd, J=8.4, 19.4 Hz, 1H), 2.40-2.33 (m, 1H), 2.31-2.22 (m, 1H), 2.20-2.09 (m, 2H), 2.08-1.97 (m, 1H), 1.93-1.86 (m, 2H), 1.76-1.63 (m, 3H), 1.56-1.45 (m, 3H), 1.33-1.24 (m, 1H), 1.20-1.09 (m, 2H), 1.07 (s, 3H), 0.99 (s, 3H).

Step 3

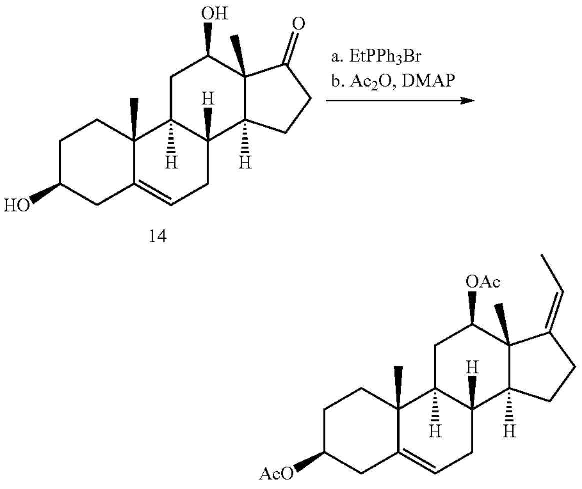

14

15

$EtPPh_3Br$ (12.18 g, 32.80 mmol, 10.00 eq) in a flask was dried under high vacuum for 1 hr at 70° C. Dry THF (100.00 mL) was added, followed by adding t-BuOK (3.68 g, 32.80 mmol, 10.00 eq) under N2. The entire mixture was still stirred at 70° C. for 0.5 hr under $N_2$. The solution of Compound 14 (1.00 g, 3.28 mmol, 1.00 eq) in dry THF (5.00 mL) was added to the reaction at 70° C., the reaction was stirred at 70° C. for another 2 hrs. TLC showed the starting material was all consumed and one new main spot was formed. After cooling to room temperature, the solution was diluted by EA (100 mL), quenched by saturated $NH_4Cl$ solution (30 mL). The aqueous solution was extracted with EA (50 mL*2), the combined organic layers were washed with brine (40 mL), dried over $Na_2SO_4$ and filtered, concentrated in vacuum to give 1.04 g light yellow oil.

The obtained light yellow oil (1.04 g, 3.29 mmol, 1.00 eq) was dissolved in DCM (20.00 mL) at 25° C., followed by adding Ac2O (752.36 mg, 7.37 mmol, 690.24 uL, 2.24 eq), $Et_3N$ (2.00 g, 19.74 mmol, 2.74 mL, 6.00 eq) and DMAP (80.39 mg, 658.00 umol, 0.20 eq) at 25° C. The reaction was stirred at 25° C. for 3 hrs. TLC showed the starting material was consumed completely and one new main spot was formed. The reaction was diluted with EA (100 ml), washed with $H_2O$ (50 mL), dried over $Na_2SO_4$ and filtered, the organic layer was concentrated in vacuo. The residue was purified with column chromatography (PE/EA=30/1 to 20/1) to give Compound 15 (1.14 g, 2.62 mmol, 79.59% yield, 92% purity) as off-white oil. $^1$H NMR, (400 MHz, $CDCl_3$): δ=5.41 (d, J=5.0 Hz, 1H), 5.31-5.19 (m, 1H), 4.91 (dd, J=5.0, 10.9 Hz, 1H), 4.68-4.57 (m, 1H), 2.46-2.19 (m, 4H), 2.12-2.08 (m, 3H), 2.07-2.04 (m, 3H), 1.98 (td, J=4.9, 13.0 Hz, 1H), 1.91-1.81 (m, 2H), 1.72-1.65 (m, 1H), 1.65-1.61 (m, 3H), 1.60-1.41 (m, 5H), 1.37-1.12 (m, 4H), 1.05 (s, 3H), 1.02 (s, 3H). Mass (m/z): 423.2 ($M^+$+23).

Step 4

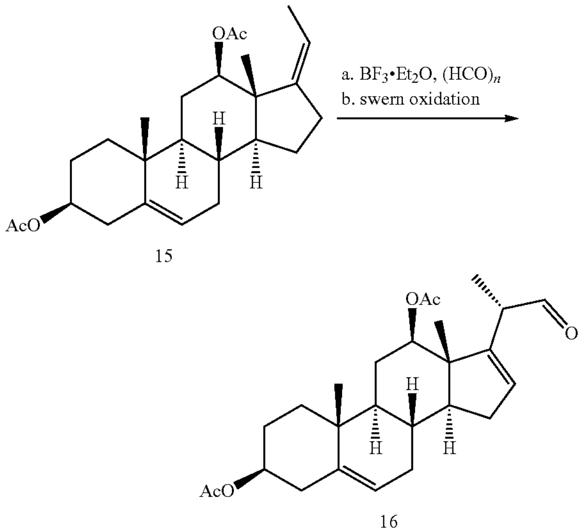

15

16

To a solution of compound 15 (1.12 g, 2.80 mmol, 1.00 eq) in DCM (100.00 mL) was added paraformaldehyde (2.7 g, 29.96 mmol, 10.7 eq) in one portion at 0° C., followed by adding $BF_3.Et_2O$ (39.74 mg, 280.00 umol, 34.56 uL, 0.10 eq) at 0° C. The mixture was warmed to 25° C. and stirred at 25° C. for 2 hrs. TLC showed one new spot was formed. The reaction mixture was quenched by $H_2O$ (15 ml), extracted with DCM (10 ml*3), dried with anhydrous $Na_2SO_4$, filtered and concentrated in vacuum. The residue was purified by silica gel chromatography (PE:EA=30:1 to 15:1) to afford 860 mg white solid.

To a flask was added oxalyl chloride (278.87 mg, 2.20 mmol, 192.32 uL, 1.10 eq) and DCM (20.00 mL) at 15° C. The reaction was cooled to −78° C. and it was stirred at −78° C. for 15 mins. Then, DMSO (312.10 mg, 3.99 mmol, 312.10 uL, 2.00 eq) was added drop-wise to the reaction at −78° C. The mixture was stirred at −78° C. for 15 mins. The solution of previous obtained white solid (860.00 mg, 2.00 mmol, 1.00 eq) in DCM (3.00 mL) was added into the reactor at −78° C. The mixture was stirred at −78° C. for another 15 mins. Then TEA (1.01 g, 9.99 mmol, 1.38 mL, 5.00 eq) was added drop-wise at −78° C. The resulting mixture was stirred at −78° C. for 15 mins and at 15° C. for 30 mins, TLC showed one new main spot was formed, the reaction was quenched with $H_2O$ (5 mL), extracted with DCM (15 mL). The organic phase was washed with brine (50 mL*2), dried with anhydrous $Na_2SO_4$, filtered and concentrated in vacuum, which was purified by column chromatography (SiO2, PE:EA=60:1 to 30:1) to afford Compound 16 (510 mg, 59.5% yield) as a white solid.

Step 5

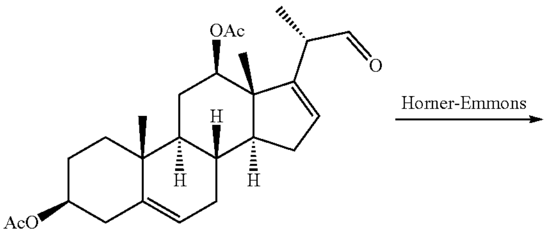

16

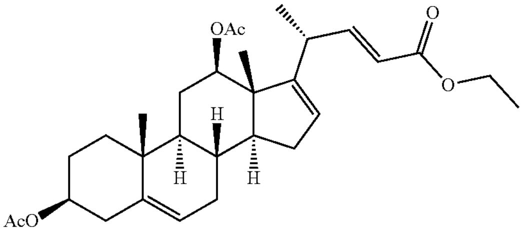

17

To a solution of NaH (476.00 mg, 11.90 mmol, 60% purity, 10.00 eq) in THF (10.00 ml) was added ethyl 2-diethoxyphosphorylacetate (2.67 g, 11.90 mmol, 2.36 mL, 10.00 eq) at 25° C., the reaction mixture was stirred at 25° C. for 30 mins. A solution of Compound 16 (510.00 mg, 1.19 mmol, 1.00 eq) in THF (2.00 mL) was added to the reaction at 25° C. and it was stirred at 25° C. for 2 hrs. TLC showed the starting material was all consumed. Saturated $NH_4Cl$ (15 mL) was added into the reactor to quench the reaction. The mixture was extracted with EA (50 mL*3), the organic layer was washed with brine (100 mL*2), dried with anhydrous $Na_2SO_4$, filtered and concentrated in vacuum. The residue was purified by column chromatography (PE:EA=50/1 to 30:1) to afford compound 17 as colorless oil (720.00 mg, 929.00 umol, 78.07% yield, 64.34% purity by $^1$H NMR). $^1$H NMR, (400 MHz, $CDCl_3$): δ=7.01 (dd, J=6.9, 15.7 Hz, 1H), 5.80 (dd, J=1.3, 15.7 Hz, 1H), 5.45 (br s, 1H), 5.42 (br d, J=5.0 Hz, 1H), 4.93 (dd, J=5.1, 10.7 Hz, 1H), 4.67-4.58 (m, 1H), 4.21 (q, J=7.2, 14.7 Hz, 2H), 3.12 (q, J=6.7 Hz, 1H), 2.42-2.27 (m, 2H), 2.19-2.12 (m, 1H), 2.10 (s, 3H), 2.05 (s, 3H), 2.04-1.77 (m, 5H), 1.69-1.64 (m, 1H), 1.60-1.52 (m, 1H), 1.51-1.39 (m, 2H), 1.37 (t, J=7.1, 3H), 1.29-1.27 (m, 1H), 1.26-1.17 (m, 2H), 1.14 (d, J=6.8 Hz, 3H), 1.07 (s, 3H), 0.95 (s, 3H). Mass (m/z): 521.2 ($M^+$+23).

Step 6

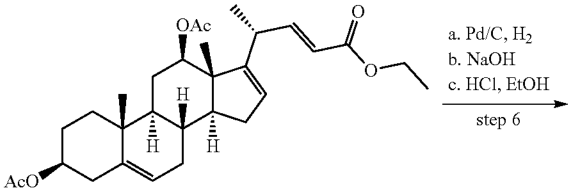

17

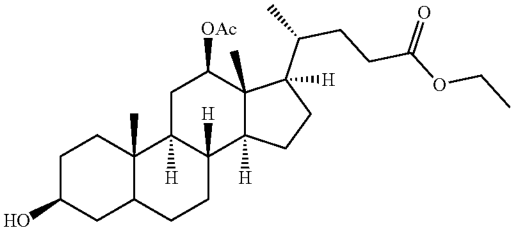

18

To a solution of compound 17 (660.00 mg, 1.32 mmol, 1.00 eq) in MeOH (150.00 mL) was added Pd/C (10%, 70 mg) at 15° C. The suspension was degassed under vacuum and purged with $H_2$ several times. The reaction was heated to 25° C. and stirred at 25° C. for 12 hours under $H_2$ (50 psi). LCMS showed the starting material was consumed completely. The reaction mixture was filtered and the filtrate was concentrated to give 450.00 mg white solid.

To a mixture of obtained white solid (350.00 mg, 693.48 umol, 1.00 eq) in EtOH (10.00 mL) was added NaOH (332.87 mg, 8.32 mmol, 12.00 eq) in one portion at 15° C. under $N_2$. The mixture was heated to 30° C. and stirred at 30° C. for 2 hrs. LCMS showed the starting material was all consumed, but no target mass was found. Another batch of NaOH (221.92 mg, 5.55 mmol, 8.00 eq) was added at 15° C., the mixture was keep stirred at 30° C. for another 4 hrs. LCMS showed all the starting material was consumed and desired mass was found. The mixture was concentrated in reduced pressure to remove solvent. Aqueous HCl (1N, 10 ml) was added to the residue to adjust to PH=4, and then extracted with EA (50 mL*3). The organic layer was washed with brine (10 mL*2), dried with anhydrous $Na_2SO_4$, filtered and concentrated in vacuum to afford white solid (260.00 mg, 662.30 umol, 95.50% yield).

The obtained white solid (260.00 mg) was dissolved in EtOH (15.00 mL) at 15° C., followed by adding HCl (153.00 mg, 4.20 mmol, 150.00 uL, 6.34 eq) at 15° C. The reaction mixture was heated to 80° C. and stirred at 80° C. for 30 mins. TLC showed the starting material was all consumed and two new spots were formed. The reaction was concentrated in vacuum, which was purified by column chromatography (SiO2, PE:EA=4:1 to 2:1) to give compound 18 (176 mg) as white solid. $^1$H NMR, (400 MHz, $CDCl_3$): δ=4.14 (q, J=7.1 Hz, 2H), 3.66-3.54 (m, 1H), 3.41 (dd, J=4.7, 11.0 Hz, 1H), 2.44-2.33 (m, 1H), 2.31-2.18 (m, 1H), 1.99-1.89 (m, 1H), 1.88-1.79 (m, 2H), 1.76-1.67 (m, 4H), 1.64-1.59 (m, 2H), 1.54-1.42 (m, 4H), 1.33-1.30 (m, 3H), 1.30-1.27 (m, 5H), 1.26-1.16 (m, 3H), 1.15-1.09 (m, 1H), 1.03 (d, J=6.8 Hz, 3H), 0.98-0.86 (m, 2H), 0.83 (s, 3H), 0.74 (s, 3H). Mass (m/z): 443.3 ($M^+$+23).

Step 7

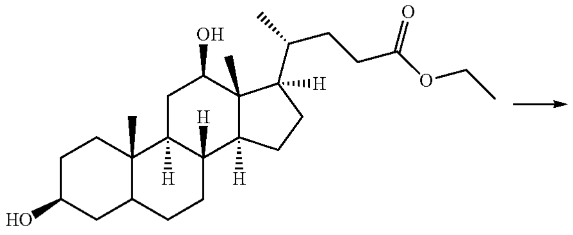

18

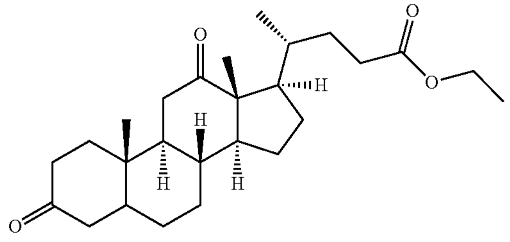

19

Compound 18 (50 mg, 118.87 umol, 1.0 eq) was dissolved in acetone (2.50 mL) at 15° C., and then Jones reagent (150.00 uL) was added drop-wise to the solution until a yellow color persisted. The mixture was stirred at 15° C. for another 15 mins. TLC indicated desired product was formed. i-PrOH (10 ml) was added drop-wise and stirred 10 mins to quench the remaining Jones reagent. Then, $H_2O$ (10 mL) was added the reaction mixture, and it was extracted with EA (50 mL*2). The combined organic phase was washed with brine (15 mL), dried with anhydrous $Na_2SO_4$, filtered and concentrated in vacuum. The residue was purified by column chromatography (PE:EA=50/1, 10/1) to afford compound 19 (30.00 mg, 72.01 umol, 60.58% yield) as a white solid. $^1H$ NMR, (400 MHz, DMSO): δ=4.05 (q, J=7.2 Hz, 2H), 2.55 (t, J=12.7 Hz, 1H), 2.36-2.23 (m, 3H), 2.22-2.10 (m, 3H), 2.10-2.03 (m, 1H), 2.00-1.85 (m, 2H), 1.85-1.63 (m, 5H), 1.50-1.42 (m, 1H), 1.38-1.25 (m, 7H), 1.21-1.16 (m, 4H), 1.15-1.09 (m, 1H), 1.03 (s, 3H), 0.99 (s, 3H), 0.92-0.84 (m, 1H), 0.79 (d, J=6.5 Hz, 3H). Mass (m/z): 417.3 ($M^+$+1).

Step 8

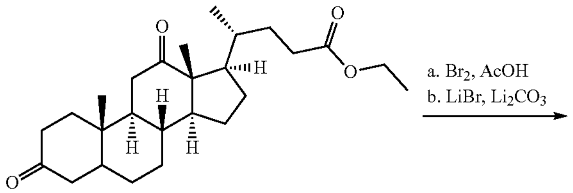

19

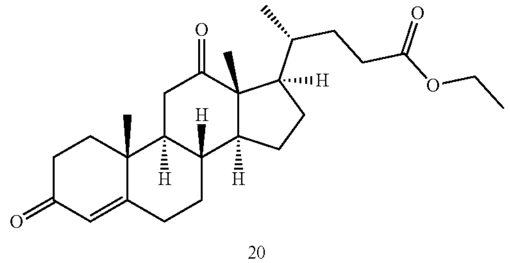

20

To a 1000 ml flask was added 19 (20.00 g, 48.01 mmol, 1.00 eq) and AcOH (300.00 mL). The reaction was cooled to 0° C., and then fresh prepared $Br_2$ (7.67 g, 48.01 mmol, 2.47 mL, 1.00 eq) in AcOH (60.00 mL) was added to the reaction drop-wise. After addition, the reaction was warmed to 20° C., and stirred at 20° C. for 0.5 hour. Then, the reaction was diluted with EA (200 ml), washed with water (200 ml) and saturated $NaHCO_3$ (3*200 ml). The organic layer was concentrated in vacuo to give 20 g crude oil residue.

The oil residue (20.00 g) was added to a 1000 ml flask, DMF (500.00 mL) was added to the flask to prepare a solution, followed by adding $Li_2CO_3$ (12.61 g, 170.72 mmol, 4.23 eq) and LiBr (6.20 g, 71.44 mmol, 1.79 mL, 1.77 eq) to the reaction mixture. Then the reaction was heated to 150° C., and it was stirred at 150° C. for 2 hrs. After TLC (PE/EA=2/1) showed the reaction was completed, the reaction was concentrated in vacuo, diluted with EA (500 ml), washed with water (500 ml), and the organic layer was concentrated in vacuo to give oil residue. The residue was purified by column chromatography to give compound 20 (5.4 g, 32% yield). $^1H$ NMR, (400 MHz, MeOD): δ=5.69 (s, 1H), 4.06 (q, J=7.1 Hz, 2H), 2.58 (t, 1H), 2.43-2.09 (m, 7H), 1.99-1.61 (m, 8H), 1.35-1.24 (m, 6H), 1.20 (s, 3H), 1.09 (t, J=8.0 Hz, 3H), 1.02 (s, 3H), 1.06-0.93 (m, 1H), 0.80 (d, J=6.4 Hz 3H). Mass (m/z): 415.1 ($M^+$+1).

Step 9

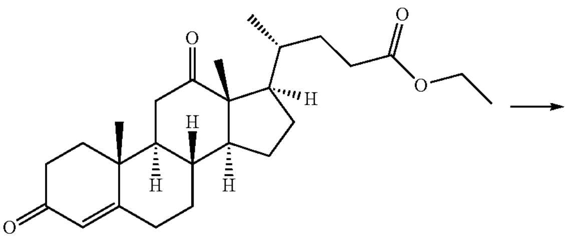

20

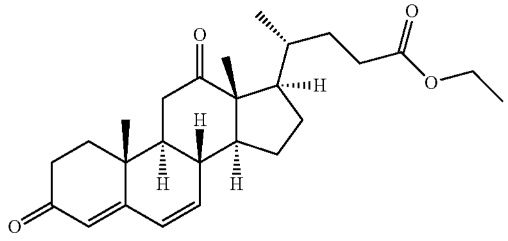

21

To a 100 ml flask was added compound 20 (1.00 g, 2.41 mmol, 1.00 eq), AcOH (10.00 mL) and toluene (1.00 mL). 2,3,5,6-tetrachloro-1,4-benzoquinone (889.62 mg, 3.62 mmol, 1.50 eq) was added to the reaction mixture at rt. The reaction was heated to 120° C., and it was stirred at 120° C. for 2 hrs. After LCMS showed the reaction was completed, it was diluted with EA (100 ml), washed with water (100 ml) and saturated $NaHCO_3$ (2*100 ml). The organic layer was concentrated in vacuo to give yellow oil residue. The residue was purified by column chromatography to give compound 21 (650 mg, 89% purity, 58% yield) as white solid. $^1H$ NMR, (400 MHz, $CDCl_3$): δ=6.20-6.12 (m, 2H), 5.74 (s, 1H), 5.41 (s, 1H), 4.16 (q, J=7.1, 2H), 2.73-1.32 (m, 19H), 1.28 (t, J=7.1, 3H), 1.22 (s, 3H), 1.15 (s, 3H), 0.90 (d, J=6.3, 3H). Mass (m/z): 413.1 ($M^+$+1).

Step 10

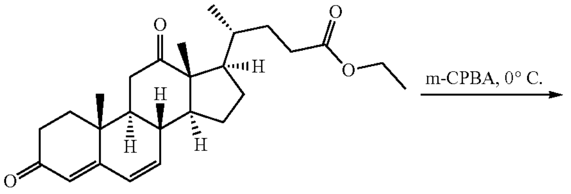

21

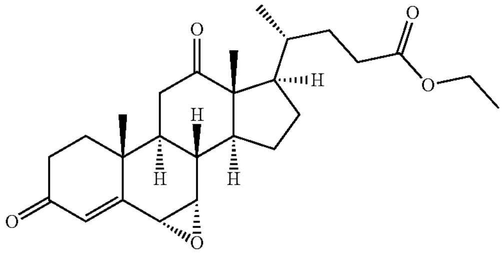

22

To a 100 ml flask was added compound 21 (2.50 g, 6.06 mmol, 1.00 eq) and DCM (60.00 mL). The reaction was cooled to 0° C., m-CPBA (2.09 g, 8.48 mmol, 70% purity, 1.40 eq) was added to the flask at 0° C., and it was stirred at 0° C. for 48 hrs. After TLC (PE/EA=2/1) showed the reaction was completed, it was diluted with DCM (100 ml), washed with saturated $Na_2SO_3$ (2*60 ml), the organic layer was concentrated in vacuo. The residue was purified by column chromatography (basified by TEA) to give compound 22 (1.0 g, 38% yield) as white solid. $^1H$ NMR, (400 MHz, $CDCl_3$): δ=6.08 (s, 1H), 4.06 (q, J=7.09, 2H), 3.43 (d, J=3.67, 1H), 3.36 (d, J=3.55, 1H), 2.53-1.25 (m, 19H), 1.19 (t, J=7.15, 3H), 1.11 (s, 3H), 1.03 (s, 3H), 0.81 (d, J=7.15, 3H). Mass (m/z): 429.2 ($M^+$+1).

Step 11

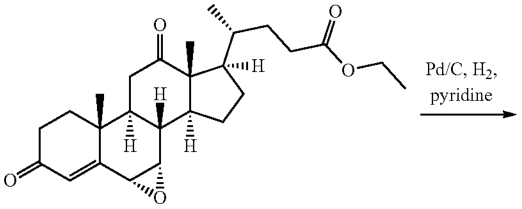

22

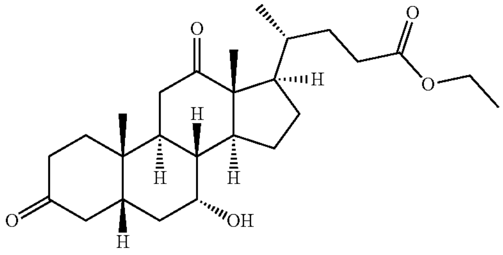

23

To a pressure tube was added compound 22 (110.00 mg, 256.67 umol, 1.00 eq), Py (6.00 mL) and Pd/C (50.00 mg, 256.67 umol, 1.00 eq). The reaction was purged with $H_2$ (50 psi) gas and stirred at 20° C. for 16 hrs. LCMS showed the reaction was completed. The reaction was filtered, the filtrate was concentrated in vacuo to give compound 23 (100 mg, crude) as yellow oil. Mass (m/z): 433.3 ($M^+$+1).

Step 12

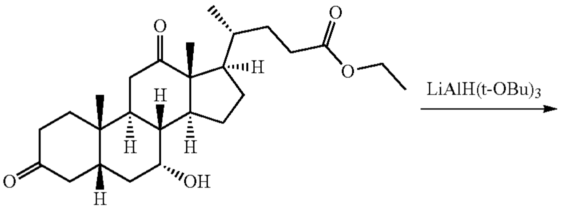

23

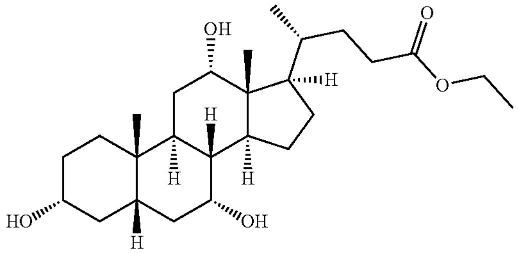

24

To a 35 ml flask was added compound 23 (100 mg, crude) and THF (10 ml). $LiAlH(t\text{-}OBu)_3$ (117.09 mg, 462.33 umol, 130.10 uL, 2.00 eq) was added to the flask at 20° C., and it was stirred at 20° C. for 5 hours. After TLC (PE/EA=1/3) showed the reaction was completed, the reaction was quenched by saturated $NH_4Cl$ (20 ml), diluted with EA (100 ml), and washed with water (50 ml). The organic layer was concentrated in vacuo to give compound 24 (100 mg, crude) as colorless oil. Mass (m/z): 459.3 ($M^+$+23).

Step 13

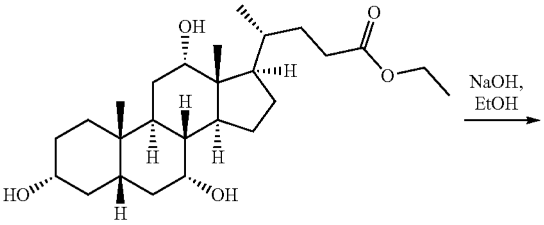

24

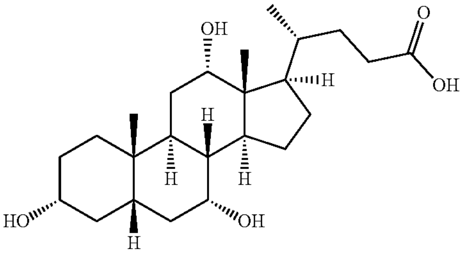

Cholic acid

To a 35 ml tube was added compound 24 (100 mg, crude) and EtOH (2 ml), followed by adding NaOH (36.64 mg, 916.12 umol, 4.00 eq) to the reaction at 30° C. The resulting mixture was stirred at 30° C. for 1 hour. After TLC (AcOH/EA=1/50) the desired product was found, the reaction was concentrated in vacuo to remove solvent, the residue was diluted with water (5 ml), acidized by conc. HCl to pH=3, and then extracted with EA (3*20 ml). The organic layer was concentrated in vacuo, the resulting residue was purified by pre-TLC (AcOH/EA=1/50) to give CA (15 mg) as white solid. $^{1}$H NMR, (400 MHz, $CDCl_3$): δ=11.94 (br s, 1H), 4.33 (d, J=4.27, 1H), 4.13 (d, J=3.51, 1H), 4.02 (d, J=3.39, 1H), 3.79 (br d, J=2.76, 1H), 3.62 (br s, 1H), 3.22-3.16 (m, 1H), 2.27-2.02 (m, 5H), 1.78-1.44 (m, 6H), 1.47-1.13 (m, 11H), 1.01-0.96 (m, 1H), 0.93 (d, J=6.4, 3H), 0.88-0.84 (m, 1H), 0.81 (s, 3H), 0.59 (s, 3H). Mass (m/z): 817.6 ($2M^{+}$+1).
Example 3
Synthesis of Cholic Acid from Ac-DHEA
Step 1
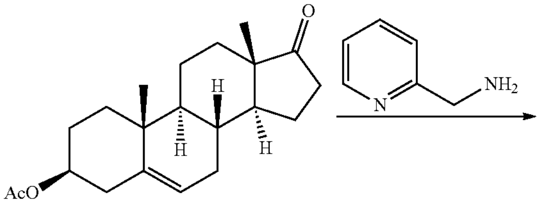
Ac-DHEA
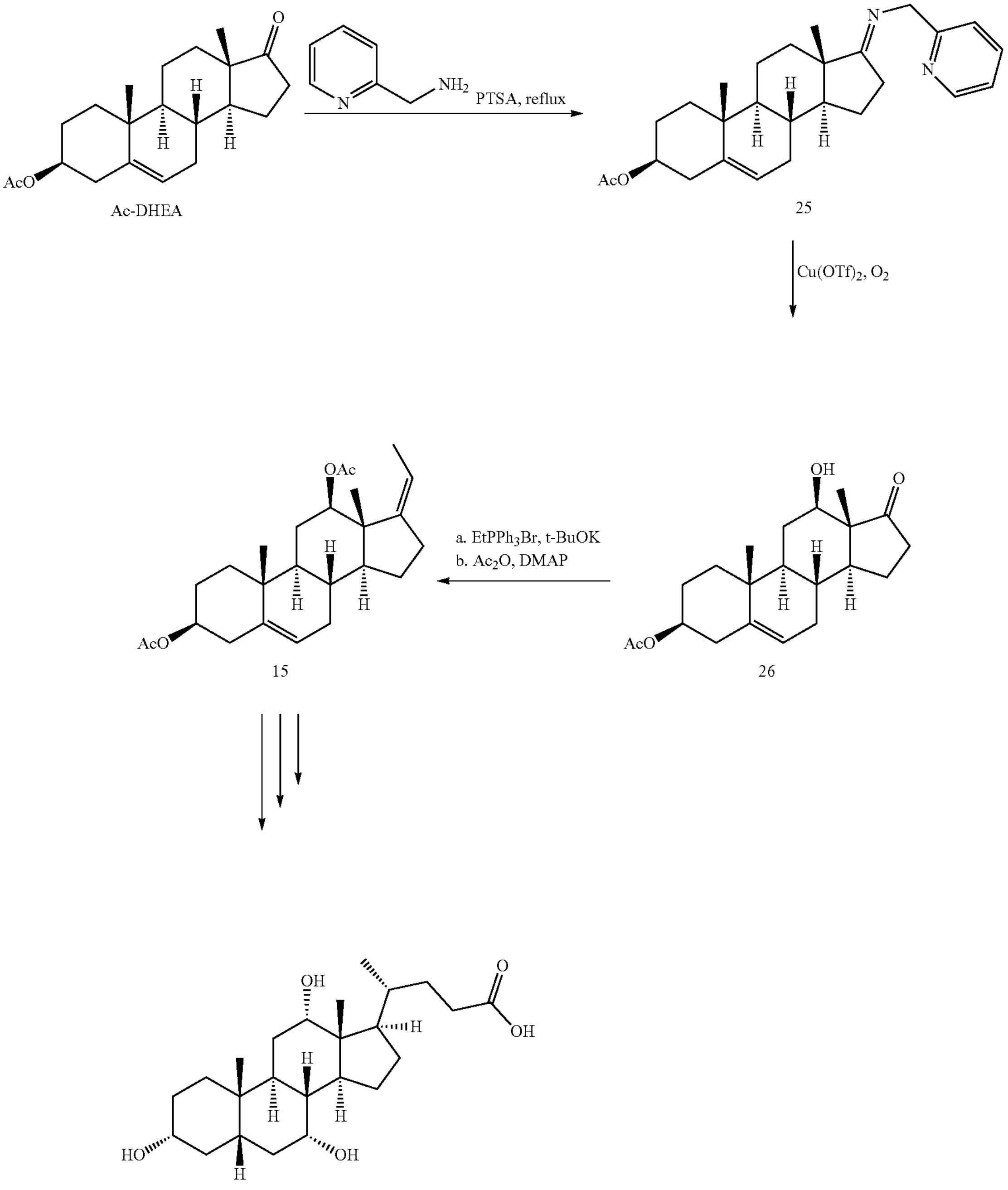
Ac-DHEA
25
26
15
Cholic acid -continued

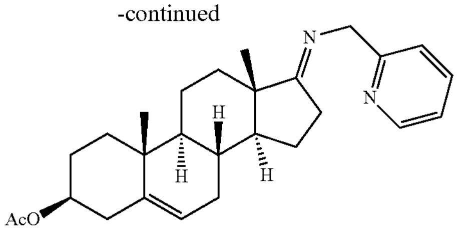

25

To a flask was added Ac-DHEA (50 g, 151.30 mmol, 1.0 eq) and toluene (1 L), 2-pyridylmethanamine (37.49 g, 346.72 mmol, 35.37 ml, 5.0 eq) was added to the reaction at 15° C., followed by adding PTSA (781.64 mg, 4.54 mmol, 0.03 eq) at 15° C. The reaction was heated to 110° C. with Dean-Stark apparatus for 2 hours. The reaction was cooled to 15° C., EA (1 L) was added to the reaction. The resulting mixture was washed with saturated $NaHCO_3$ (2*100 ml) and water (2*100 ml). The organic layer was concentrated in vacuo. The residue was re-crystallized by EA (65 ml) to give compound 25 (54.0 g, 84.86% yield) as light yellow solid.

Step 2

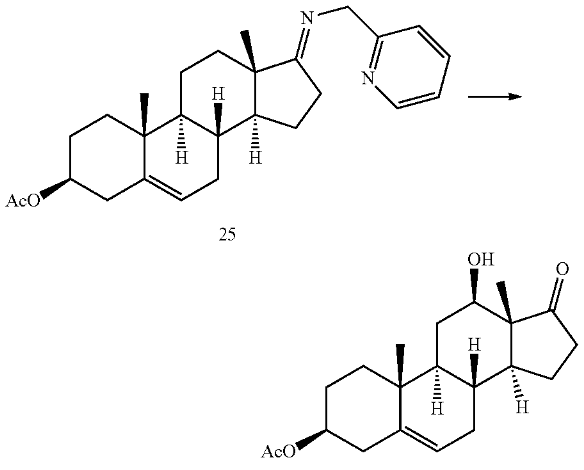

25

26

To a 100 ml flask was added compound 25 (10 g, 23.78 mmol, 1.00 eq) sodium ascorbate (9.42 g, 47.55 mmol, 2.00 eq) and $Cu(OTf)_2$ (19.78 g, 54.69 mmol, 2.30 eq) at 25° C. Acetone (90 mL) and MeOH (90 mL) was added to the flask to prepare a solution. After stirred at 25° C. for 5 mins, $O_2$ (15 psi) was bubbled through the reaction mixture for 5 mins. Then, the reaction was heated to 50° C., and it was stirred at 50° C. for 1.5 hrs. TLC (PE/EA=2/1) showed most of starting material was consumed, and a main new spot was found. The reaction was cooled to 25° C. EA (100 ml) and saturated EDTA-$Na_4$ (100 ml) was added to the reaction and stirred for 1 hour. The resulting mixture was concentrated in vacuo to remove organic solvent. The aqueous layer was extracted with EA (3*150 ml). The combined organic layer concentrated in vacuo. The residue was purified by flash column chromatography (PE/EA=20/1 to 2/1) to give compound 26 (6.2 g, 71.5% yield) as white solid. $^1H$ NMR, (400 MHz, $CDCl_3$): δ=5.43 (d, 1H), 4.66-4.59 (m, 1H), 3.87-3.79 (m, 1H), 3.08 (s, 1H), 2.50 (dd, J=8.8, 19.5 Hz, 1H), 2.46-2.37 (m, 2H), 2.15-2.05 (m, 2H), 2.05 (s, 3H), 2.03-2.01 (m, 1H), 1.91-1.85 (m, 3H), 1.71-1.60 (m, 3H), 1.52-1.30 (m, 1H), 1.29-1.13 (m, 3H), 1.08 (s, 3H), 0.98 (s, 3H).

Step 3

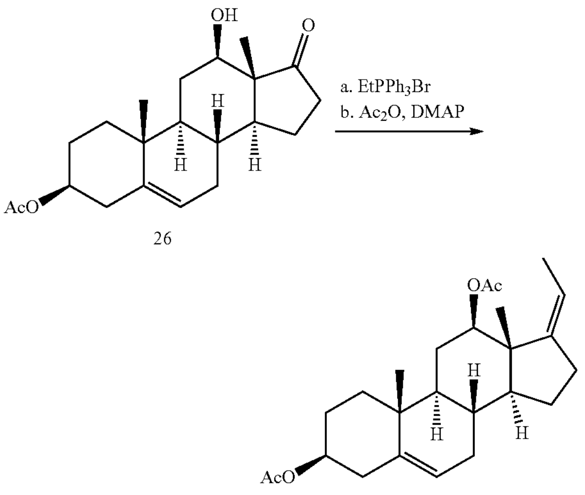

26

15

To a 250 ml tube was added $EtPPh_3Br$ (26.63 g, 71.74 mmol, 5.00 eq) at 20° C., and it was purged with $N_2$ gas. t-BuOK (8.05 g, 71.74 mmol, 5.00 eq) and THF (100 mL) was added to the flask at 20° C. The mixture was heated to 70° C., and it was stirred at 70° C. for 0.5 hr. Compound 26 (5 g, 14.35 mmol, 1.00 eq) was added to the reaction at 70° C., and it was stirred at 70° C. for another 2 hrs. TLC (PE/EA=2/1) showed all the starting material was consumed, and a new spot was formed. The reaction was diluted with EA (250 ml), quenched by water (100 ml) and separated. The aqueous layer was extracted with EA (2*50 ml). The combined organic layer was concentrated in vacuo to give 9 g of crude product as yellow oil.

To a 250 ml flask was added the yellow oil previous obtained (9 g, crude). DCM (75 mL) was added to the flask to prepare a solution. Ac2O (2.80 g, 27.46 mmol, 2.57 mL, 2 eq) was added to the flask at 20° C. DMAP (167.74 mg, 1.37 mmol, 0.1 eq) and $Et_3N$ (5.56 g, 54.92 mmol, 7.64 mL, 4 eq) was added to the flask at 20° C. The reaction was stirred at 20° C. for 16 hrs. TLC (PE/EA=5/1) showed all the starting material was consumed, and a new spot was formed. The reaction was diluted with DCM (100 ml), washed with water (50 ml) and separated. The organic layer was concentrated in vacuo. The residue was purified by flash column chromatography (PE/EA=20/1 to 10/1) to give compound 15 (3.7 g, 66.9% yield), which can be converted into cholic acid by following the sequence described in Example 2.

Example 4

Synthesis of Deoxycholic Acid

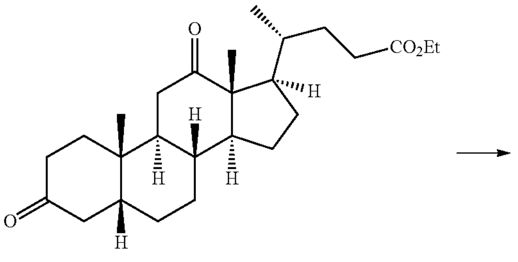

19

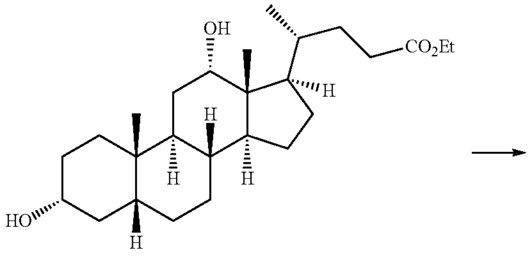

27

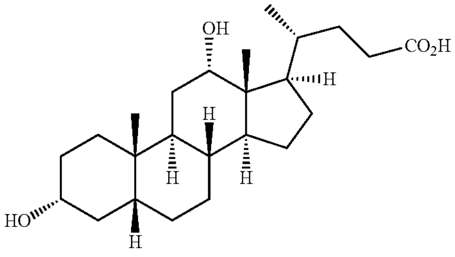

Deoxycholic acid

To a 35 ml flask is added compound 19 and THF (10 ml). $LiAlH(t\text{-}OBu)_3$ (2.00 eq) is added to the flask at 20° C., and it is stirred at 20° C. for 5 hours. After TLC (PE/EA=1/3) shows the reaction is completed, the reaction is quenched by saturated $NH_4Cl$ (20 ml), diluted with EA (100 ml), and washed with water (50 ml). The organic layer is then concentrated in vacuo to give compound 27.

To a 35 ml flask is added compound 27 and EtOH (2 ml), followed by adding NaOH (4.00 eq) to the reaction at 30° C. The resulted mixture is stirred at 30° C. for 1 hour. After TLC (AcOH/EA=1/50) shows the desired product, the reaction is concentrated in vacuo to remove solvent, the residue is diluted with water (5 ml), pH is adjusted by conc. HCl to pH=3, and then is extracted with EA (3*20 ml). The organic layer is concentrated in vacuo, the resulted residue is purified by pre-TLC (AcOH/EA=1/50) to give deoxycholic acid.

Example 5

Synthesis of Chenodeoxycholic Acid

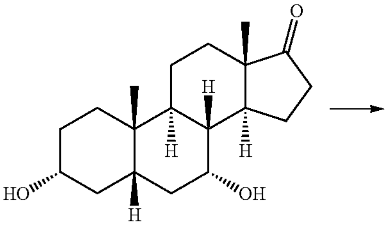

4

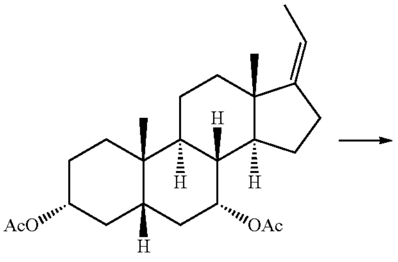

28

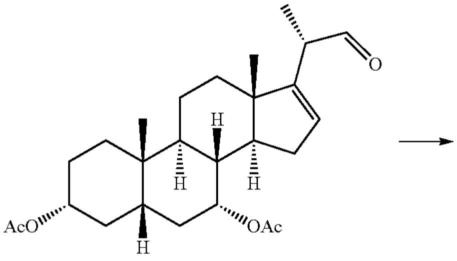

29

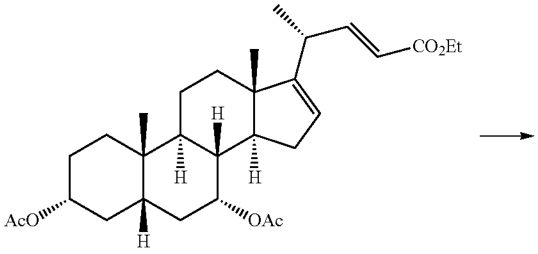

30

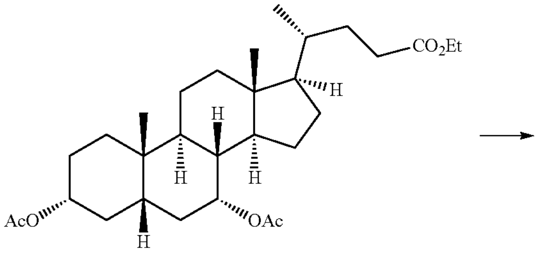

31

-continued

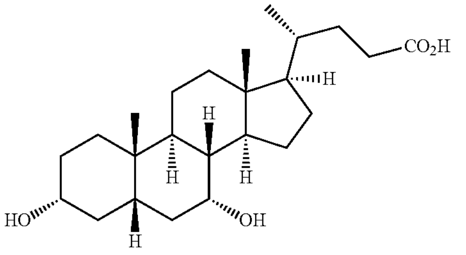

Chenodeoxyc
holic acid

Step 1

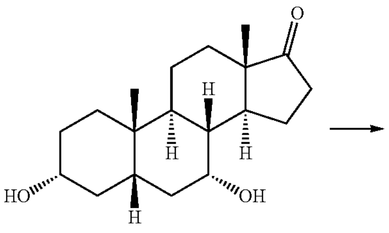

4

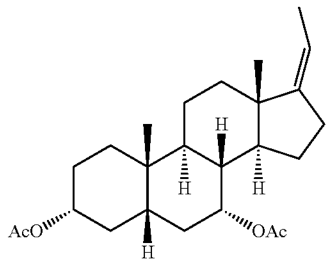

28

Compound 4, which can be obtained from DHEA following the processes described in Example 1, is firstly converted into compound 28.

Specifically, EtPPh3Br (5.00 eq) in a flask is dried under high vacuum for 1 hr at 70° C. Dry THF (3.00 mL) is added, followed by adding t-BuOK (5.00 eq) under $N_2$. The entire mixture is still stirred at 70° C. for 0.5 hr under $N_2$. The solution of Compound 4 (1.00 eq) in dry THF (2.00 mL) is added to the reaction at 70° C., the reaction is stirred at 70° C. for another 2 hrs. TLC shows the starting material is all consumed and one new spot is formed. After cooling to room temperature, the solution is diluted by EA (40 mL), quenched by saturated NaCl solution (10 mL). The aqueous solution is extracted with EA (20 mL), dried over $Na_2SO_4$, concentrated in vacuum to give an intermediate product. The intermediate product (1.00 eq) is then dissolved in DCM (5.00 mL) at 25° C., followed by adding $Ac_2O$ (4.2 eq), $Et_3N$ (6.00 eq) and DMAP (0.20 eq) at 25° C. The reaction is stirred at 25° C. for 7 hrs. The reaction is diluted with EA (50 ml), washed with $H_2O$ (10 mL), dried over $Na_2SO_4$ and filtered, the organic layer is concentrated in vacuo. The residue is purified by column chromatography to give Compound 28.

Step 2

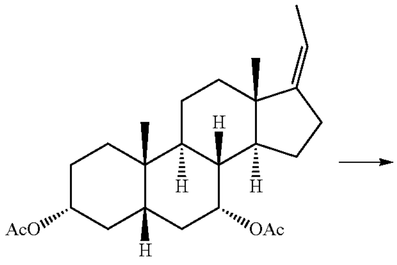

28

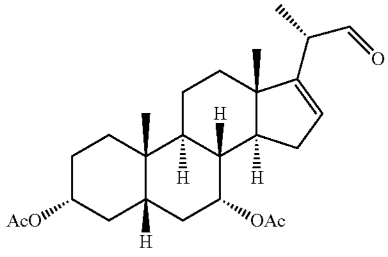

29

To a 50 ml flask is added compound 28 (1.00 eq) and DCM (5.00 mL). The reaction is cooled to 0° C.; paraformaldehyde (5.00 eq) is added to the reaction at 0° C., followed by adding $BF_3.Et_2O$ (0.10 eq) to the reaction at 0° C. The reaction is warmed to 15° C., and stirred at 15° C. for 2 hrs. The reaction is diluted with DCM (50 ml), and quenched by water (30 ml). The organic layer is concentrated in vacuo. The residue is purified to give an intermediate product. To a 10 ml tube is added $(COCl)_2$ (2.40 eq) and DCM (6.00 mL). The mixture is cooled to −78° C. DMSO (4.00 eq) is added drop-wise to the reaction mixture at −78° C. After addition, the reaction is stirred at −78° C. for 0.5 hrs. The intermediate product is then added to the reaction at −78° C. It is stirred at −78 for 0.5 hrs. TEA (10.00 eq) is added drop-wise at −78° C. After addition, the reaction is warmed to 15° C., and stirred at 15° C. for 0.5 hr. The reaction is diluted with DCM (50 ml), and quenched by water (30 ml). The separated organic layer is concentrated in vacuo. The residue is purified to give compound 29.

Step 3

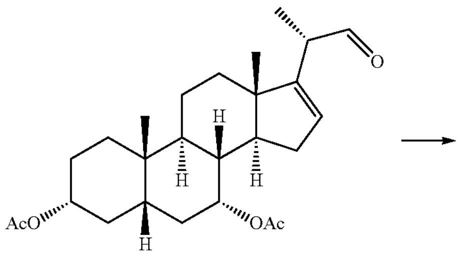

29

-continued

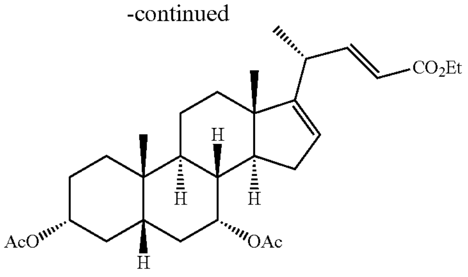

30

To a 10 ml tube is added NaH (4.00 eq) and THF (2.00 mL), followed by adding ethyl 2-diethoxyphosphorylacetate (5.00 eq) to the flask at 15° C. The resulted mixture is stirred at 15° C. for 10 mins. Compound 29 (1.00 eq) is added to the flask at 15° C., and stirred at 15° C. for 0.5 hr. The reaction is then quenched by water (5 ml), and extracted with DCM (2*30 ml). The organic layer is concentrated in vacuo. The residue is purified to give compound 30.

Step 4

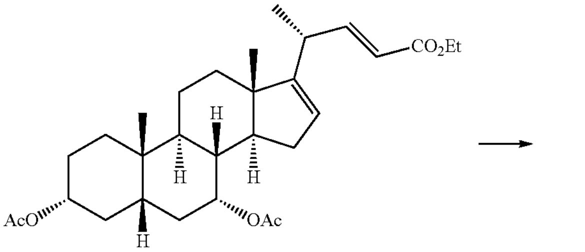

30

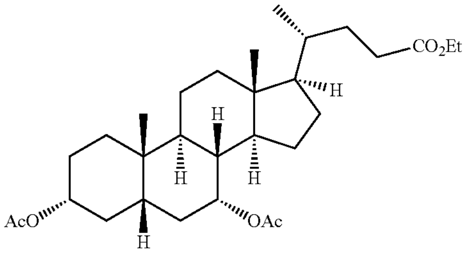

31

To a 35 ml pressure tube is added compound 30 (1.00 eq), EtOH (4.00 mL) and Pd/C (0.1 eq based on Pd) at 25° C. The mixture is purged with $H_2$ gas (50 psi) and stirred at 25° C. for 4 hrs. The resulting mixture is filtered, the filtrate is concentrated in vacuo to give compound 31.

Step 5

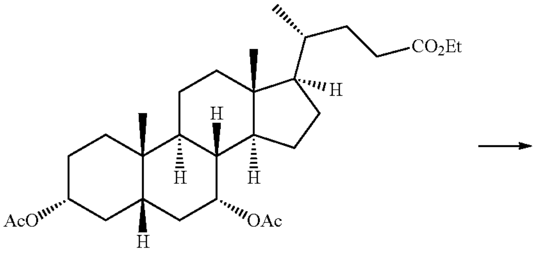

31

-continued

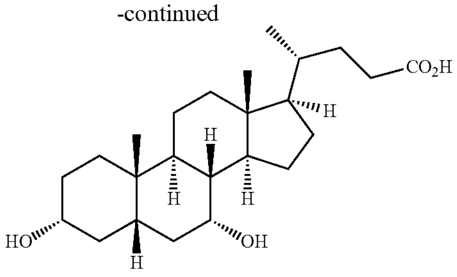

Chenodeoxycholic acid

To a solution of compound 31 (1.00 eq) in MeOH (4.00 mL) is added NaOH (12.00 eq) at 25° C. After that, the reaction is heated to 60° C., and stirred at 60° C. for 2 hrs. The reaction is than allowed to cool to rt. After it is concentrated in vacuo, the resulting residue is dissolved in water (5 ml), and the pH is adjusted by HCl to PH=3. The resulted aqueous layer is extracted with EA (3*15 ml). The organic layer is concentrated in vacuo to give Chenodeoxycholic acid.

Example 6

Characteristics of Synthetic Cholic Acid

A few process impurities (see e.g., impurities 1-4 in FIG. 2) in the final cholic acid produced in Example 1 or 2 have been isolated using preparative HPLC (e.g., Shimadzu LC-20AP prep HPLC system), with $H_2O$ (0.1% TFA) and acetonitrile as eluents, Column: Luna C18 300*50 mm, 10 u, ELSD as monitor and identified as Compounds 32, 33, 34, and 35 as follows. Those skilled in the art would know how to adjust the flow rate and gradients to obtain optimal separation. The purity of the isolated product can be analyzed by analytical HPLC, for example, also using $H_2O$ (0.1% TFA) and acetonitrile as eluents, Column: Luna C18 100*30 mm, 5 u.

The $^1H$ NMR spectra below were obtained using Bruker AV 400 (400 MHz); and $^{13}C$ NMR spectra below were obtained using Bruker AV 400 (100 MHz). In reporting the NMR spectra, the following conventions are used: s=singlet, d=doublet, t=triplet, m=multiplet, br s=broad singlet, ov=overlapped; a and b show the two different protons in prochiral methylene.

Compound 32 is a process impurity having the following structure:

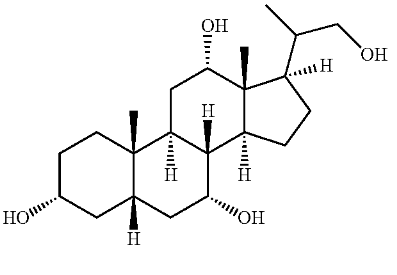

-continued

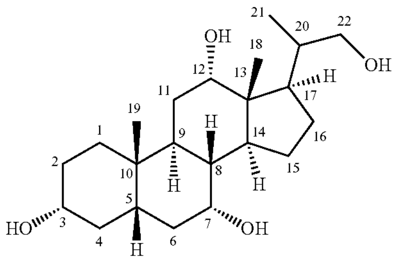

Compound 32 can be derived, for example, from hydrogenation of a product formed in Step 8 (part a) of Example 1 followed by deprotection. Mass spectral analysis shows a peak at 733.5 (Positive Scan, 2M+1). The assignments of chemical shifts (in ppm) of proton and carbon are tabulated in Table 2-A.

TABLE 2A

Chemical Shift Assignments for Compound 32 in DMSO-$d^6$ (25° C.)

| Position | $^1$H NMR$_{(ppm)}$(nH, m) | $^{13}$C NMR$_{(ppm)}$ |
|---|---|---|
| 1a | 0.84, 1H, ov | 35.3 |
| 1b | 1.64, 1H, ov | |
| 2a | 1.42, 1H, ov | 30.4 |
| 2b | 1.27, 1H, ov | |
| 3 | 3.18, 1H, tt | 70.4 |
| 4a | 1.45, 1H, ov | 39.6 |
| 4b | 2.23, 1H, ov | |
| 5 | 1.23, 1H, ov | 41.5 |
| 6a | 1.36, 1H, ov | 34.9 |
| 6b | 1.79, 1H, ov | |
| 7 | 3.60, 1H, br.s | 66.3 |
| 8 | 1.32, 1H, ov | 39.3 |
| 9 | 2.15, 1H, ov | 26.3 |
| 10 | — | 34.4 |
| 11 | 1.40, 2H, ov | 28.6 |
| 12 | 3.79, 1H, br.s | 71.0 |
| 13 | — | 45.9 |
| 14 | 1.95, 1H, ov | 41.1 |
| 15a | 0.96, 1H, ov | 23.0 |
| 15b | 1.64, 1H, ov | |
| 16a | 1.16, 1H, ov | 27.0 |
| 16b | 1.67, 1H, ov | |
| 17 | 1.78, 1H, ov | 43.3 |
| 18 | 0.59, 3H, s | 12.5 |
| 19 | 0.81, 3H, s | 22.7 |
| 20 | 1.33, 1H, ov | 39.4 |
| 21 | 0.98, 3H, d, 6.48 Hz | 15.7 |
| 22a | 3.01, 1H, m | 65.9 |
| 22b | 3.40, 1H, m | |
| 3-OH | 4.32, 1H, d, 4.40 Hz | — |
| 7-OH | 4.00, 1H, d, 3.30 Hz | — |
| 12-OH | 4.09, 1H, d, 3.55 Hz | — |
| 22-OH | 4.22, 1H, t, 5.26 Hz | — |

The $^1$H-NMR spectrum of Compound 32 shows the structure characteristic of cholesteric acid derivative, which is one of steroids. All protons resonate in the aliphatic area of the spectrum and three methyl signals can be observed in the high field: 0.59 ppm (3H, s, H-18), 0.81 ppm (3H, s, H-19) and 0.98 ppm (3H, d, J=6.48 Hz, H-21). In the lower field of the aliphatic area, three methines adjacent to the oxygen atom can be found: 3.79 ppm (1H, m, H-12), 3.60 ppm (1H, br.s, H-7) and 3.18 ppm (1H, m, H-3). Meanwhile, one methylene adjacent to the oxygen atom, which is a group in the C17 side chain of steroids skeleton, resonate at 3.01 ppm (1H, m) and 3.40 ppm (1H, m) in the lower field area.

In the COSY spectrum, the methylene at 3.01 ppm and 3.40 ppm correlate with the methine at 1.33 ppm (H-20) and active proton at 4.22 ppm (1H, t, J=5.26 Hz). And that methine at 1.33 ppm also correlate with the methyl at 0.98 ppm (H-21) and methine at 1.78 ppm (H-17). These signals prove that the C17 side chain is '1-hydroxypropan-2-yl'. In the HMBC spectrum, H-19 correlate with C-1, C-10, C-5 and C-9; H-18 correlate with C-12, C-13, C-14 and C-17; H-21 correlate with C-20, C-22 and C-17. Those correlation signals support the correct attachment of several groups. In the NOESY spectrum, the relative configuration of AB ring is 'cis' because of the fact that methyl at 0.81 ppm (H-19) correlate with methine at 1.23 ppm (H-5); B/C ring's is 'trans' as methyl H-19 correlated with methine at 1.32 (H-8) and don't correlate with methine at 2.14 ppm (H-9); C/D ring's is 'trans' as methyl at 0.59 ppm (H-18) don't correlate with methine at 1.95 ppm (H-14) and correlate with H-8; the relative configuration of C-17 is 'β' because methyl at 0.59 ppm correlate with methine at 1.33 ppm (H-20) and don't correlate with methine at 1.78 ppm (H-17); The correlation signals between methine at 3.18 ppm (H-3) and H-5, methine at 3.60 ppm (H-7) and H-8/H-6 (1.36 ppm and 1.78 ppm), methine at 3.79 ppm and H-19 can support the conclusion of 3α(OH),7α(OH) and 12α(OH). However, the configuration of C-20 cannot be ensured based on the NMR studies because the chiral center is outside the ring. In conclusion, we can determine that the configuration of Compound 32 is 3α, 5β,7α,8β,9α,10β,12α,13β,14α,17β, 20(R or S).

Compound 33 is a process impurity having the following structure:

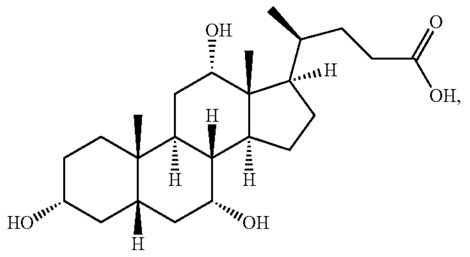

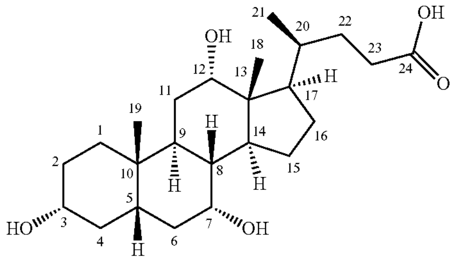

Compound 33 is a diastereomer of cholic acid at the C20 position, which can be derived, for example, from a minor isomer formed in Step 8 (or epimerization) of Example 1 that carried through the synthesis until cholic acid. Mass spectral analysis shows a peak at 817.6 (Positive Scan, 2M+1). The assignments of chemical shifts (in ppm) of proton and carbon are tabulated in Table 2-B:

TABLE 2B

| Chemical Shift Assignments for Compound 33 in DMSO-d6 (25° C.) | | |
|---|---|---|
| Position | $^{1}$H NMR$_{(ppm)}$(nH, m) | $^{13}$C NMR$_{(ppm)}$ |
| 1a | 0.83, 1H, ov | 35.3 |
| 1b | 1.64, 1H, ov | |
| 2a | 1.41, 1H, ov | 30.3 |
| 2b | 1.28, 1H, ov | |
| 3 | 3.18, 1H, tt | 70.5 |
| 4a | 1.45, 1H, ov | 39.6 |
| 4b | 2.21, 1H, ov | |
| 5 | 1.23, 1H, ov | 41.5 |
| 6a | 1.36, 1H, ov | 34.9 |
| 6b | 1.79, 1H, ov | |
| 7 | 3.61, 1H, br.s | 68.3 |
| 8 | 1.33, 1H, ov | 39.5 |
| 9 | 2.14, 1H, ov | 26.2 |
| 10 | — | 34.6 |
| 11a | 1.44, 1H, ov | 28.5 |
| 11b | 1.38, 1H, ov | |
| 12 | 3.80, 1H, br.s | 71.0 |
| 13 | — | 45.7 |
| 14 | 1.99, 1H, ov | 41.3 |
| 15a | 0.96, 1H, ov | 22.7 |
| 15b | 1.65, 1H, ov | |
| 16a | 1.15, 1H, ov | 27.4 |
| 16b | 1.67, 1H, ov | |
| 17 | 1.78, 1H, ov | 46.3 |
| 18 | 0.59, 3H, s | 12.5 |
| 19 | 0.80, 3H, s | 22.6 |
| 20 | 1.34, 1H, ov | 34.4 |
| 21 | 0.78, 3H, d, 5.50 Hz | 18.3 |
| 22a | 1.87, 1H, ov | 29.3 |
| 22b | 1.36, 1H, ov | |
| 23a | 2.35, 1H, ov | 31.1 |
| 23b | 2.09, 1H, ov | |
| 24 | — | 175.2 |

The $^{1}$H-NMR spectrum of Compound 33 shows the structure characteristic of cholesteric acid derivative, which is one of steroids. All protons resonate in the aliphatic area of the spectrum and three methyl signals can be observed in the high field: 0.59 ppm (3H, s, H-18), 0.80 ppm (3H, s, H-19) and 0.78 ppm (3H, d, J=5.50 Hz, H-21). In the lower field of the aliphatic area, three methines adjacent to the oxygen atom can be found: 3.80 ppm (1H, br.s, H-12), 3.61 ppm (1H, br.s, H-7) and 3.18 ppm (1H, tt, $J_1$=10.3 Hz, $J_2$=4.0 Hz, H-3).

In the COSY spectrum, the methyl at 0.78 ppm (H-21) correlate with the methine at 1.34 ppm (H-20) and H-20 correlate with methine at 1.79 ppm (H-17). According to the HMBC spectrum, H-21 correlate with carbon at 46.3 ppm (C-17), 39.3 ppm (C-22). The two methylenes H22 and H23 correlate with carbonyl at 175.2 ppm (C-24). These signals prove that the C17 side chain is '1-n-valeric acid-4-yl'.

In the HMBC spectrum, H-19 correlate with C-1, C-5, C-9 and C-10; H-18 correlate with C-12,C-13,C-14 and C-17. Those correlation signals support the correct attachment of several groups.

In the NOESY spectrum, the relative configuration of AB ring is 'cis' because of the fact that methyl at 0.80 ppm (H-19) correlate with methine at 1.23 ppm (H-5); B/C ring's is 'trans' as methyl H-19 correlate with methine at 1.33 (H-8) and don't correlate with methine at 2.14 ppm (H-9); C/D ring's is 'trans' as methyl at 0.59 ppm (H-18) don't correlate with methine at 1.99 ppm (H-14) and correlate with H-8; the relative configuration of C-17 is 'β' because methyl at 0.59 ppm correlate with methine at 1.34 ppm (H-20) and don't correlate with methine at 1.78 ppm (H-17); The correlation signals between methine at 3.18 ppm (H-3) and H-5, methine at 3.61 ppm (H-7) and H-8, H-6(1.36 ppm and 1.79 ppm), methine at 3.80 ppm and H-18 can support the conclusion of 3α(OH),7α(OH) and 12α(OH). However, the configuration of C-20 cannot be ensured based on NMR because the chiral center is outside the ring. In conclusion, we can determine that the configuration is 3α,5β,7α,8β,9α,10β,12β,13β,14α,17β,20(R or S). As Compound 33 has the same stereochemistry at the 3, 5, 7, 8, 9, 10, 12, 13, 14, and 17 position as that of cholic acid, the C20 stereochemistry of Compound 33 is assigned as "S", as cholic acid has a "R" configuration at C20.

Compound 34 is a process impurity having the following structure:

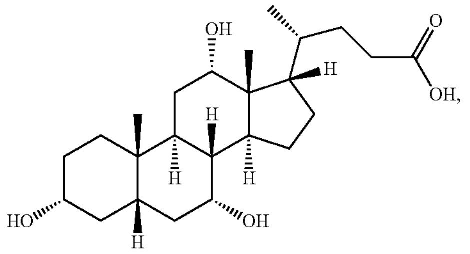

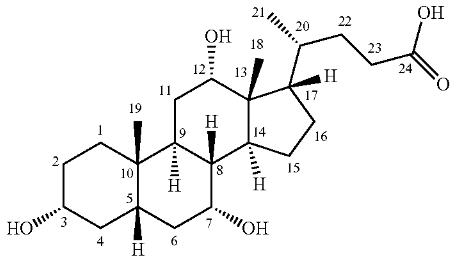

Compound 34 is a diastereomer of cholic acid at the C17 position, which can be derived, for example, from a minor isomer formed in Step 10 of Example 1 that carried through the synthesis until cholic acid. Mass spectral analysis shows a peak at 407.3 (Negative Scan, M-1). The assignments of chemical shifts (in ppm) of proton and carbon are tabulated in Table 2-C:

TABLE 2C

| Chemical Shift Assignments for Compound 34 in chloroform-d (25° C.) | | |
|---|---|---|
| Position | $^{1}$H NMR$_{(ppm)}$(nH, m) | $^{13}$C NMR$_{(ppm)}$ |
| 1a | 0.97, 1H, ov | 35.4 |
| 1b | 1.74, 1H, ov | |
| 2a | 1.40, 1H, ov | 29.9 |
| 2b | 1.67, 1H, ov | |
| 3 | 3.47, 1H, m | 71.9 |
| 4a | 1.78,1H, ov | 39.4 |
| 4b | 2.22, 1H, ov | |
| 5 | 1.39, 1H, ov | 41.4 |
| 6a | 1.57, 1H, ov | 34.4 |
| 6b | 1.92, 1H, ov | |
| 7 | 3.94, 1H, br.s | 69.3 |
| 8 | 1.62, 1H, ov | 39.2 |
| 9 | 2.27, 1H, ov | 26.4 |
| 10 | — | 34.8 |
| 11 | 1.59, 2H, ov | 29.7 |
| 12 | 4.27, 1H, br.s | 73.3 |
| 13 | — | 47.1 |
| 14 | 2.00, 1H, ov | 40.0 |
| 15a | 1.10, 1H, ov | 25.2 |
| 15b | 1.71, 1H, ov | |
| 16a | 1.28, 1H, ov | 29.4 |

TABLE 2C-continued

| Chemical Shift Assignments for Compound 34 in chloroform-d (25° C.) | | |
|---|---|---|
| Position | $^1$H NMR$_{(ppm)}$(nH, m) | $^{13}$C NMR$_{(ppm)}$ |
| 16b | 1.84, 1H, ov | |
| 17 | 1.40, 1H, ov | 55.9 |
| 18 | 0.78, 3H, s | 24.2 |
| 19 | 0.88, 3H, s | 22.3 |
| 20 | 1.90, 1H, ov | 34.7 |
| 21 | 0.80, 3H, d, 6.36 Hz | 18.1 |
| 22a | 1.15, 1H, ov | 31.9 |
| 22b | 2.04, 1H, ov | |
| 23 | 2.43, 2H, m | 32.1 |
| 24 | — | 178.5 |

The $^1$H-NMR spectrum of Compound 34 shows the structure characteristic of cholesteric acid derivative, which is one of steroids. All protons resonate in the aliphatic area of the spectrum and three methyl signals can be observed in the high field: 0.77 ppm (3H, s, H-18), 0.88 ppm (3H, s, H-19) and 0.80 ppm (3H, d, J=6.48 Hz, H-21). In the lower field of the aliphatic area, three methines adjacent to the oxygen atom can be found: 4.27 ppm (1H, br.s, H-12), 3.94 ppm (1H, br.s, H-7) and 3.47 ppm (1H, m, H-3).

In the COSY spectrum, the methyl at 0.80 ppm (H-21) correlate with the methine at 1.90 ppm (H-20) and H-20 correlate with methine at 1.40 ppm (H-17). According to the HMBC spectrum, H-21 correlate with carbon at 55.9 ppm (C-17), 31.9 ppm (C-22). The two methylenes H22 and H23 correlate with carbonyl at 178.5 ppm (C-24). These signals prove that the C17 side chain is '1-n-valeric acid-4-yl'.

In the HMBC spectrum, H-18 correlate with C-1, C-10, C-5 and C-9; H-19 correlate with C-12,C-13,C-14 and C-17; H-21 correlate with C-20, C-22 and C-17. Those correlation signals support the correct attachment of several groups.

In the NOESY spectrum, the relative configuration of AB ring is 'cis' because of the fact that methyl at 0.88 ppm (H-19) correlate with methine at 1.39 ppm (H-5); B/C ring's is 'trans' as methyl H-19 correlate with methine at 1.62 (H-8) and don't correlate with methine at 2.27 ppm (H-9); C/D ring's is 'trans' as methyl at 0.78 ppm (H-18) don't correlate with methine at 2.00 ppm (H-14) and correlate with H-8; the relative configuration of C-17 is 'a' because methyl at 0.78 ppm correlate with methine at 1.39 ppm (H-17) and don't correlate with methine at 1.90 ppm (H-20); The correlation signals between H-3 and H-5, H-7 and H-8, H-6 (1.57 ppm and 1.92 ppm), H-12 and H-18 can support the conclusion of 3a(OH),7a(OH) and 12a(OH).

However, the configuration of C-20 cannot be ensured based on the NMR studies because the chiral center is outside the ring. In conclusion, we can determine that the configuration is 3α, 5β,7α,8β,9α,10β,12α,13β,14α,17α, 20(R or S). Nevertheless, as Compound 34 is a diastereomer of Compound 35 (see below) with the only difference being the C20 stereochemistry, and X-ray crystal structure of Compound 35 shows that it has a C20 S configuration, the stereochemistry at C20 of Compound 34 is assigned as R configuration.

Compound 35 is a process impurity having the following structure:

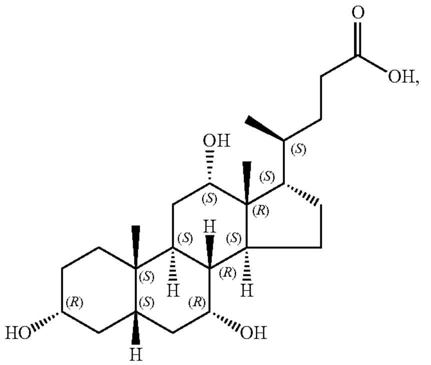

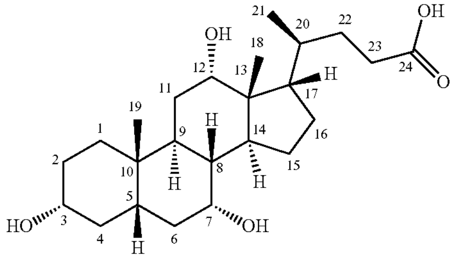

Compound 35 is a diastereomer of Compound 34 at the C20 position, which can be derived, for example, from a minor isomer formed in Steps 8-10 of Example 1 that carried through the synthesis until cholic acid. Mass spectral analysis shows a peak at 407.2 (Negative Scan, M-1). The assignments of chemical shifts (in ppm) of proton and carbon are tabulated in Table 2-D:

TABLE 2D

| Chemical Shift Assignments for Compound 35 in chloroform-d (25° C.) | | |
|---|---|---|
| Position | $^1$H NMR$_{(ppm)}$(nH, m) | $^{13}$C NMR$_{(ppm)}$ |
| 1a | 0.97, 1H, ov | 34.3 |
| 1b | 1.75, 1H, ov | |
| 2a | 1.37, 1H, ov | 29.7 |
| 2b | 1.66, 1H, ov | |
| 3 | 3.48, 1H, tt | 71.9 |
| 4a | 1.76, 1H, ov | 39.1 |
| 4b | 2.13, 1H, ov | |
| 5 | 1.41, 1H, ov | 41.3 |
| 6a | 1.57, 1H, ov | 34.3 |
| 6b | 1.94, 1H, ov | |
| 7 | 3.94, 1H, br.s | 69.2 |
| 8 | 1.61, 1H, ov | 39.8 |
| 9 | 2.25, 1H, ov | 26.3 |
| 10 | — | 34.8 |
| 11a | 1.56, 1H, ov | 29.6 |
| 11b | 1.65, 1H, ov | |
| 12 | 4.06, 1H, br.s | 73.1 |
| 13 | — | 48.0 |
| 14 | 2.01, 1H, ov | 39.5 |
| 15a | 1.16, 1H, ov | 25.3 |
| 15b | 1.80, 1H, ov | |
| 16a | 1.43, 1H, ov | 25.6 |
| 16b | 1.82, 1H, ov | |
| 17 | 1.57, 1H, ov | 55.7 |
| 18 | 0.75, 3H, s | 23.8 |
| 19 | 0.89, 3H, s | 22.2 |
| 20 | 1.99, 1H, ov | 34.2 |
| 21 | 0.91, 3H, d, 6.48 Hz | 20.5 |
| 22a | 1.08, 1H, ov | 29.5 |
| 22b | 1.98, 1H, ov | |
| 23 | 2.36, 2H, m | 32.4 |
| 24 | — | 178.5 |

The $^1$H-NMR spectrum of Compound 35 shows the structure characteristic of cholesteric acid derivative, which is one of steroids. All protons resonate in the aliphatic area of the spectrum and three methyl signals can be observed in the high field: 0.75 ppm (3H, s, H-18), 0.89 ppm (3H, s, H-19) and 0.91 ppm (3H, d, J=6.48 Hz, H-21). In the lower field of the aliphatic area, three methines adjacent to the oxygen atom can be found: 4.06 ppm (1H, br.s, H-12), 3.94 ppm (1H, br.s, H-7) and 3.48 ppm (1H, m, H-3).

In the COSY spectrum, the methyl at 0.91 ppm (H-21) correlate with the methine at 1.99 ppm (H-20) and H-20 correlate with methine at 1.57 ppm (H-17). According to the HMBC spectrum, H-21 correlate with carbon at 55.7 ppm (C-17), 29.5 ppm (C-22). The two methylenes H22 and H23 correlate with carbonyl at 178.5 ppm (C-24). These signals prove that the C17 side chain is '1-n-valeric acid-4-yl'.

In the HMBC spectrum, H-18 correlate with C-1, C-10, C-5 and C-9; H-19 correlate with C-12, C-13, C-14 and C-17; H-21 correlate with C-20, C-22 and C-17. Those correlation signals support the correct attachment of several groups.

In the NOESY spectrum, the relative configuration of AB ring is 'cis' because of the fact that methyl at 0.89 ppm (H-19) correlate with methine at 1.41 ppm (H-5); B/C ring's is 'trans' as methyl H-19 correlate with methine at 1.61 (H-8) and don't correlate with methine at 2.25 ppm (H-9); C/D ring's is 'trans' as methyl at 0.75 ppm (H-18) don't correlate with methine at 2.01 ppm (H-14) and correlate with H-8; the relative configuration of C-17 is 'α' because methyl at 0.75 ppm correlate with methine at 1.57 ppm (H-17) and don't correlate with methine at 1.99 ppm (H-20); The correlation signals between H-3 and H-5, H-7 and H-8, H-6 (1.57 ppm and 1.92 ppm), H-12 and H-18 can support the conclusion of 3α(OH),7α(OH) and 12α(OH).

However, the configuration of C-20 cannot be ensured based on NMR studies because the chiral center is outside the ring. In conclusion, we can determine that the configuration of Compound 35 is 3α,5β,7α,8β,9α,10β,12α,13β,14α,17α,20(R or S).

Nonetheless, an X-ray structure of a crystal of Compound 35 was obtained, which concludes that the stereochemistry of Compound 35 at C20 position is in the S configuration. See FIG. 1.

The X-ray structural analysis: A sample of Compound 35 was dissolved in acetone and kept in a half sealed vial. The solvent evaporate slowly at room temperature. A crystal suitable in size was obtained in the second day. Its transparency was check by microscope and then the crystal was sent for X-ray test using Rigaku Saturn Diffractometer using graphic-monochromated Mo Kα radiation (λ=0.71073 Å). The following parameter was used: Radiation monochromator: artificial multimembrane focusing mirror; Single tube diameter: Φ=0.50 mm; Distance from the crystal to the CCD detector: d=45 mm; Tube Pressure: 50 kV; Tube Flow: 16 mA. A total of 27071 reflections were collected in the theta range from 2.303 to 31.246°. The limiting indices were: $-12 \le h \le 12$, $-12 \le k \le 12$, $-42 \le l \le 43$; which yielded 7098 unique reflections ($R_{int}$=0.0650). The structure was solved using direct methods and was refined by full-matrix least-squares on F2 values. Non-hydrogen atoms were refined anisotropically. Hydrogen atoms were fixed at calculated positions and refined using a riding mode. The total number of refined parameters was 310, compared with 7098 data. All reflections were included in the refinement. The goodness of fit on F2 was 1.031 with a final R value for [I>2σ(I)] R=0.0668 and $R_w$=0.1664. The largest differential peak and hole were 0.391 and −0.413 e. $Å^{-3}$, respectively.

The crystal was a colorless prism with the following dimensions: 0.20×0.18×0.12 $mm^3$. The symmetry of the crystal structure was assigned the orthorhombic space group P2(1)2(1)2(1) with the following parameters: a=8.4747(4) Å, b=9.2565(4) Å, c=29.9531(11) Å, α=β=γ=90°, V=2349.7 (17) $Å^3$, Z=4, Dc=1.240 $Mg/m^3$, F(000)=968, μ(Mo Kα)=0.088 $mm^{-1}$, and T=113(2) K. See Table 3 below.

TABLE 3

Summary of X-ray Crystallographic Data of Compound 35

| | |
|---|---|
| Crystal Size | 0.20 × 0.18 × 0.12 $mm^3$ |
| Radiation Type | Mo Kα (λ = 0.71073 Å) |
| Space Group | Orthorhombic P2(1)2(1)2(1) |
| Cell Size | a = 8.4747(4) Å<br>b = 9.2565(4) Å<br>c = 29.9531(11) Å<br>α = 90°<br>β = 90°<br>γ = 90° |
| Cell Volume | V = 2349.70(17) $Å^3$ |
| Cell Formula Units | Z = 4 |
| Crystal Density | $D_c$ = 1.240 $Mg/m^3$ |
| Crystal F(000) | 968 |
| Absorption Coefficient mu | μ(Mo Kα) = 0.088 $mm^{-1}$ |
| Limiting Indices | $-12 \le h \le 12$<br>$-12 \le k \le 12$<br>$-42 \le l \le 43$ |
| Cell Measurement Temperature | T = 113(2) K. |
| Theta range for data collection | 2.303 to 31.246° |
| Goodness-of-fit on F^2 | 1.031 |
| Final R indices [I > 2sigma(I)] | R1 = 0.0668, wR2 = 0.1664 |
| R indices (all data) | R1 = 0.0877, wR2 = 0.1841 |
| Largest diff. peak and hole | 0.391 and −0.413 e · $Å^{-3}$ |
| Reflections collected/unique | 27071/7098 [$R_{(int)}$ = 0.0650] |

With respect to aspects of the invention described as a genus, all individual species are individually considered separate aspects of the invention. If aspects of the invention are described as "comprising" a feature, embodiments also are contemplated "consisting of or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed is:

1. A method of preparing cholic acid, an ester thereof, or a pharmaceutically or cosmetically acceptable salt thereof,

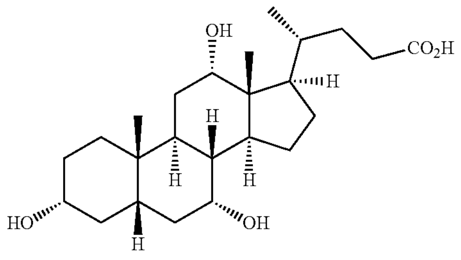

Cholic acid the method comprising:

a) reacting a compound of Formula III-1, or a geometric isomer thereof, with formaldehyde or paraformaldehyde in the presence of a Lewis acid Formula III-1

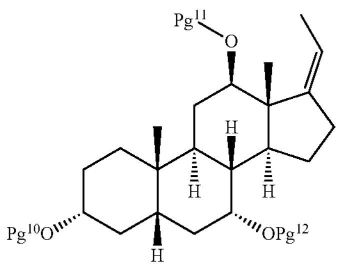

to form a compound of Formula III-2

Formula III-2

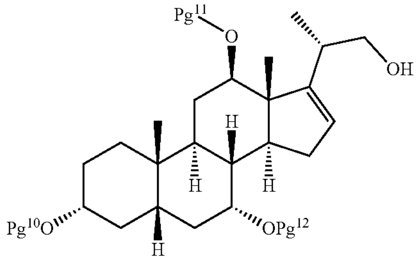

wherein $Pg^{10}$, $Pg^{11}$ and $Pg^{12}$ are each independently a hydroxyl protecting group;

b) oxidizing the compound of Formula III-2 to provide an aldehyde of Formula III-3

Formula III-3

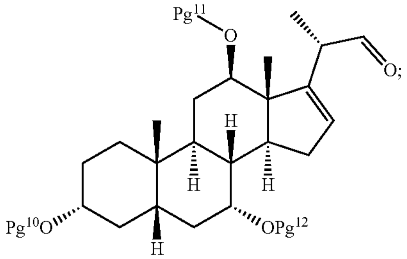

c) reacting the aldehyde of Formula III-3 with an olefin forming reagent to form a compound of Formula III-4, or a geometric isomer thereof, Formula III-4

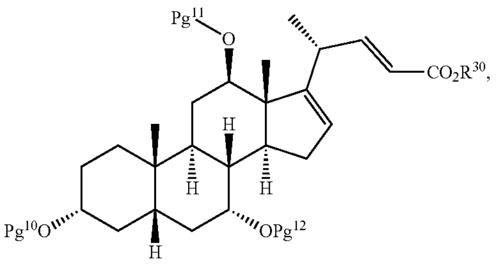

wherein $R^{30}$ is H or an optionally substituted alkyl group;

d) hydrogenating the compound of Formula III-4 with $H_2$ gas in the presence of a metal catalyst and subsequently removing the hydroxyl protecting groups, or removing the hydroxyl protecting groups in Formula III-4 and subsequently hydrogenating the deprotected compound with $H_2$ gas in the presence of a metal catalyst, to provide a triol of Formula III-5

Formula III-5

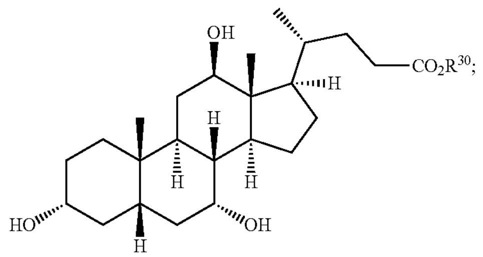

e) oxidizing the triol of Formula III-5 to provide a compound of Formula III-6,

Formula III-6

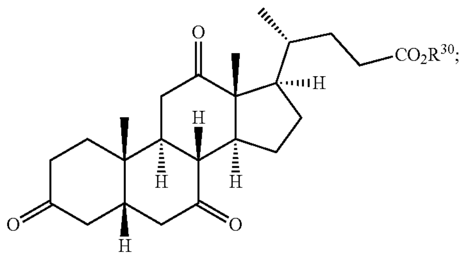

f) contacting the compound of Formula III-6 with a ketone reducing agent to form a compound of Formula III-7

Formula III-7

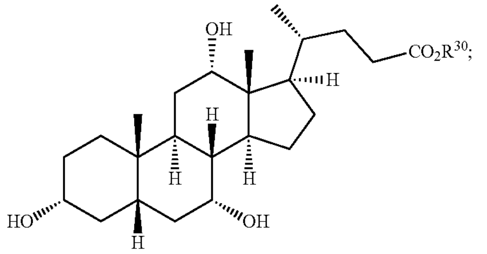

and g) optionally, when $R^{30}$ is not H in Formula III-7, hydrolyzing the compound of Formula III-7 to provide cholic acid.

2. The method of claim 1, further comprising forming a pharmaceutically or cosmetically acceptable salt of cholic acid.

3. The method of claim 1, wherein $Pg^{10}$, $Pg^{11}$ and $Pg^{12}$ are each acetyl.

4. The method of claim 1, wherein the Lewis acid in a) comprises $BF_3$.

5. The method of claim 1, wherein the oxidizing in b) comprises contacting the compound of Formula III-2 with a Swern oxidation reagent.

6. The method of claim 1, wherein the olefin forming reagent in c) comprises a phosphonate substituted acetate, a phosphorus ylide or a Reformatsky reagent.

7. The method of claim 6, wherein the olefin forming reagent is ethyl 2-diethoxyphosphorylacetate.

8. The method of claim 1, wherein the hydrogenating in d) comprises reacting the compound of Formula III-4 with $H_2$ at a pressure of about 15 psi to about 100 psi in the presence of Pd/C.

9. The method of claim 1, wherein the oxidizing in e) comprises contacting the triol of Formula III-5 with a Chromium based oxidizing agent, Swern oxidation reagent, 2-iodoxybenzoic acid (IBX) or 1,1,1-tri-acetoxy-1,1-dihydro-1,2-benziodoxol-3 (1H)-1 (Dess-Martin periodinane (DMP)).

10. The method of claim 1, wherein the ketone reducing agent in f) is lithium tri-tert-butoxyaluminum hydride ($LiAlH(O\text{-}tBu)_3$).

11. The method of claim 1, wherein $R^{30}$ in Formula III-7 is not H, and the method comprises contacting the compound of Formula III-7 with NaOH or LiOH.

12. The method of claim 1, wherein the compound of Formula III-1, or a geometric isomer thereof, is obtained from reacting a compound of Formula III-8 with an olefin forming reagent Formula III-8

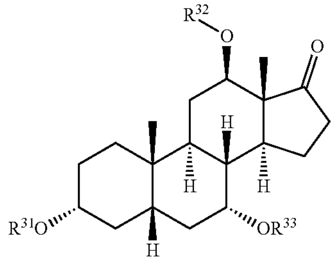

wherein $R^{31}$ is H or $Pg^{10}$; $R^{32}$ is H or $Pg^{11}$; and $R^{33}$ is H or $Pg^{12}$;

provided that when one or more of $R^{31}$, $R^{32}$ and $R^{33}$ are H, then a protecting step is followed after reacting the compound of Formula III-8 with the olefin forming reagent.

13. The method of claim 12, wherein the olefin forming reagent is a phosphorus ylide or its precursor.

14. The method of claim 13, wherein the olefin forming reagent is ethyl triphenylphosphine bromide.

15. The method of claim 12, wherein the compound of Formula III-8 is a compound of Formula III-8a, and is obtained from the method of preparing a compound of Formula III-8a Formula III-8a

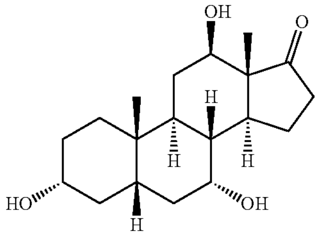

, the method comprising a) oxidizing dehydroepiandrosterone (DHEA) into a compound of Formula III-9

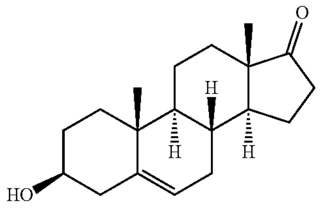

DHEA

Formula III-9

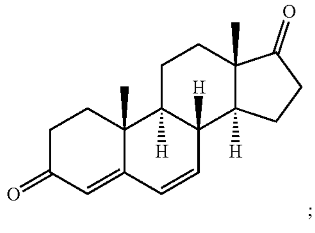

;

b) reacting the compound of Formula III-9 with an epoxide forming reagent to form an epoxide of Formula III-10

Formula III-10

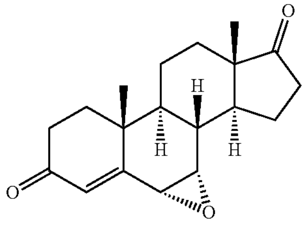

;

c) reducing the epoxide of Formula III-10 under hydrogenation condition to form a diketone of Formula III-11

Formula III-11

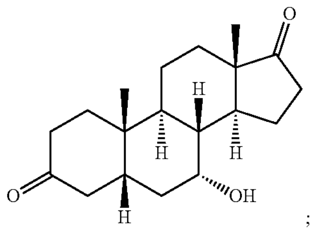

;

d) contacting the diketone of Formula III-11 with a ketone reducing agent to form a compound of Formula III-12

Formula III-12

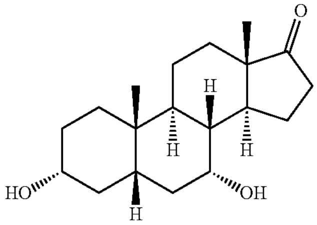

;

e) reacting the compound of Formula III-12 with an amine to form an imine of Formula III-13

Formula III-13

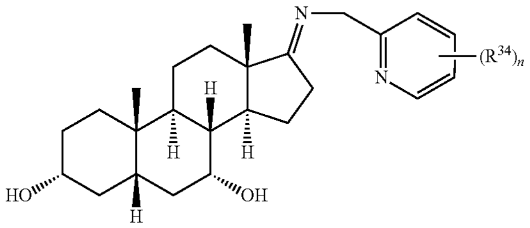

wherein n is 0, 1 or 2, and $R^{34}$ is $C_{1-6}$ alkyl; and f) oxidizing the imine of Formula III-13 with $O_2$ in the presence of a copper salt to form the compound of Formula III-8a.

* * * * *